United States Patent
Oka et al.

(10) Patent No.: US 12,152,260 B2
(45) Date of Patent: Nov. 26, 2024

(54) METHODS AND COMPOSITIONS FOR IN VIVO GENE EDITING BASED CELL-TYPE-SPECIFIC CELLULAR ENGINEERING

(71) Applicant: California Institute of Technology, Pasadena, CA (US)

(72) Inventors: Yuki Oka, Pasadena, CA (US); Allan-Hermann Pool, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 18/333,344

(22) Filed: Jun. 12, 2023

(65) Prior Publication Data

US 2024/0132861 A1   Apr. 25, 2024
US 2024/0228991 A9   Jul. 11, 2024

Related U.S. Application Data

(62) Division of application No. 16/845,009, filed on Apr. 9, 2020, now Pat. No. 11,702,644.

(60) Provisional application No. 62/832,504, filed on Apr. 11, 2019, provisional application No. 62/832,759, filed on Apr. 11, 2019.

(51) Int. Cl.
| | | |
|---|---|---|
| C12N 9/22 | (2006.01) | |
| A61K 9/00 | (2006.01) | |
| A61K 35/12 | (2015.01) | |
| A61K 38/00 | (2006.01) | |
| A61K 48/00 | (2006.01) | |
| A61P 25/04 | (2006.01) | |
| A61P 25/28 | (2006.01) | |
| C12N 15/11 | (2006.01) | |
| C12N 15/86 | (2006.01) | |
| C12N 15/90 | (2006.01) | |

(52) U.S. Cl.
CPC .............. *C12N 9/22* (2013.01); *A61K 9/0043* (2013.01); *A61K 35/12* (2013.01); *A61K 48/005* (2013.01); *C12N 15/11* (2013.01); *C12N 15/86* (2013.01); *C12N 15/90* (2013.01); *A61K 38/00* (2013.01); *C12N 2310/20* (2017.05); *C12N 2750/14143* (2013.01); *C12N 2800/80* (2013.01)

(58) Field of Classification Search
None
See application file for complete search history.

(56) References Cited

U.S. PATENT DOCUMENTS

| | | |
|---|---|---|
| 11,702,664 B2 | 7/2023 | Oka et al. |
| 2011/0027235 A1 | 2/2011 | Gregory et al. |
| 2018/0362601 A1 | 12/2018 | Miller et al. |

FOREIGN PATENT DOCUMENTS

| | | |
|---|---|---|
| CN | 108118057 | 6/2018 |
| WO | WO2018197020 | 11/2018 |

OTHER PUBLICATIONS

International Search Report and Written Opinion dated Sep. 4, 2020 in PCT Application No. PCT/US2020/027555.
Alhadeff et al., "A Neural Circuit for the Suppression of Pain by a Competing Need State," Cell 2018, 173(1), 140-152.
Augustine et al., "Hierarchical neural architecture underlying thirst regulation," Nature 2018, 555(7695), 204-209.
De Felipe et al., "Targeting of Proteins Derived from Self-Processing Polyproteins Containing Multiple Signal Sequences," Traffic 2004, 5, 616-626.
De Felipe, "Skipping the co-expression problem: the new 2A 'CHYSEL' technology," Genetic Vaccines and Therapy 2004, 2(13), in 6 pages.
Heimberg et al., "Low Dimensionality in Gene Expression Data Enables the Accurate Extraction of Transcriptional Programs from Shallow Sequencing," Cell Systems 2016, 2, 239-250.
Saper & Stornetta, "Central Autonomic System," The Rat Nervous System, Fourth Edition 2014, 629-673.
Suzuki et al., "In vivo genome editing via CRISPR/Cas9 mediated homology-independent targeted integration," Nature 2016, 540(7631), 144-149.
Zeisel et al., "Molecular Architecture of the Mouse Nervous System," bioRxiv 2018, 174, 999-1014. https://doi.org/10.1101/294918.
Notice of Allowance dated Feb. 16, 2023 in U.S. Appl. No. 16/845,009 in 12 pages.
Office Action dated Sep. 30, 2022 in U.S. Appl. No. 16/845,009 in 8 pages.

*Primary Examiner* — Suzanne M Noakes
*Assistant Examiner* — Jae W Lee
(74) *Attorney, Agent, or Firm* — Dickinson Wright PLLC

(57) ABSTRACT

Disclosed herein include methods and compositions for incorporating an effector gene into the genome of a cell. The method can comprise introducing into a cell a donor nucleic acid comprising a recognition site, a splice acceptor site, a self-cleaving peptide sequence, an effector gene, and an optional transcript stabilization element. The donor nucleic acid can be incorporated into the intron of a target gene differentially expressed in a unique cell type and/or in a cell during a unique cell state via non-homologous end joining (NHEJ)-dependent DNA repair. There are also provided, in some embodiments, methods and compositions for treating a disease or disorder in a subject.

18 Claims, 17 Drawing Sheets
(17 of 17 Drawing Sheet(s) Filed in Color)
Specification includes a Sequence Listing.

METHODS AND COMPOSITIONS FOR IN VIVO GENE EDITING BASED CELL-TYPE-SPECIFIC CELLULAR ENGINEERING

RELATED APPLICATIONS

The present application is divisional application of U.S. application Ser. No. 16/845,009, filed Apr. 9, 2020, which claims priority under 35 U.S.C. § 119(e) to U.S. Provisional Application No. 62/832,504, filed Apr. 11, 2019; and U.S. Provisional Application No. 62/832,759, filed Apr. 11, 2019. The entire contents of these applications are hereby expressly incorporated by reference in their entireties.

REFERENCE TO SEQUENCE LISTING

The present application is being filed along with a Sequence Listing in electronic format. The Sequence Listing is provided as a file entitled 30KJ-302421-US2_SequenceListing, created Jun. 11, 2023, which is 31 kilobytes in size. The information in the electronic format of the Sequence Listing is incorporated herein by reference in its entirety.

BACKGROUND

Field

The present disclosure relates generally to the field of cellular engineering.

Description of the Related Art

Emerging cellular profiling technologies have revealed a rich diversity of molecularly defined cell types in multiple organs including blood, immune system and the brain. As most disease conditions only affect one or just a few cell types in the body, precision therapies functionally correcting a particular cell type have become a highly attractive avenue for therapeutic intervention. Technologies that enable to selectively target and control specific cell types and cell states are therefore highly desirable.

Reliable and selective cell type specific engineering has to date been achievable only in animals where creating transgenic organisms is ethically permissible. Cell types and states here are defined by virtue of their gene expression. In such organisms, cell type specific manipulation has been achieved by expressing effector genes that bring about desired functional changes in the cell under the control of genome integrated DNA regions. This approach is usually a labor intensive and time consuming process.

Technical efforts in gaining cell-type-specific functional control in case germline modification of the genome is not feasible, fall into two major categories. The first relies on the use of promoter driver constructs, where the expression of the effector gene is under the control of a cell-type-specifically active gene promoter. These constructs are delivered by viral or non-viral delivery routes. Due to strict size limitations of the viral delivery route and the fact that many gene expression regulatory elements span large DNA regions, only a very limited set of cells in any given organism are reliably targetable through this method. An alternative to this approach is to deliver ubiquitously expressed effector genes by delivery methods that facilitate uptake only in desired cells. Using viral vectors, where the capsid composition can bias uptake is an example of this strategy. This approach, however, is suitable for targeting developmentally very disparate cell types where the membrane biophysics is profoundly distinct and is not suitable for reliable differential targeting of most cell types in the organism. In summary, none of the currently available technologies provide simple and selective functional control over the majority of distinct cell types in the body.

There is a need in the field for a technology that allows to use active genetic programs in the cell for selective functional manipulation of cell types and cell states.

SUMMARY

Disclosed herein include methods of incorporating an effector gene into the genome of a cell. In some embodiments, the method comprises: introducing into a cell: (i) a programmable nuclease or a nucleic acid encoding the programmable nuclease; (ii) a targeting molecule or a nucleic acid encoding the targeting molecule, and (iii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, wherein the cell comprises a target gene differentially expressed in a unique cell type and/or in a cell during a unique cell state, wherein the target gene comprises an intron comprising the recognition site, and wherein the targeting molecule is complementary to the recognition site and the programmable nuclease is capable of cleaving the recognition site, whereby the donor nucleic acid is capable of being incorporated into the intron through non-homologous end joining (NHEJ)-dependent DNA repair.

Disclosed herein include methods of incorporating an effector gene into the genome of a cell. In some embodiments, the method comprises: introducing into a cell: (i) a programmable nuclease or a nucleic acid encoding the programmable nuclease, wherein the programmable nuclease comprises a zinc finger nuclease (ZFN) and/or transcription activator-like effector nuclease (TALEN); and (ii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, wherein the cell comprises a target gene differentially expressed in a unique cell type and/or in a cell during a unique cell state, wherein the target gene comprises an intron comprising the recognition site, and wherein the programmable nuclease is capable of cleaving the recognition site, whereby the donor nucleic acid is capable of being incorporated into the intron through non-homologous end joining (NHEJ)-dependent DNA repair.

Disclosed herein include methods of treating a disease or disorder in a subject. In some embodiments, the method comprises: introducing into a cell of a subject in need thereof: (i) a programmable nuclease or a nucleic acid encoding the programmable nuclease; (ii) a targeting molecule or a nucleic acid encoding the targeting molecule, and (iii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, wherein the cell comprises a target gene differentially expressed in a unique cell type and/or in a cell during a unique cell state, wherein the target gene comprises an intron comprising the recognition site, and wherein the targeting molecule is complementary to the recognition site and programmable nuclease is capable of cleaving the recognition site, whereby the donor nucleic acid is capable of being incorporated into the intron through non-homologous end joining (NHEJ)-dependent DNA repair, and thereby the introducing treats the disease or disorder in the subject.

Disclosed herein include methods of treating a disease or disorder in a subject. In some embodiments, the method comprises: introducing into a cell of a subject in need thereof: (i) a programmable nuclease or a nucleic acid encoding the programmable nuclease, wherein the programmable nuclease comprises a zinc finger nuclease (ZFN) and/or transcription activator-like effector nuclease (TALEN); and (ii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, wherein the cell comprises a target gene differentially expressed in a unique cell type and/or in a cell during a unique cell state, wherein the target gene comprises an intron comprising the recognition site, and wherein the programmable nuclease is capable of cleaving the recognition site, whereby the donor nucleic acid is capable of being incorporated into the intron through non-homologous end joining (NHEJ)-dependent DNA repair, and thereby the introducing treats the disease or disorder in the subject.

In some embodiments, the donor nucleic acid comprises a translation frame linker. In some embodiments, the donor nucleic acid comprises the structure 5'-[recognition site]-[splice acceptor site]-[translation frame linker]-[self-cleaving peptide sequence]-[effector gene]-3'. In some embodiments, the donor nucleic acid comprises the target gene coding sequence downstream of the intron. In some embodiments, the donor nucleic acid comprises the structure 5'-[recognition site]-[splice acceptor site]-[target gene coding sequence downstream of the intron]-[self-cleaving peptide sequence]-[effector gene]-3'. In some embodiments, the recognition site of the donor nucleic acid and the recognition site of the intron are the same. In some embodiments, the recognition site does not exist after the donor nucleic acid has been properly incorporated into the intron. In some embodiments, the donor nucleic acid does not comprise a promoter.

In some embodiments, the effector gene is not expressed in a cell other than the unique cell type. In some embodiments, the expression of the effector gene in a cell other than the unique cell type is less than about 5 percent of the expression of the effector gene in the unique cell type. In some embodiments, the unique cell type comprises a unique gene expression pattern. In some embodiments, the unique cell type comprises a unique anatomic location. In some embodiments, the unique cell type comprises anatomically locally unique gene expression. In some embodiments, the effector gene is not expressed in a cell other than in a cell during the unique cell state. In some embodiments, the expression of the effector gene in a cell not in the unique cell state is less than about 10 percent of the expression of the effector gene in a cell during the unique cell state. In some embodiments, the effector gene is only expressed in a cell expressing the target gene. In some embodiments, the expression of the effector gene in a cell that does not express the target gene is less than about 5 percent of the expression of the effector gene in a cell that does express the target gene. In some embodiments, the unique cell state is caused by hereditable, environmental, and/or idiopathic factors.

In some embodiments, the cell comprises a plurality of cells. In some embodiments, the donor nucleic acid is capable of being incorporated into the intron of a post-mitotic cell. In some embodiments, the cell is a dividing cell, a non-dividing cell, a post-mitotic cell, or any combination thereof. In some embodiments, the cell is not in G2/M phase. In some embodiments, the cell is a eukaryotic cell (e.g., an immune cell, an epithelial cell, a muscle cell, an endothelial cell, a neuron, a stem cell, or any combination thereof) In some embodiments, the immune cell comprises a T cell, a B cell, a natural killer cell, a monocyte, a macrophage cell, a dendritic cell, or any combination thereof. In some embodiments, the stem cell comprises an embryonic stem cell, an induced pluripotent stem cell (iPSC), a hematopoietic stem/progenitor cell (HSPC), or any combination thereof. In some embodiments, the cell, the unique cell type and/or the cell in the unique cell state comprises a neuron. In some embodiments, the cell, the unique cell type and/or the cell in the unique cell state comprises a cell in a brain region. In some embodiments, the neuron is: involved in memory expression, involved in eating control, involved in addiction, a component of a motor control circuit, an anxiety processing neuron, an analgesia inducing neuron, an analgesia processing neuron, a pain-processing neuron, or any combination thereof. In some embodiments, the neuron is associated with a neurological disease or disorder. In some embodiments, the neuron can compensate, reverse or alleviate a disorder/disease state. In some embodiments, the unique cell type and/or the cell in the unique cell state causes and/or aggravates a disease or disorder. In some embodiments, the unique cell type and/or the cell in the unique cell state is associated with the pathology of a disease or disorder. In some embodiments, the cell is the cell of a subject. In some embodiments, the cell is the cell of a subject suffering from a disease or disorder.

In some embodiments, the disease or disorder is a blood disease, an immune disease, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or any combination thereof. In some embodiments, the disease or disorder comprises a neurological disease or disorder. In some embodiments, the neurological disease or disorder comprises Alzheimer's disease, Creutzfeld-Jakob's syndrome/disease, bovine spongiform encephalopathy (BSE), prion related infections, diseases involving mitochondrial dysfunction, diseases involving β-amyloid and/or tauopathy, Down's syndrome, hepatic encephalopathy, Huntington's disease, motor neuron diseases, amyotrophic lateral sclerosis (ALS), olivopontocerebellar atrophy, post-operative cognitive deficit (POCD), systemic lupus erythematosus, systemic clerosis, Sjogren's syndrome, Neuronal Ceroid Lipofuscinosis, neurodegenerative cerebellar ataxias, Parkinson's disease, Parkinson's dementia, mild cognitive impairment, cognitive deficits in various forms of mild cognitive impairment, cognitive deficits in various forms of dementia, dementia pugilistica, vascular and frontal lobe dementia, cognitive impairment, learning impairment, eye injuries, eye diseases, eye disorders, glaucoma, retinopathy, macular degeneration, head or brain or spinal cord injuries, head or brain or spinal cord trauma, convulsions, epileptic convulsions, epilepsy, temporal lobe epilepsy, myoclonic epilepsy, tinnitus, dyskinesias, chorea, Huntington's chorea, athetosis, dystonia, stereotypy, ballism, tardive dyskinesias, tic disorder, torticollis spasmodicus, blepharospasm, focal and generalized dystonia, nystagmus, hereditary cerebellar ataxias, corticobasal degeneration, tremor, essential tremor, addiction, anxiety disorders, panic disorders, social anxiety disorder (SAD), attention deficit hyperactivity disorder (ADHD), attention deficit syndrome (ADS), restless leg syndrome (RLS), hyperactivity in children, autism, dementia, dementia in Alzheimer's disease, dementia in Korsakoff syndrome, Korsakoff syndrome, vascular dementia, dementia related to HIV infections, HIV-1 encephalopathy, AIDS encephalopathy, AIDS dementia complex, AIDS-related dementia, major depressive disorder, major depression, depression, memory loss, stress, bipolar manic-depressive disorder, drug tolerance, drug tolerance to opioids, movement disorders, fragile-X syndrome, irritable bowel syndrome (IBS), migraine, multiple sclerosis (MS), muscle spasms, pain, chronic pain, acute pain, inflammatory pain, neuropathic pain, posttraumatic stress disorder (PTSD), schizophrenia, spasticity, Tourette's syndrome, eating disorders, food addiction, binge eating disorders, agoraphobia, generalized anxiety disorder, obsessive-compulsive disorder, panic disorder, social phobia, phobic disorders, substance-induced anxiety disorder, delusional disorder, schizoaffective disorder, schizophreniform disorder, substance-induced psychotic disorder, hypertension, or any combination thereof. In some embodiments, the neurological disease or disorder comprises a neuropsychiatric disorder.

In some embodiments, the neurological disease or disorder comprises pain. In some embodiments, the neurological disease or disorder comprises acute pain and/or chronic pain. In some embodiments, the pain is selected from the group comprising neuropathic pain, allodynia, hyperalgesia, dysesthesia, causalgia, neuralgia, and arthralgia. In some embodiments, the pain is associated with cancer, tumor pressure, bone metastasis, chemotherapy peripheral neuropathy, sciatica radiculopathy, lumbar radiculopathy, cervical radiculopathy, failed back surgery syndrome, *piriformis* syndrome, phantom pain, arachnoiditis, fibromyalgia, facet joint mediated pain, sympathetically-mediated pain syndrome, complex regional pain syndromes (crps), sacroiliac (si) joint mediated pain, meralgia paresthetica, localized myofacial pain syndromes, myofacial trigger points, diffuse myofacial pain syndrome, post-herpetic neuralgia, trigeminal neuralgia, glossopharyngeal neuralgia, post-epesiotomy scar pain, post-hernia repair scar pain, post-surgery scar pain, post-radiotherapy scar pain, vulvodynia, vaginismus, levator ani syndrome, chronic prostatitis, interstitial cystitis, first bite syndrome, rheumatoid arthritis pain, osteoarthritis pain, atypical odontalgia, phantom tooth pain, neuropathic orofacial pain, primary erythermalgia, atypical facial pain, or any combination thereof.

In some embodiments, the expression of the effector gene is capable of modulating cellular membrane potential. In some embodiments, the expression of the effector gene is capable of altering the membrane potential of the cell by depolarizing the cell and/or hyperpolarizing the cell. In some embodiments, the expression of the effector gene is capable of reducing synaptic transmission by at least 10 percent. In some embodiments, the expression of the effector gene is capable of blocking synaptic transmission. In some embodiments, the effector gene comprises Kir2.1. In some embodiments, the expression of the effector gene is capable of blocking synaptic transmission. In some embodiments, the effector gene comprises tetanus toxin (TNT). In some embodiments, the expression of the effector gene is capable of sensitizing the cell to a pharmacological compound, temperature change, or light. In some embodiments, the effector gene comprises a DREADD receptor and/or Channelrhodopsin-2. In some embodiments, the effector gene is capable of sensitizing the cell to a drug and/or to a prodrug. In some embodiments, the effector gene comprises cytosine deaminase and/or uracil phosphoribosyl transferase, and wherein the prodrug comprises 5-fluorocytosine (5-FC). In some embodiments, the effector gene comprises thymidine kinase (TK), and wherein the prodrug comprises ganciclovir. In some embodiments, the effector gene comprises an enzyme, a signal transduction protein, an ion-channel and/or a G-protein coupled receptor (GPCR). In some embodiments, the effector gene encodes a recombinant protein and/or a native protein. In some embodiments, the effector gene is capable of inducing cell death. In some embodiments, the effector gene comprises cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. In some embodiments, the unique cell state comprises a senescent cell state induced by a tumor microenvironment. In some embodiments, the senescent cell state induced by a tumor microenvironment comprises expression of CD57, KRLG1, TIGIT, or any combination thereof. In some embodiments, the effector gene comprises interleukin-12 (IL-12). In some embodiments, the effector gene comprises a diagnostic agent. In some embodiments, the effector gene comprises a diagnostic contrast agent. In some embodiments, the effector gene comprises green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, rsCherry, rsCherryRev, or any combination thereof.

In some embodiments, the method achieves an at least 10 percent higher targeting efficiency as compared to a homology directed repair (HDR)-based method. In some embodiments, the method achieves an at least 10 percent higher targeting efficiency as compared to a Homology Independent Targeted Integration (HITI)-based method integrating an effector gene into an exon. In some embodiments, the programmable nuclease is capable of inducing a double-stranded DNA break. In some embodiments, the programmable nuclease comprises *Streptococcus pyogenes* Cas9 (SpCas9) and/or *Staphylococcus aureus* Cas9 (SaCas9). In some embodiments, the programmable nuclease comprises Cas1, Cas1B, Cas2, Cas3, Cas4, Cas5, Cash, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csxl, Csx15, Csf1, Csf2, Csf3, Csf4, Cpfl, C2c1, C2c3, Cas12a, Cas12b, Cas12c, Cas12d, Cas12e, Cas13a, Cas13b, Cas13c, derivatives thereof, or any combination thereof. In some embodiments, the programmable nuclease comprises a zinc finger nuclease, TAL effector nuclease, meganuclease, MegaTAL, Tev-m TALEN, MegaTev, homing endonuclease, derivatives thereof, or any combination thereof.

In some embodiments, the self-cleaving peptide sequence comprises porcine teschovirus-1 2A peptide (P2A), Thosea asigna virus 2A peptide (T2A), equine rhinitis A virus 2A peptide (E2A), foot-and-mouth disease virus 2A peptide (F2A), or any combination thereof. In some embodiments, the transcript stabilization element is capable of enhancing the stability of a transcript of the effector gene. In some embodiments, the transcript stabilization element comprises woodchuck hepatitis post-translational regulatory element (WPRE), bovine growth hormone polyadenylation (bGH-polyA) signal sequence, human growth hormone polyadenylation (hGH-polyA) signal sequence, or any combination thereof. In some embodiments, the splice acceptor site is capable of being recognized and cleaved by a spliceosome. In some embodiments, the splice acceptor site comprises a branchpoint, a polypyrimidine tract, a 3' splice site, or any combination thereof. In some embodiments, the translation frame linker comprises between about 1 nucleotide and about 10 nucleotides and ensures that the effector gene is expressed in frame with the preceding exon of the target gene. In some embodiments, the translation frame linker places the effector gene in translational frame with the preceding exon of the target gene. In some embodiments, the recognition site is adjacent to a protospacer adjacent motif (PAM) capable of being recognized by the programmable nuclease. In some embodiments, the targeting molecule is capable of associating with the programmable nuclease. In some embodiments, the targeting molecule comprises single strand DNA or single strand RNA. In some embodiments, the targeting molecule comprises a single guide RNA (sgRNA). In some embodiments, the targeting molecule comprises a synthetic nucleic acid.

In some embodiments, the programmable nuclease, the targeting molecule, and/or the donor nucleic acid are encoded on the same nucleic acid. In some embodiments, the programmable nuclease, the targeting molecule, and/or the donor nucleic acid are encoded on different nucleic acids. In some embodiments, the nucleic acid encoding the programmable nuclease, the nucleic acid encoding the targeting molecule, and/or the nucleic acid encoding the donor nucleic acid comprise DNA and/or RNA. In some embodiments, the nucleic acid encoding the programmable nuclease, the nucleic acid encoding the targeting molecule, and/or the nucleic acid encoding the donor nucleic acid are component of a vector. In some embodiments, the vector is an AAV vector, a lentivirus, an integration-deficient lentivirus (IDLV), a plasmid vector, a naked DNA vector, a lipid nanoparticle, or any combination thereof. In some embodiments, the plasmid vector comprises a minicircle plasmid. In some embodiments, the AAV vector comprises AAV1, AAV2, AAV3, AAV4, AAV5, AAV6, AAV7, AAV8, AAV9, or any combination thereof. In some embodiments, the vector is a neurotropic viral vector. In some embodiments, the neurotropic viral vector comprises or is derived from Herpesviridae, varicella zoster virus, pseudorabies virus, cyromegalovirus, Epstein-barr virus, encephalitis virus, polio virus, coxsackie virus, echo virus, mumps virus, measles virus, rabies virus, or any combination thereof. In some embodiments, the vector comprises a heterologous promoter that drives expression of the programmable nuclease, the targeting molecule, and/or the donor nucleic acid. In some embodiments, the heterologous promoter is an inducible promoter. In some embodiments, the programmable nuclease, the targeting molecule, and/or the donor nucleic acid are encoded by a transgenic construct in the genome of the cell. In some embodiments, (i), (ii), and/or (iii) are a component of a ribonucleoprotein (RNP) complex.

The method can comprise: isolating the cell from the subject prior to the introducing step. The method can comprise: administering the cell into a subject after the introducing step. In some embodiments, the introducing step is performed in vivo, in vitro, and/or ex vivo. In some embodiments, the introducing step comprises calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof. In some embodiments, the introducing step comprises administering (i), (ii), and/or (iii) to a subject comprising the cell. In some embodiments, the introducing step comprises administering a vector to a subject comprising the cell, wherein the vector comprises (i), (ii), and/or (iii). In some embodiments, administering comprises intracranial injection, aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof. In some embodiments, administering comprises an injection into a brain region. In some embodiments, the brain region comprises the Lateral parabrachial nucleus, brainstem, Medulla oblongata, Medullary pyramids, Olivary body, Inferior olivary nucleus, Rostral ventrolateral medulla, Respiratory center, Dorsal respiratory group, Ventral respiratory group, Pre-Botzinger complex, Botzinger complex, Paramedian reticular nucleus, Cuneate nucleus, *Gracile* nucleus, Intercalated nucleus, Area postrema, Medullary cranial nerve nuclei, Inferior salivatory nucleus, Nucleus *ambiguus*, Dorsal nucleus of vagus nerve, Hypoglossal nucleus, Solitary nucleus, Pons, Pontine nuclei, Pontine cranial nerve nuclei, chief or pontine nucleus of the trigeminal nerve sensory nucleus (V), Motor nucleus for the trigeminal nerve (V), Abducens nucleus (VI), Facial nerve nucleus (VII), vestibulocochlear nuclei (vestibular nuclei and cochlear nuclei) (VIII), Superior salivatory nucleus, Pontine tegmentum, Respiratory centers, Pneumotaxic center, Apneustic center, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, Tectum, Corpora quadrigemina, inferior colliculi, superior colliculi, Pretectum, Tegmentum, Periaqueductal gray, Parabrachial area, Medial parabrachial nucleus, Subparabrachial nucleus (Kölliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars *compacta, Pars reticulata*, Interpeduncular nucleus, Cerebral peduncle, Crus cerebri, Mesencephalic cranial nerve nuclei, Oculomotor nucleus (III), Trochlear nucleus (IV), Mesencephalic duct (cerebral aqueduct, aqueduct of Sylvius), Pineal body, Habenular nucleim Stria medullares, *Taenia* thalami, Subcommissural organ, Thalamus, Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedi al nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventral lateral nucleus, Ventral posterior nucleus, Ventral posterior lateral nucleus, Ventral posterior medial nucleus, Metathalamus, Medial *geniculate* body, Lateral *geniculate* body, Thalamic reticular nucleus, Hypothalamus, limbic system, HPA axis, preoptic area, Medial preoptic nucleus, Suprachiasmatic nucleus, Paraventricular nucleus, Supraoptic nucleusm Anterior hypothalamic nucleus, Lateral preoptic nucleus, median preoptic nucleus, periventricular preoptic nucleus, Tuberal, Dorsomedial hypothalamic nucleus, Ventromedial nucleus, Arcuate nucleus, Lateral area, Tuberal part of Lateral nucleus, Lateral tuberal nuclei, Mammillary nuclei, Posterior nucleus, Lateral area, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, Subthalamus, Subthalamic nucleus, Zona incerta, Pituitary gland, neurohypophysis, Pars *intermedia*, adenohypophysis, cerebral hemispheres, Corona *radiata*, Internal capsule, External capsule, Extreme capsule, Arcuate fasciculus, Uncinate fasciculus, Perforant Path, Hippocampus, Dentate gyms, Cornu ammonis, Cornu ammonis area 1, Cornu ammonis area 2, Cornu ammonis area 3, Cornu ammonis area 4, Amygdala, Central nucleus, Medial nucleus (accessory olfactory system), Cortical and b asom edi al nuclei, Lateral and basolateral nuclei, extended amygdala, Stria terminalis, Bed nucleus of the stria terminalis, Claustrum, Basal ganglia, Striatum, Dorsal striatum (aka neostriatum), Putamen, Caudate nucleus, Ventral striatum, Striatum, Nucleus accumbens, Olfactory tubercle, Globus pallidus, Subthalamic nucleus, Basal forebrain, Anterior perforated substance, Substantia innominata, Nucleus basalis, Diagonal band of Broca, Septal nuclei, Medial septal nuclei, Lamina terminalis, Vascular organ of lamina terminalis, Olfactory bulb, Piriform cortex, Anterior olfactory nucleus, Olfactory tract, Anterior commissure, Uncus, Cerebral cortex, Frontal lobe, Frontal cortex, Primary motor cortex, Supplementary motor cortex, Premotor cortex, Prefrontal cortex, frontopolar cortex, Orbitofrontal cortex, Dorsolateral prefrontal cortex, dorsomedial prefrontal cortex, ventrolateral prefrontal cortex, Superior frontal gyms, Middle frontal gyms, Inferior frontal gyms, Brodmann areas (4, 6, 8, 9, 10, 11, 12, 24, 25, 32, 33, 44, 45, 46, and/or 47), Parietal lobe, Parietal cortex, Primary somatosensory cortex (51), Secondary somatosensory cortex (S2), Posterior parietal cortex, postcentral gyms, precuneus, Brodmann areas (1, 2, 3 (Primary somesthetic area), 5, 7, 23, 26, 29, 31, 39, and/or 40), Occipital lobe, Primary visual cortex (V1), V2, V3, V4, V5/MT, Lateral occipital gyms, Cuneus, Brodmann areas (17 (V1, primary visual cortex), 18, and/or 19), temporal lobe, Primary auditory cortex (A1), secondary auditory cortex (A2), Inferior temporal cortex, Posterior inferior temporal cortex, Superior temporal gyms, Middle temporal gyms, Inferior temporal gyms, Entorhinal Cortex, Perirhinal Cortex, Parahippocampal gyms, Fusiform gyms, Brodmann areas (9, 20, 21, 22, 27, 34, 35, 36, 37, 38, 41, and/or 42), Medial superior temporal area (MST), insular cortex, cingulate cortex, Anterior cingulate, Posterior cingulate, dorsal cingulate, Retrosplenial cortex, Indusium *griseum*, Subgenual area 25, Brodmann areas (23, 24; 26, 29, 30 (retrosplenial areas), 31, and/or 32), cranial nerves (Olfactory (I), Optic (II), Oculomotor (III), Trochlear (IV), Trigeminal (V), Abducens (VI), Facial (VII), Vestibulocochlear (VIII), Glossopharyngeal (IX), Vagus (X), Accessory (XI), Hypoglossal (XII)), or any combination thereof. In some embodiments, the brain region comprises neural pathways Superior longitudinal fasciculus, Arcuate fasciculus, Thalamocortical radiations, Cerebral peduncle, Corpus callosum, Posterior commissure, Pyramidal or corticospinal tract, Medial longitudinal fasciculus, dopamine system, Mesocortical pathway, Mesolimbic pathway, Nigrostriatal pathway, Tuberoinfundibular pathway, serotonin system, Norepinephrine Pathways, Posterior column-medial lemniscus pathway, Spinothalamic tract, Lateral spinothalamic tract, Anterior spinothalamic tract, or any combination thereof.

Disclosed herein include compositions. In some embodiments, the composition comprises: (i) a programmable nuclease or a nucleic acid encoding the programmable nuclease; (ii) a targeting molecule or a nucleic acid encoding the targeting molecule, and/or (iii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, and wherein the targeting molecule is complementary to the recognition site.

Disclosed herein include compositions. In some embodiments, the composition comprises: (i) a programmable nuclease or a nucleic acid encoding the programmable nuclease, wherein the programmable nuclease comprises a zinc finger nuclease (ZFN) and/or transcription activator-like effector nuclease (TALEN); and/or (ii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element.

In some embodiments, a cell of a subject comprises a target gene differentially expressed in a unique cell type and/or in a cell during a unique cell state, wherein the target gene comprises an intron comprising the recognition site. In some embodiments, the programmable nuclease is capable of cleaving the recognition site, whereby the donor nucleic acid is capable of being incorporated into the intron through non-homologous end joining (NHEJ)-dependent DNA repair. In some embodiments, the donor nucleic acid comprises a translation frame linker. In some embodiments, the donor nucleic acid comprises the structure 5'-[recognition site]-[splice acceptor site]-[translation frame linker]-[self-cleaving peptide sequence]-[effector gene]-3'. In some embodiments, the donor nucleic acid comprises the target gene coding sequence downstream of the intron. In some embodiments, the donor nucleic acid comprises the structure 5'-[recognition site]-[splice acceptor site]-[target gene coding sequence downstream of the intron]-[self-cleaving peptide sequence]-[effector gene]-3'. In some embodiments, the donor nucleic acid does not comprise a transcript stabilization element. In some embodiments, the donor nucleic acid comprises a transcript stabilization element. The donor nucleic acid can comprise the structure 5'-[recognition site]-[splice acceptor site]-[translation frame linker]-[self-cleaving peptide sequence]-[effector gene]-[transcript stabilization element]-3'. The donor nucleic acid can comprise the structure 5'-[recognition site]-[splice acceptor site]-[target gene coding sequence downstream of the intron]-[self-cleaving peptide sequence]-[transcript stabilization element]-3'. In some embodiments, the recognition site of the donor nucleic acid and the recognition site of the intron are the same. In some embodiments, the recognition site of the donor nucleic acid and the recognition site of the intron share at least 70 percent sequence identity. In some embodiments, the recognition site does not exist after the donor nucleic acid has been properly incorporated into the intron. In some embodiments, the donor nucleic acid does not comprise a promoter.

In some embodiments, the effector gene is not expressed in a cell other than the unique cell type. In some embodiments, the expression of the effector gene in a cell other than the unique cell type is less than about 5 percent of the expression of the effector gene in the unique cell type. In some embodiments, the unique cell type comprises a unique gene expression pattern. In some embodiments, the unique cell type comprises a unique anatomic location. In some embodiments, the unique cell type comprises anatomically locally unique gene expression. In some embodiments, the effector gene is not expressed in a cell other than in a cell during the unique cell state. In some embodiments, the expression of the effector gene in a cell not in the unique cell state is less than about 10 percent of the expression of the effector gene in a cell during the unique cell state. In some embodiments, the effector gene is only expressed in a cell expressing the target gene. In some embodiments, the expression of the effector gene in a cell that does not express the target gene is less than about 5 percent of the expression of the effector gene in a cell that does express the target gene. In some embodiments, the unique cell state is caused by hereditable, environmental, and/or idiopathic factors.

In some embodiments, the cell comprises a plurality of cells. In some embodiments, the donor nucleic acid is capable of being incorporated into the intron of a post-mitotic cell. In some embodiments, the cell is a dividing cell, a non-dividing cell, a post-mitotic cell, or any combination thereof. In some embodiments, the cell is not in G2/M phase. In some embodiments, the cell is a eukaryotic cell. In some embodiments, the eukaryotic cell comprises an immune cell, a muscle cell, an epithelial cell, an endothelial cell, a neuron, a stem cell, or any combination thereof. In some embodiments, the immune cell comprises a T cell, a B cell, a natural killer cell, a monocyte, a macrophage cell, a dendritic cell, or any combination thereof. In some embodiments, the stem cell comprises an embryonic stem cell, an induced pluripotent stem cell (iPSC), a hematopoietic stem/progenitor cell (HSPC), or any combination thereof. In some embodiments, the cell, the unique cell type and/or the cell in the unique cell state comprises a neuron. In some embodiments, the neuron is: involved in memory expression, involved in eating control, involved in addiction, a component of a motor control circuit, an anxiety processing neuron, an analgesia inducing neuron, an analgesia processing neuron, a pain-processing neuron, or any combination thereof. In some embodiments, the neuron is associated with a neurological disease or disorder. In some embodiments, the neuron can compensate, reverse or alleviate a disorder/disease state. In some embodiments, the unique cell type and/or the cell in the unique cell state causes and/or aggravates a disease or disorder. In some embodiments, the unique cell type and/or the cell in the unique cell state is associated with the pathology of a disease or disorder. In some embodiments, the cell is the cell of a subject.

In some embodiments, the cell is the cell of a subject suffering from a disease or disorder. In some embodiments, the disease or disorder is a blood disease, an immune disease, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or any combination thereof. In some embodiments, the disease or disorder comprises a neurological disease or disorder. In some embodiments, the neurological disease or disorder comprises Alzheimer's disease, Creutzfeld-Jakob's syndrome/disease, bovine spongiform encephalopathy (BSE), prion related infections, diseases involving mitochondrial dysfunction, diseases involving β-amyloid and/or tauopathy, Down's syndrome, hepatic encephalopathy, Huntington's disease, motor neuron diseases, amyotrophic lateral sclerosis (ALS), olivoponto-cerebellar atrophy, post-operative cognitive deficit (POCD), systemic lupus erythematosus, systemic clerosis, Sjogren's syndrome, Neuronal Ceroid Lipofuscinosis, neurodegenerative cerebellar ataxias, Parkinson's disease, Parkinson's dementia, mild cognitive impairment, cognitive deficits in various forms of mild cognitive impairment, cognitive deficits in various forms of dementia, dementia pugilistica, vascular and frontal lobe dementia, cognitive impairment, learning impairment, eye injuries, eye diseases, eye disorders, glaucoma, retinopathy, macular degeneration, head or brain or spinal cord injuries, head or brain or spinal cord trauma, convulsions, epileptic convulsions, epilepsy, temporal lobe epilepsy, myoclonic epilepsy, tinnitus, dyskinesias, chorea, Huntington's chorea, athetosis, dystonia, stereotypy, ballism, tardive dyskinesias, tic disorder, torticollis spasmodicus, blepharospasm, focal and generalized dystonia, nystagmus, hereditary cerebellar ataxias, corticobasal degeneration, tremor, essential tremor, addiction, anxiety disorders, panic disorders, social anxiety disorder (SAD), attention deficit hyperactivity disorder (ADHD), attention deficit syndrome (ADS), restless leg syndrome (RLS), hyperactivity in children, autism, dementia, dementia in Alzheimer's disease, dementia in Korsakoff syndrome, Korsakoff syndrome, vascular dementia, dementia related to HIV infections, HIV-1 encephalopathy, AIDS encephalopathy, AIDS dementia complex, AIDS-related dementia, major depressive disorder, major depression, depression, memory loss, stress, bipolar manic-depressive disorder, drug tolerance, drug tolerance to opioids, movement disorders, fragile-X syndrome, irritable bowel syndrome (IBS), migraine, multiple sclerosis (MS), muscle spasms, pain, chronic pain, acute pain, inflammatory pain, neuropathic pain, posttraumatic stress disorder (PTSD), schizophrenia, spasticity, Tourette's syndrome, eating disorders, food addiction, binge eating disorders, agoraphobia, generalized anxiety disorder, obsessive-compulsive disorder, panic disorder, social phobia, phobic disorders, substance-induced anxiety disorder, delusional disorder, schizoaffective disorder, schizophreniform disorder, substance-induced psychotic disorder, hypertension, or any combination thereof. In some embodiments, the neurological disease or disorder comprises a neuro-psychiatric disorder.

In some embodiments, the neurological disease or disorder comprises pain. In some embodiments, the neurological disease or disorder comprises acute pain and/or chronic pain. In some embodiments, the pain is selected from the group comprising neuropathic pain, allodynia, hyperalgesia, dysesthesia, causalgia, neuralgia, and arthralgia. In some embodiments, the pain is associated with cancer, tumor pressure, bone metastasis, chemotherapy peripheral neuropathy, sciatica radiculopathy, lumbar radiculopathy, cervical radiculopathy, failed back surgery syndrome, *piriformis* syndrome, phantom pain, arachnoiditis, fibromyalgia, facet joint mediated pain, sympathetically-mediated pain syndrome, complex regional pain syndromes (crps), sacro-iliac (si) joint mediated pain, meralgia paresthetica, localized myofacial pain syndromes, myofacial trigger points, diffuse myofacial pain syndrome, post-herpetic neuralgia, trigeminal neuralgia, glossopharyngeal neuralgia, post-epesiotomy scar pain, post-hernia repair scar pain, post-surgery scar pain, post-radiotherapy scar pain, vulvodynia, vaginismus, levator ani syndrome, chronic prostatitis, interstitial cystitis, first bite syndrome, rheumatoid arthritis pain, osteoarthritis pain, atypical odontalgia, phantom tooth pain, neuropathic orofacial pain, primary erythermalgia, atypical facial pain, or any combination thereof.

In some embodiments, the expression of the effector gene is capable of modulating cellular membrane potential. In some embodiments, the expression of the effector gene is capable of altering the membrane potential of the cell by depolarizing the cell and/or hyperpolarizing the cell. In some embodiments, the expression of the effector gene is capable of reducing synaptic transmission by at least 10 percent. In some embodiments, the expression of the effector gene is capable of blocking synaptic transmission. In some embodiments, the effector gene comprises Kir2.1. In some embodiments, the expression of the effector gene is capable of blocking synaptic transmission. In some embodiments, the effector gene comprises tetanus toxin (TNT). In some embodiments, the expression of the effector gene is capable of sensitizing the cell to a pharmacological compound, temperature change, or light. In some embodiments, the effector gene comprises a DREADD receptor and/or Channelrhodopsin-2. In some embodiments, the effector gene is capable of sensitizing the cell to a drug and/or to a prodrug. In some embodiments, the effector gene comprises cytosine deaminase and/or uracil phosphoribosyl transferase, and wherein the prodrug comprises 5-fluorocytosine (5-FC). In some embodiments, the effector gene comprises thymidine kinase (TK), and wherein the prodrug comprises ganciclovir. In some embodiments, the effector gene comprises an enzyme, a signal transduction protein, an ion-channel and/or a G-protein coupled receptor (GPCR). In some embodiments, the effector gene encodes a recombinant protein and/or a native protein. In some embodiments, the effector gene is capable of inducing cell death. In some embodiments, the effector gene comprises cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. In some embodiments, the unique cell state comprises a senescent cell state induced by a tumor microenvironment. In some embodiments, the senescent cell state induced by a tumor microenvironment comprises expression of CD57, KRLG1, TIGIT, or any combination thereof. In some embodiments, the effector gene comprises interleukin-12 (IL-12). In some embodiments, the effector gene comprises a diagnostic agent. In some embodiments, the effector gene comprises a diagnostic contrast agent. In some embodiments, the effector gene comprises green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, rsCherry, rsCherryRev, or any combination thereof.

In some embodiments, upon introduction into a cell, the composition achieves an at least 10 percent higher targeting efficiency as compared to a homology directed repair (HDR)-based method. In some embodiments, upon introduction into a cell, the composition achieves an at least 10 percent higher targeting efficiency as compared to a Homology Independent Targeted Integration (HITI)-based method integrating an effector gene into an exon. In some embodiments, the programmable nuclease is capable of inducing a double-stranded DNA break. In some embodiments, the programmable nuclease comprises Streptococcus pyogenes Cas9 (SpCas9) and/or Staphylococcus aureus Cas9 (SaCas9). In some embodiments, the programmable nuclease comprises Cas1, Cas1B, Cas2, Cas3, Cas4, Cas5, Cash, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpfl, C2c1, C2c3, Cas12a, Cas12b, Cas12c, Cas12d, Cas12e, Cas13a, Cas13b, Cas13c, derivatives thereof, or any combination thereof. In some embodiments, the programmable nuclease comprises a zinc finger nuclease, TAL effector nuclease, meganuclease, MegaTAL, Tev-m TALEN, MegaTev, homing endonuclease, derivatives thereof, or any combination thereof.

In some embodiments, the self-cleaving peptide sequence comprises porcine teschovirus-1 2A peptide (P2A), Thosea asigna virus 2A peptide (T2A), equine rhinitis A virus 2A peptide (E2A), foot-and-mouth disease virus 2A peptide (F2A), or any combination thereof. In some embodiments, the transcript stabilization element is capable of enhancing the stability of a transcript of the effector gene. In some embodiments, the transcript stabilization element comprises woodchuck hepatitis post-translational regulatory element (WPRE), bovine growth hormone polyadenylation (bGH-polyA) signal sequence, human growth hormone polyadenylation (hGH-polyA) signal sequence, or any combination thereof. In some embodiments, the splice acceptor site is capable of being recognized and cleaved by a spliceosome. In some embodiments, the splice acceptor site comprises a branchpoint, a polypyrimidine tract, a 3' splice site, or any combination thereof. In some embodiments, the translation frame linker comprises between about 1 nucleotide and about 10 nucleotides and ensures that the effector gene is expressed in frame with the preceding exon of the target gene. In some embodiments, the translation frame linker places the effector gene in translational frame with the preceding exon of the target gene. In some embodiments, the recognition site is adjacent to a protospacer adjacent motif (PAM) capable of being recognized by the programmable nuclease. In some embodiments, the targeting molecule is capable of associating with the programmable nuclease. In some embodiments, the targeting molecule comprises single strand DNA or single strand RNA. In some embodiments, the targeting molecule comprises a single guide RNA (sgRNA). In some embodiments, the targeting molecule comprises a synthetic nucleic acid.

In some embodiments, the programmable nuclease, the targeting molecule, and/or the donor nucleic acid are encoded on the same nucleic acid. In some embodiments, the programmable nuclease, the targeting molecule, and/or the donor nucleic acid are encoded on different nucleic acids. In some embodiments, the nucleic acid encoding the programmable nuclease, the nucleic acid encoding the targeting molecule, and/or the nucleic acid encoding the donor nucleic acid comprise DNA and/or RNA. In some embodiments, the nucleic acid encoding the programmable nuclease, the nucleic acid encoding the targeting molecule, and/or the nucleic acid encoding the donor nucleic acid are component of a vector. In some embodiments, the vector is an AAV vector, a lentivirus, an integration-deficient lentivirus (IDLV), a plasmid vector, a naked DNA vector, a lipid nanoparticle, or any combination thereof. In some embodiments, the plasmid vector comprises a minicircle plasmid. In some embodiments, the AAV vector comprises AAV1, AAV2, AAV3, AAV4, AAV5, AAV6, AAV7, AAV8, AAV9, or any combination thereof. In some embodiments, the vector is a neurotropic viral vector. In some embodiments, the neurotropic viral vector comprises or is derived from Herpesviridae, varicella zoster virus, pseudorabies virus, cyromegalovirus, Epstein-barr virus, encephalitis virus, polio virus, coxsackie virus, echo virus, mumps virus, measles virus, rabies virus, or any combination thereof. In some embodiments, the vector comprises a heterologous promoter that drives expression of the programmable nuclease, the targeting molecule, and/or the donor nucleic acid. In some embodiments, the heterologous promoter is an inducible promoter. In some embodiments, (i), (ii), and/or (iii) are a component of a ribonucleoprotein (RNP) complex.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 7A-7B depict data related to cell targeting efficiency of Tubb3-expressing neurons with in vivo gene editing based effector gene knock-in.

DETAILED DESCRIPTION

Figure 1:
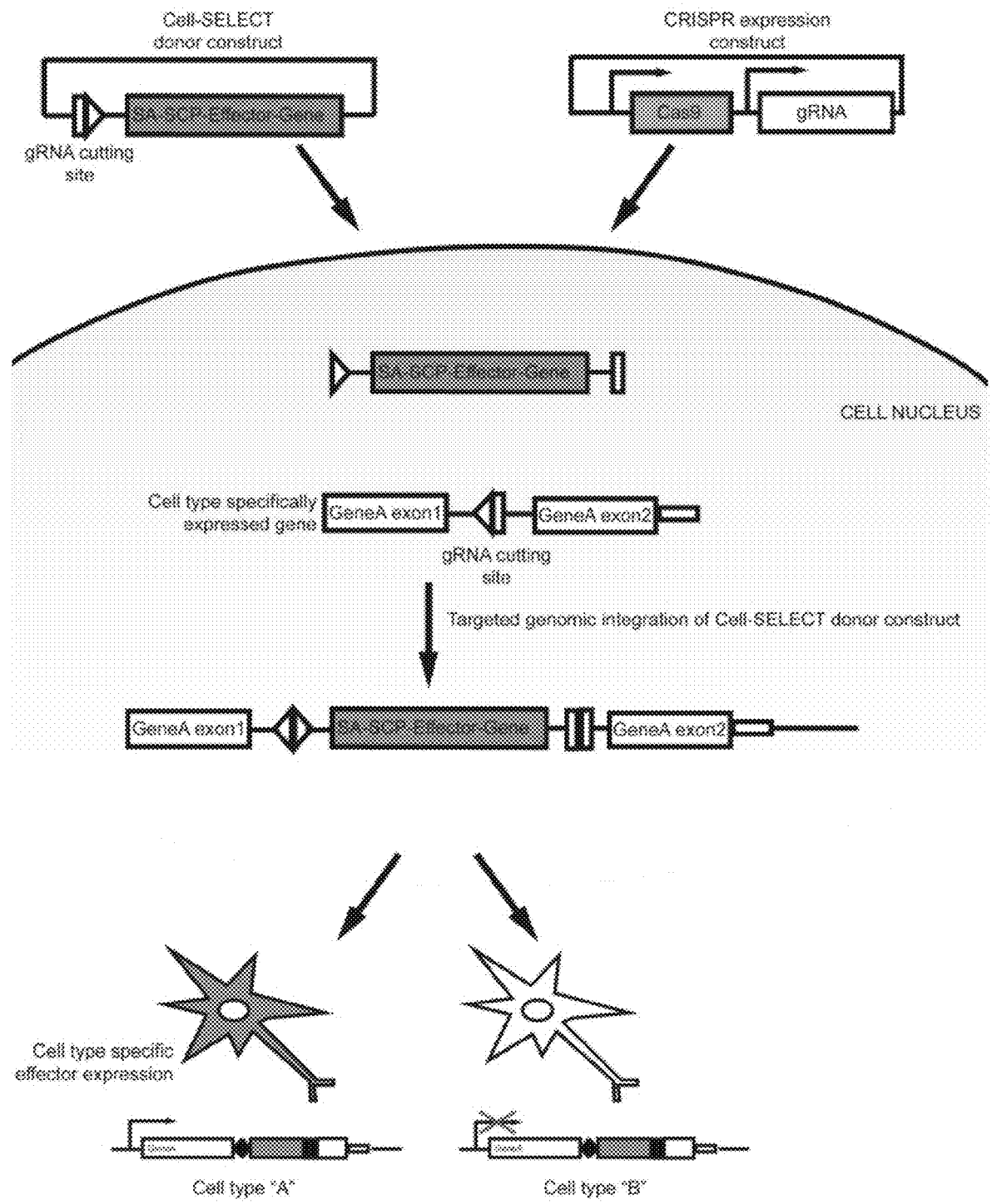
FIG. 1 shows a non-limiting exemplary schematic illustration of the Cell-SELECT method for cell-type-specific expression of effector genes.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include methods of incorporating an effector gene into the genome of a cell. In some embodiments, the method comprises: introducing into a cell: (i) a programmable nuclease or a nucleic acid encoding the programmable nuclease; (ii) a targeting molecule or a nucleic acid encoding the targeting molecule, and (iii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, wherein the cell comprises a target gene differentially expressed in a unique cell type and/or in a cell during a unique cell state, wherein the target gene comprises an intron comprising the recognition site, and wherein the targeting molecule is complementary to the recognition site and the programmable nuclease is capable of cleaving the recognition site, whereby the donor nucleic acid is capable of being incorporated into the intron through non-homologous end joining (NHEJ)-dependent DNA repair.

Disclosed herein include methods of incorporating an effector gene into the genome of a cell. In some embodiments, the method comprises: introducing into a cell: (i) a programmable nuclease or a nucleic acid encoding the programmable nuclease, wherein the programmable nuclease comprises a zinc finger nuclease (ZFN) and/or transcription activator-like effector nuclease (TALEN); and (ii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, wherein the cell comprises a target gene differentially expressed in a unique cell type and/or in a cell during a unique cell state, wherein the target gene comprises an intron comprising the recognition site, and wherein the programmable nuclease is capable of cleaving the recognition site, whereby the donor nucleic acid is capable of being incorporated into the intron through non-homologous end joining (NHEJ)-dependent DNA repair.

Disclosed herein include methods of treating a disease or disorder in a subject. In some embodiments, the method comprises: introducing into a cell of a subject in need thereof: (i) a programmable nuclease or a nucleic acid encoding the programmable nuclease; (ii) a targeting molecule or a nucleic acid encoding the targeting molecule, and (iii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, wherein the cell comprises a target gene differentially expressed in a unique cell type and/or in a cell during a unique cell state, wherein the target gene comprises an intron comprising the recognition site, and wherein the targeting molecule is complementary to the recognition site and programmable nuclease is capable of cleaving the recognition site, whereby the donor nucleic acid is capable of being incorporated into the intron through non-homologous end joining (NHEJ)-dependent DNA repair, and thereby the introducing treats the disease or disorder in the subject.

Disclosed herein include methods of treating a disease or disorder in a subject. In some embodiments, the method comprises: introducing into a cell of a subject in need thereof: (i) a programmable nuclease or a nucleic acid encoding the programmable nuclease, wherein the programmable nuclease comprises a zinc finger nuclease (ZFN) and/or transcription activator-like effector nuclease (TALEN); and (ii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, wherein the cell comprises a target gene differentially expressed in a unique cell type and/or in a cell during a unique cell state, wherein the target gene comprises an intron comprising the recognition site, and wherein the programmable nuclease is capable of cleaving the recognition site, whereby the donor nucleic acid is capable of being incorporated into the intron through non-homologous end joining (NHEJ)-dependent DNA repair, and thereby the introducing treats the disease or disorder in the subject.

Disclosed herein include compositions. In some embodiments, the composition comprises: (i) a programmable nuclease or a nucleic acid encoding the programmable nuclease; (ii) a targeting molecule or a nucleic acid encoding the targeting molecule, and/or (iii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element, and wherein the targeting molecule is complementary to the recognition site.

Disclosed herein include compositions. In some embodiments, the composition comprises: (i) a programmable nuclease or a nucleic acid encoding the programmable nuclease, wherein the programmable nuclease comprises a zinc finger nuclease (ZFN) and/or transcription activator-like effector nuclease (TALEN); and/or (ii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "vector" shall be given its ordinary meaning, and shall also refer to a polynucleotide construct, typically a plasmid or a virus, used to transmit genetic material to a host cell (e.g., a target cell). Vectors can be, for example, viruses, plasmids, cosmids, or phage. A vector can be a viral vector. A vector can be a ribonucleoprotein (RNP) complex. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, can refer to a recombinant nucleic acid that has been generated for the purpose of the expression of a specific nucleotide sequence(s), or that is to be used in the construction of other recombinant nucleotide sequences.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The terms "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see e.g., Lewin, "Genes V" (Oxford University Press, Oxford) pages 847-873). Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, self-cleaving peptide sequences or elements (e.g., 2A sequences) shall be given their ordinary meaning and shall also refer to small peptides introduced as a linker between two polypeptides, allowing autonomous intraribosomal self-processing of polyproteins (See e.g., de Felipe. Genetic Vaccines and Ther. 2:13 (2004); de Felipe et al. Traffic 5:616-626 (2004)). Many 2A elements are known in the art. Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine teschovirus-1 (P2A).

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

As used herein, the term "variant" refers to a polynucleotide (or polypeptide) having a sequence substantially similar to a reference polynucleotide (or polypeptide). In the case of a polynucleotide, a variant can have deletions, substitutions, additions of one or more nucleotides at the 5' end, 3 end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

As used herein, the term "effective amount" refers to an amount sufficient to effect beneficial or desirable biological and/or clinical results.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, the term "treatment" refers to an intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. The terms "treat" and "treatment" include, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may reduce the level of pain signaling in the subject, thereby to reduce, alleviate, or eradicate the symptom(s) of the disease(s). As used herein, the term "prevention" can refer to any activity that reduces the burden of the individual later exhibiting those pain-related disease symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween, polyethylene glycol (PEG), and Pluronics. Auxiliary, stabilizer, emulsifier, lubricant, binder, pH adjuster controller, isotonic agent and other conventional additives may also be added to the carriers.

Methods and Compositions for Cellular Engineering

Disclosed herein are robust methods and compositions for precise and specific functional manipulation of molecularly distinct cell types and states both in in vitro and in in vivo settings. The disclosed Cell-type control via Splice-capture of Expressed Locus Effector by CRISPR Targeting (Cell-SELECT) methods and compositions can comprise an effective targeted gene knock-in approach that introduces a corrective effector gene into a cell-type-specifically expressed genetic locus and efficiently transcribes it by splicing it to the native transcript (FIG. 1). The provided methods and compositions can either selectively ablate, inactivate, sensitize to novel compounds or otherwise functionally manipulate distinct cell types expressing a given gene and consequently to specifically regulate the physiological function they execute.

A defining feature of a particular cell type or cell state can be the unique set of genes that are expressed by the cell. The disclosed Cell-SELECT technology can take advantage of the genetic programs that are active in the cell and use the cell intrinsic gene regulatory mechanisms to control selective expression of an introduced effector gene in desired cell-types. The Cell-SELECT methods and compositions provided herein can ensure cell-type specific expression of those effector genes by targeted intronic knock-in of the Cell-SELECT donor construct (e.g., donor nucleic acid). The genome integrated donor nucleic acid can capture the splicing machinery during cell-type-specifically expressed gene's transcription and can create a new hybrid transcript that expresses the effector gene in all cells where the target gene is expressed. Thereby, even if the genomic knock-in of the construct occurs in many cells, the effector gene expression is only observable in target cells, where the targeted gene is actively transcribed (FIGS. 1 and 4).

The disclosed Cell-SELECT technology can rely on the cell nuclear transfer one or more of the following components: a) a Cell-SELECT donor construct containing the desired effector gene and functional components interfacing with the cellular splicing machinery; b) Cas9 or other programmable nuclease that induces double stranded breaks in the donor construct as well as the targeted genomic location; c) guide RNA (gRNA) or other nuclease targeting mechanism that determines the target of nuclease activity. The Cell-SELECT donor construct can be knocked into the intronic region of the targeted cell-type-specifically expressed target gene by inducing a double stranded break into the intronic area by Cas9 and respective gRNA complex. The donor construct, that can also get cut and linearized by the Cas9/gRNA complex, can get integrated into the target gene's intron by virtue of non-homologous-end-joining (NHEJ) dependent DNA repair mechanism, that happens efficiently in both dividing as well as non-dividing cells. The right orientation of the integrated donor construct can be ensured by reconstitution of the original gRNA sites if the construct lands in the wrong orientation and hence gets recleaved (FIG. 1).

The splice capture approach implemented by some embodiments of the Cell-SELECT method provided herein can achieve superior efficiency as compared to state-of-the-art gene editing based gene tagging solutions. This makes the final cell type specific expression robust to any imprecisions that commonly accompany NHEJ based DNA repair, variation in Cas9 cleavage and degradation of the donor and genomic regions. This design feature achieves several fold higher cell targeting efficiencies as compared to currently available solutions (FIG. 6). Importantly, this efficiency gain enables the use of Cell-SELECT based cell-type-specific functional targeting solutions for practically useful in vivo therapeutic and tissue engineering applications in non-transgenic adult organisms (FIGS. 6-7). A challenge for cell type specific therapies is the achievement of high specificity and low off-target expression of effector proteins. In some embodiments, the Cell-SELECT methods can be employed for controlling the mammalian pain system.

In some embodiments, the disclosed Cell-SELECT compositions and methods achieves cell-type specific expression of effector genes by targeted intronic knock-in of a Cell-SELECT donor construct (e.g., donor nucleic acid). The genome integrated donor can capture the splicing machinery during cell-type-specifically expressed gene's transcription and can create a new hybrid transcript that expresses the effector gene in all cells where the target gene is expressed. Thereby, even though the genomic knock-in of the construct can occur in many cells (e.g., both target and non-target cells), the effector gene expression is only observable in target cells, where the targeted gene is actively transcribed (FIGS. 1 and 4). The methods and compositions provided herein yield cell-type-specific functional targeting solutions for practically useful in vivo therapeutic and tissue engineering applications in non-transgenic adult organisms.

Provided herein are compositions and methods for the delivery of both the donor and gene editing nuclease and nuclease guiding sequences (e.g., gRNA). The Cell-SELECT components disclosed herein can be introduced to the target tissue or biological systems through non-viral methods in the form of proteins, RNA or DNA for the gene editing machinery and DNA template for the donor. Cell-SELECT components can also be delivered through viral vectors, encoded by the viral genomes. In some embodiments, the disclosed Cell-SELECT approach of using cell intrinsic transcription regulatory regions to ensure cell-type-specific expression of the effector gene obviates the need to co-deliver gene regulatory regions, that are often size limiting for viral vectors and frequently for non-viral delivery routes as well.

With the recent advent of high throughput technologies for profiling gene expression in single cells our ability to identify the genetic basis of cell types and states has dramatically improved. Cell-SELECT technologies herein disclosed provides an easily deployable strategy to use these cell type and state defining genetic programs to gain functional control over the vast majority of cells in any organism. The disclosed Cell-SELECT approach overcomes the limited efficiency issues of somatic knock-in technologies making it an attractive avenue for live tissue engineering at cell-type resolution. The Cell-SELECT methods and compositions provided herein can comprise one or more of the following elements to enable cell-type-specific expression of desired effector genes through gene editing: (1) a Cell-SELECT knock-in donor construct; (2) programmable gene editing reagents (e.g., gRNA or other nuclease targeting mechanism and/or Cas9 or other programmable nuclease); and (3) delivery reagents (e.g., vectors).

The Cell-SELECT methods and compositions provided herein can be used to functionally manipulate any cell type or cell state of interest if it has at least one transcribed gene that differentiates it from other physically adjacent cell types. This is highly desirable for many tissues, where cells mediating disparate functions are physically tightly intermingled (e.g. subtypes of neurons mediating breathing, eating and pain functions in the mammalian brainstem or different functional immune cell states in a malignant tumor). Furthermore, Cell-SELECT can be used for functional correction or reprogramming of specific cell types in both genetic as well as non-heritable diseases.

FIG. 1 shows a non-limiting exemplary schematic illustration of the Cell-SELECT method for cell-type-specific expression of effector genes. The gene editing reagents (e.g., gRNA and Cas9 or other programmable nuclease) as well as the Cell-SELECT donor construct carrying the effector gene/genes can be introduced to the cell through viral or non-viral methods. gRNA-guided Cas9 can cleave both the target region in the genome as well as linearize the Cell-SELECT donor construct. The donor construct can become incorporated to the cleaved target region in the genome through non-homologous end joining (NHEJ) dependent DNA repair mechanism. The target regions can be in the intronic regions of cell-type-specifically expressed genes (here Gene A is selectively expressed in cell type A but not in cell type B). After the knock-in of the Cell-SELECT construct the effector gene can be exclusively expressed in cell type A by getting spliced to an exon of the actively transcribed Gene through its splice acceptor site. There can be no expression of the effector gene in cell type B as the targeted gene is not actively transcribed (gRNA, guide RNA; SA, splice acceptor; SCP, self-cleaving peptide sequence).

Emerging cellular profiling technologies have revealed a rich diversity of molecularly defined cell types in multiple organs including blood, immune system and the brain. As most disease conditions only affect one or just a few cell types in the body, precision therapies correcting a particular cell type have become a highly attractive avenue for therapeutic intervention. While performing cell type specific therapies in self renewing tissues such as the immune system has led to a plethora of transformative treatments, achieving the same in non-regenerating nervous system has not previously been feasible. The present disclosure provides Cell-type control via Splice-capture of Expressed Locus Effector by CRISPR Targeting (Cell-SELECT) methods and compositions for efficient targeted knock-in in both dividing and non-dividing cells for precise and specific functional manipulation of molecularly distinct cell types. The disclosed methods and compositions provide a means to activate and inactivate desired cell populations without using genetically modified animals. The methods and compositions provided herein enable cell-type-specific therapies for human brain disorders. Recent advances in high throughput single cell technologies have revealed a few thousand molecular cell types in the nervous system that mediate all aspects of brain function. Importantly, the majority of neurological disorders ranging from chronic pain and addiction to hypertension and others are the consequence of deficits in only a tiny fraction of these neuron types. A key challenge therefore in experimental models of neurological disease as well as clinical translation is to gain selective functional control over the defective circuit nodes and limit the corrective manipulation to the problematic cell type.

Figure 2:
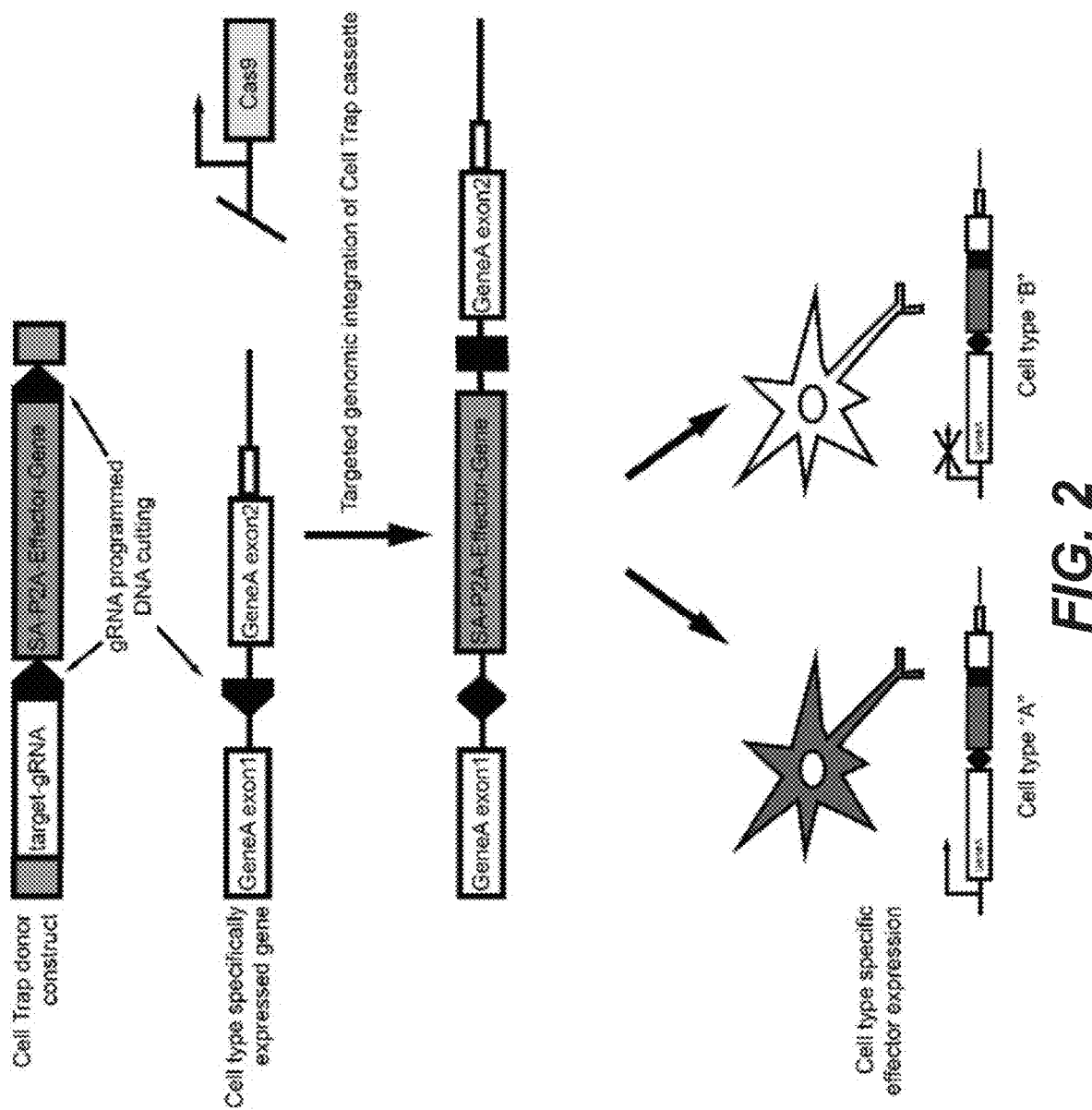
FIG. 2 shows a non-limiting exemplary schematic illustration of the Cell-SELECT methods and compositions provided herein.

Provided herein are Cell-SELECT methods and compositions for precise and specific functional manipulation of molecularly distinct cell types in the brain by tapping into the transcriptional machinery that defines the molecular identity of the neuron. Disclosed herein includes an in vivo gene editing approach to introduce a corrective effector gene into a cell type specifically expressed genetic locus and transcribe it by splicing it to the native transcript (FIG. 2). This approach, in some embodiments, enables a user to either selectively ablate, silence or activate distinct neuron types expressing a given gene and consequently to specifically regulate the behavioral/physiological function they execute. An in vivo gene editing known as Homology Independent Targeted Integration (HITI) CRISPR that allows for high fidelity (up to ~60%) targeted genomic knock-ins of long DNA fragments in adult neural tissue. The compositions and methods provided herein allow delivery of the disclosed Cell-SELECT constructs to any genomic locus and consequently functionally target the vast majority of cell types in the brain that to date have not been selectively targetable by transgenic organism independent technology. Importantly, the disclosed methods and compositions can be applied as is to non-transgenic animals and enables clinical applications for precision in situ circuit engineering in the brain. In some embodiments, the Cell-SELECT technology disclosed herein is employed to gain functional control over the mammalian pain system. FIG. 2 shows a non-limiting exemplary schematic illustration of the Cell-SELECT methods and compositions provided herein. The Cell Trap method can employ in vivo gene editing for cell-type-specific expression of effector proteins. Cas9 as well as the Cell Trap donor construct can be delivered with an AAV viral vector. Guide RNA can cut the target locus (Gene A intron) in the genome as well as the donor nucleic acid (donor insert), which can get integrated to the genome by non-homology dependent DNA repair. As Gene A is selectively expressed in Cell type "A" but not "B", the Cell Trap effector gene (transgene) will only be expressed in Cell Type "A" (gRNA, guide RNA; SA, splice acceptor; P2A, self-cleaving peptide sequence).

There are provided, in some embodiments, methods and compositions for incorporating an effector gene into the genome of a cell. The method can comprise introducing into a cell: (i) a programmable nuclease or a nucleic acid encoding the programmable nuclease; (ii) a targeting molecule or a nucleic acid encoding the targeting molecule, and (iii) a donor nucleic acid or a nucleic acid encoding the donor nucleic acid, wherein the donor nucleic acid comprises a recognition site, a splice acceptor site, a self-cleaving peptide sequence, an effector gene, and an optional transcript stabilization element. In some embodiments, the cell comprises a target gene differentially expressed in a unique cell type and/or in a cell during a unique cell state, wherein the target gene comprises an intron comprising the recognition site. In some embodiments, the targeting molecule is complementary to the recognition site and the programmable nuclease is capable of cleaving the recognition site, whereby the donor nucleic acid is capable of being incorporated into the intron through non-homologous end joining (NHEJ)-dependent DNA repair.

There are provided, in some embodiments, methods and compositions for treating a disease or disorder in a subject. The method can comprise introducing into a cell of a subject in need thereof: (i) a programmable nuclease or a nucleic acid encoding the programmable nuclease; (ii) a targeting molecule or a nucleic acid encoding the targeting molecule, and (iii) a donor nucleic acid or a nucleic acid encoding the donor nucleic acid. In some embodiments, the donor nucleic acid comprises a recognition site, a splice acceptor site, a self-cleaving peptide sequence, an effector gene, and an optional transcript stabilization element. In some embodiments, the cell comprises a target gene differentially expressed in a unique cell type and/or in a cell during a unique cell state, wherein the target gene comprises an intron comprising the recognition site. In some embodiments, the targeting molecule is complementary to the recognition site and programmable nuclease is capable of cleaving the recognition site, whereby the donor nucleic acid is capable of being incorporated into the intron through non-homologous end joining (NHEJ)-dependent DNA repair, and thereby the introducing treats the disease or disorder in the subject.

Disclosed herein include compositions. In some embodiments, the composition comprises: (i) a programmable nuclease or a nucleic acid encoding the programmable nuclease; (ii) a targeting molecule or a nucleic acid encoding the targeting molecule, and/or (iii) a donor nucleic acid or a nucleic acid encoding the donor nucleic acid. In some embodiments, the donor nucleic acid comprises a recognition site, a splice acceptor site, a self-cleaving peptide sequence, an effector gene, and an optional transcript stabilization element, and wherein the targeting molecule is complementary to the recognition site. In some embodiments, a cell of a subject comprises a target gene differentially expressed in a unique cell type and/or in a cell during a unique cell state, wherein the target gene comprises an intron comprising the recognition site. In some embodiments, the programmable nuclease is capable of cleaving the recognition site, whereby the donor nucleic acid is capable of being incorporated into the intron through non-homologous end joining (NHEJ)-dependent DNA repair.

There are provided, in some embodiments, methods and compositions for incorporating an effector gene into the genome of a cell. The method can comprise introducing into a cell: (i) a programmable nuclease or a nucleic acid encoding the programmable nuclease, wherein the programmable nuclease comprises a zinc finger nuclease (ZFN) and/or transcription activator-like effector nuclease (TALEN); and (ii) a donor nucleic acid or a nucleic acid encoding the donor nucleic acid. In some embodiments, the donor nucleic acid comprises a recognition site, a splice acceptor site, a self-cleaving peptide sequence, an effector gene, and an optional transcript stabilization element. In some embodiments, the cell comprises a target gene differentially expressed in a unique cell type and/or in a cell during a unique cell state, wherein the target gene comprises an intron comprising the recognition site. In some embodiments, the programmable nuclease is capable of cleaving the recognition site, whereby the donor nucleic acid is capable of being incorporated into the intron through non-homologous end joining (NHEJ)-dependent DNA repair.

There are provided, in some embodiments, methods and compositions for treating a disease or disorder in a subject. The method can comprise introducing into a cell of a subject in need thereof: (i) a programmable nuclease or a nucleic acid encoding the programmable nuclease, wherein the programmable nuclease comprises a zinc finger nuclease (ZFN) and/or transcription activator-like effector nuclease (TALEN); and (ii) a donor nucleic acid or a nucleic acid encoding the donor nucleic acid. In some embodiments, the donor nucleic acid comprises a recognition site, a splice acceptor site, a self-cleaving peptide sequence, an effector gene, and an optional transcript stabilization element. In some embodiments, the cell comprises a target gene differentially expressed in a unique cell type and/or in a cell during a unique cell state, wherein the target gene comprises an intron comprising the recognition site. In some embodiments, the programmable nuclease is capable of cleaving the recognition site, whereby the donor nucleic acid is capable of being incorporated into the intron through non-homologous end joining (NHEJ)-dependent DNA repair, and thereby the introducing treats the disease or disorder in the subject.

Disclosed herein include compositions. In some embodiments, the composition comprises: (i) a programmable nuclease or a nucleic acid encoding the programmable nuclease, wherein the programmable nuclease comprises a zinc finger nuclease (ZFN) and/or transcription activator-like effector nuclease (TALEN); and/or (ii) a donor nucleic acid or a nucleic acid encoding the donor nucleic acid. In some embodiments, the donor nucleic acid comprises a recognition site, a splice acceptor site, a self-cleaving peptide sequence, an effector gene, and an optional transcript stabilization element. In some embodiments, a cell of a subject comprises a target gene differentially expressed in a unique cell type and/or in a cell during a unique cell state, wherein the target gene comprises an intron comprising the recognition site. In some embodiments, the programmable nuclease is capable of cleaving the recognition site, whereby the donor nucleic acid is capable of being incorporated into the intron through non-homologous end joining (NHEJ)-dependent DNA repair.

In some embodiments, the method achieves an at least 10% higher targeting efficiency as compared to a homology directed repair (HDR)-based method. The targeting efficiency of the method can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900%, 1000%, or a number or a range between any two of these values, higher than the targeting efficiency of a homology directed repair (HDR)-based method.

In some embodiments, the method achieves an at least 10% higher targeting efficiency as compared to a Homology Independent Targeted Integration (HITI)-based method integrating an effector gene into an exon. The targeting efficiency of the method can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900%, 1000%, or a number or a range between any two of these values, higher than a Homology Independent Targeted Integration (HITI)-based method integrating an effector gene into an exon.

In some embodiments, the effector gene is not expressed in a cell other than the unique cell type. The expression of the effector gene in a cell other than the unique cell type can be less than about 5 percent of the expression of the effector gene in the unique cell type. The unique cell type can comprise a unique gene expression pattern. The unique cell type can comprise a unique anatomic location. The unique cell type can comprise anatomically locally unique gene expression.

In some embodiments, the effector gene is not expressed in a cell other than in a cell during the unique cell state. The expression of the effector gene in a cell not in the unique cell state can be less than about 10% of the expression of the effector gene in a cell during the unique cell state. The expression of the effector gene in a cell not in the unique cell state can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900%, 1000%, or a number or a range between any two of these values, less than the expression of the effector gene in a cell during the unique cell state. In some embodiments, the effector gene is only expressed in a cell expressing the target gene. The expression of the effector gene in a cell that does not express the target gene can be less than about 5 percent of the expression of the effector gene in a cell that does express the target gene. The expression of the effector gene in a cell that does not express the target gene can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900%, 1000%, or a number or a range between any two of these values, less than the expression of the effector gene in a cell that does express the target gene. The unique cell state can be caused by hereditable, environmental, and/or idiopathic factors.

In some embodiments the target gene is a protein-encoding gene. In some embodiments the target gene is a not a protein-encoding gene. The target gene can have one or more introns. The target gene may or may not have an intron. In some embodiments, the target gene is a long noncoding RNA (lncRNA). In some embodiments, the donor nucleic acid is integrated into the target gene in both desired cells (e.g., a unique cell type and/or a cell in a unique cell state) as well as non-desired cells (e.g., cells other than a unique cell type or a cell in a unique cell state). In some such embodiments, the effector gene is expressed in the desired cells (e.g., a unique cell type and/or a cell in a unique cell state) expressing the targeted gene. In some embodiments, non-desired cells (e.g., cells other than a unique cell type or a cell in a unique cell state) do not express the target gene, and therefore the effector gene will be dormant (e.g., not expressed).

The cell can comprise a plurality of cells. The donor nucleic acid can be capable of being incorporated into the intron of a post-mitotic cell. The cell can be a dividing cell, a non-dividing cell, a post-mitotic cell, or any combination thereof. In some embodiments, the cell is not in G2/M phase. The cell can be a eukaryotic cell (e.g., an immune cell, an epithelial cell, a muscle cell, an endothelial cell, a neuron, a stem cell, or any combination thereof). The immune cell can comprise a T cell, a B cell, a natural killer cell, a monocyte, a macrophage cell, a dendritic cell, or any combination thereof. The stem cell can comprise an embryonic stem cell, an induced pluripotent stem cell (iPSC), a hematopoietic stem/progenitor cell (HSPC), or any combination thereof. The cell can be a germline cell or a somatic cell. Exemplary cells contemplated as described herein, include, a bacterial cell; an archaeal cell; a single-celled eukaryotic organism; a plant cell; an algal cell; a fungal cell; an animal cell; a cell from an invertebrate animal (e.g., an insect, a cnidarian, an echinoderm, a nematode, etc.); a eukaryotic parasite (e.g., a malarial parasite, e.g., *Plasmodium falciparum*; a helminth; etc.); a cell from a vertebrate animal (e.g., fish, amphibian, reptile, bird, mammal); a mammalian cell, e.g., a rodent cell, a human cell, a non-human primate cell. Suitable host cells include naturally occurring cells; genetically modified cells (e.g., cells genetically modified in a laboratory, e.g., by the "hand of man"); and cells manipulated in vitro in any way.

Effector Genes

The cell type specific functional manipulations disclosed herein can depend on the effector gene carried by the Cell-SELECT donor construct (e.g., donor nucleic acid). The effector genes that can be introduced to the cell through the Cell-SELECT method include, but are not limited to, fluorescent or other contrast generating protein encoding genes (e.g. Gfp, mCherry), cell apoptosis triggering genes (e.g. Casp3), particular cell-type function regulating genes (e.g. ion channels, GPCR-s, enzymes etc.) or any other recombinant protein. The expression of the effector gene can be capable of modulating cellular membrane potential. The expression of the effector gene can be capable of altering the membrane potential of the cell by depolarizing the cell and/or hyperpolarizing the cell. The expression of the effector gene can be capable of reducing synaptic transmission by at least 10 percent. The expression of the effector gene can be capable of blocking synaptic transmission. The effector gene can comprise Kir2.1. The expression of the effector gene can be capable of blocking synaptic transmission. The effector gene can comprise tetanus toxin (TNT). The expression of the effector gene can be capable of sensitizing the cell to a pharmacological compound, temperature change, or light. The effector gene can comprise a DREADD receptor and/or Channelrhodopsin-2. The effector gene can be capable of sensitizing the cell to a drug and/or to a prodrug. The effector gene can comprise cytosine deaminase and/or uracil phosphoribosyl transferase and the prodrug can comprise 5-fluorocytosine (5-FC). The effector gene can comprise thymidine kinase (TK), and wherein the prodrug can comprise ganciclovir. The effector gene can comprise an enzyme, a signal transduction protein, an ion-channel and/or a G-protein coupled receptor (GPCR). In some embodiments, the effector gene encodes a recombinant protein and/or a native protein. The effector gene can be capable of inducing cell death. The effector gene can comprise cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof. The unique cell state can comprise a senescent cell state induced by a tumor microenvironment. The senescent cell state induced by a tumor microenvironment can comprise expression of CD57, KRLG1, TIGIT, or any combination thereof. The effector gene can comprise interleukin-12 (IL-12).

Although chronic control of cellular function can be easiest to achieve, temporally controlled regulation of neuronal output is often desirable for meaningful neural circuit control. There are provided, in some embodiments, Cell-SELECT compositions and methods, including constructs, to deliver genes that make the cells sensitive to novel pharmacological compounds (using DREADD receptors) or light (implementing Channelrhodopsin 2) to the pain processing neurons in LPBN. There is provided, in some embodiments, a pAAV-CELL-SELECT construct for targeted viral knock-in of optogenetic activatory channelrhodopsin-2 (SEQ ID NO: 3). The effector gene can comprise a H134R mutant of an N-terminal fragment of channelrhodopsin-2 from the alga *C. reinhardtii*. The disclosed methods and compositions can enable pharmacological and/or light control over pain behaviors conditional on external delivery of control agents. In some embodiments, response decay times as well potential habituation effects can be effectively managed for the provided methods. The Cell-SELECT methods can enable precise regulation of local brain function (e.g., gain functional control over cell types in the brain). The disclosed compositions and methods can be modular and easily applicable to control any molecularly distinct neuron type in any neural circuit and importantly also applicable to a clinical setting.

There are provided, in some embodiments, methods and compositions for functional reprogramming of disease-associated cell states in the immune system. The disclosed Cell-SELECT method can be used to functionally reprogram specific cell states in non-genetic diseases that stem from environmental and/or idiopathic factors. For example, T-lymphocytes that have migrated to a malignant tumor can sometimes become senescent and fail to mediate an antitumor response. This senescent cell state can be characterized by the expression of known genetic programs (e.g. expression of CD57, KRLG1, and other genes). This senescent state can be overcome by exposure to cytokines such as interleukin-12 (IL12). A Cell-SELECT-based approach provided herein can be deployed to selectively rescue T-lymphocytes from the senescence by delivering Cell-SELECT donors containing the IL12 gene coding sequence with Cas9 and KRLG1 gene intron targeting gRNA with AAV6 based viral vectors in the tumor environment. This can result in genomic knock-in of IL12 coding sequence to many disparate cell types in the tumor microenvironment. However, IL12 can be selectively be expressed and released from senescent T-lymphocytes that enable them to reactivate their anti-tumor response via autocrine signaling.

In some embodiments, the effector gene encodes a protein of interest. As used herein, a "protein of interest" can be any protein, including naturally-occurring and non-naturally occurring proteins. Examples of protein of interest include, but are not limited to, luciferases; fluorescent proteins (e.g., GFP); growth hormones (GHs) and variants thereof; insulin-like growth factors (IGFs) and variants thereof; granulocyte colony-stimulating factors (G-CSFs) and variants thereof; erythropoietin (EPO) and variants thereof; insulin, such as proinsulin, preproinsulin, insulin, insulin analogs, and the like; antibodies and variants thereof, such as hybrid antibodies, chimeric antibodies, humanized antibodies, monoclonal antibodies; antigen binding fragments of an antibody (Fab fragments), single-chain variable fragments of an antibody (scFV fragments); dystrophin and variants thereof; clotting factors and variants thereof; cystic fibrosis transmembrane conductance regulator (CFTR) and variants thereof; and interferons and variants thereof.

In some embodiments, the protein of interest is a therapeutic protein or variant thereof. Non-limiting examples of therapeutic proteins include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-a), transforming growth factor beta (TGF-β), and the like; soluble receptors, such as soluble TNF-receptors, soluble VEGF receptors, soluble interleukin receptors (e.g., soluble IL-1 receptors and soluble type II IL-1 receptors), soluble γ/δ T cell receptors, ligand-binding fragments of a soluble receptor, and the like; enzymes, such as-glucosidase, imiglucarase, β-glucocerebrosidase, and alglucerase; enzyme activators, such as tissue plasminogen activator; chemokines, such as IP-10, monokine induced by interferon-gamma (Mig), Gro/IL-8, RANTES, MIP-1, MIP-I β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other non-limiting examples of protein of interest include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or mini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

In some embodiments, the protein of interest is an active fragment of a protein, such as any of the proteins disclosed herein. In some embodiments, the protein of interest is a fusion protein comprising some or all of two or more proteins. In some embodiments a fusion protein can comprise all or a portion of any of the aforementioned proteins.

In some embodiments, the method is multiplexed. In some embodiments two or more genetic loci (e.g., introns) are targeted for knock-in. In some such embodiments, all of the target genes are expressed in a unique cell type and/or unique cell state. For example, the method can comprise integrating a first donor nucleic acid (comprising a first effector gene) into an intron of a first target gene and integrating a second donor nucleic acid (comprising a second effector gene) into an intron of a second target gene. The first target gene and the second target gene can be expressed in the same or different unique cell type and/or unique cell state. The first effector gene and the second effector gene can be the same or different. The first effector gene and the second effector gene can encode for two or more proteins of interest. The effector gene can comprise coding regions for two or more proteins of interest. The two or more proteins of interest can be the same or different from each other. In some embodiments, the two or more proteins of interest are related polypeptides, for example neutralizing antibodies for the same virus.

In some embodiments, the protein of interest is a multi-subunit protein. For examples, the protein of interest can comprise two or more subunits, or two or more independent polypeptide chains. In some embodiments, the protein of interest can be an antibody. Examples of antibodies include, but are not limited to, antibodies of various isotypes (for example, IgG1, IgG2, IgG3, IgG4, IgA, IgD, IgE, and IgM); monoclonal antibodies produced by any means known to those skilled in the art, including an antigen-binding fragment of a monoclonal antibody; humanized antibodies; chimeric antibodies; single-chain antibodies; antibody fragments such as Fv, F(ab')2, Fab', Fab, Facb, scFv and the like; provided that the antibody is capable of binding to antigen. In some embodiments, the antibody is a full-length antibody.

In some embodiments, the effector gene encodes a pro-survival protein (e.g., Bcl-2, Bcl-XL, Mcl-1 and A1). In some embodiments, the effector gene encodes a apoptotic factor or apoptosis-related protein such as, for example, AIF, Apaf e.g. Apaf-1, Apaf-2, Apaf-3, oder APO-2 (L), APO-3 (L), Apopain, Bad, Bak, Bax, Bcl-2, Bcl-$x_L$, Bcl-$x_S$, bik, CAD, Calpain, Caspase e.g. Caspase-1, Caspase-2, Caspase-3, Caspase-4, Caspase-5, Caspase-6, Caspase-7, Caspase-8, Caspase-9, Caspase-10, Caspase-11, ced-3, ced-9, c-Jun, c-Myc, crm A, cytochrom C, CdR1, DcR1, DD, DED, DISC, DNA-PKcs, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, Lamin A/B, MAP, MCL-1, Mdm-2, MEKK-1, MORT-1, NEDD, NF-kappaB, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, and/or transglutaminase.

In some embodiments, the effector gene encodes a cellular reprogramming factor capable of converting an at least partially differentiated cell to a less differentiated cell, such as, for example, Oct-3, Oct-4, Sox2, c-Myc, Klf4, Nanog, Lin28, ASCL1, MYT1 L, TBX3b, SV40 large T, hTERT, miR-291, miR-294, miR-295, or any combinations thereof. In some embodiments, the effector gene encodes a programming factor that is capable of differentiating a given cell into a desired differentiated state, such as, for example, nerve growth factor (NGF), fibroblast growth factor (FGF), interleukin-6 (IL-6), bone morphogenic protein (BMP), neurogenin3 (Ngn3), pancreatic and duodenal homeobox 1 (Pdx1), Mafa, or any combination thereof.

In some embodiments, the effector gene encodes a human adjuvant protein capable of eliciting an innate immune response, such as, for example, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including Clq, MBL, Clr, Cls, C2b, Bb, D, MASP-1, MASP-2, C4b, C3b, C5a, C3a, C4a, C5b, C6, C7, C8, C9, CR1, CR2, CR3, CR4, C1qR, ClINH, C4 bp, MCP, DAF, H, I, P and CD59; from proteins which are components of the signaling networks of the pattern recognition receptors including TLR and IL-1 R1, whereas the components are ligands of the pattern recognition receptors including IL-1 alpha, IL-1 beta, Beta-defensin, heat shock proteins, such as HSP10, HSP60, HSP65, HSP70, HSP75 and HSP90, gp96, Fibrinogen, Typ111 repeat extra domain A of fibronectin; the receptors, including IL-1 RI, TLR1, TLR2, TLR3, TLR4, TLR5, TLR6, TLR7, TLR8, TLR9, TLR10, TLR11; the signal transducers including components of the Small-GTPases signaling (RhoA, Ras, Racl, Cdc42 etc.), components of the PIP signaling (P13K, Src-Kinases, etc.), components of the MyD88-dependent signaling (MyD88, IRAK1, IRAK2, etc.), components of the MyD88-independent signaling (TICAM1, TICAM2, etc.); activated transcription factors including e.g. NF-κB, c-Fos, c-Jun, c-Myc; and induced target genes including e.g. IL-1 alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, flt-3 ligand, thymopentin, Gp96 or fibronectin, or any species homolog of any of the above human adjuvant proteins.

In some embodiments, the effector gene encodes immunogenic material capable of stimulating an immune response (e.g., an adaptive immune response) such as, for example, antigenic peptides or proteins from a pathogen. The expression of the antigen may stimulate the body's adaptive immune system to provide an adaptive immune response. Thus, it is contemplated that some embodiments the Cell-SELECT compositions provided herein can be employed as vaccines for the prophylaxis or treatment of infectious diseases (e.g., as vaccines).

The effector gene can comprise a suicide gene. In some embodiments, the effector gene encodes a protein which, upon administration of a prodrug, causes the death of its host cell (e.g., a suicide gene). In some embodiments, the methods herein comprise a) administering (i) a programmable nuclease or a nucleic acid encoding the programmable nuclease; (ii) a targeting molecule or a nucleic acid encoding the targeting molecule, and/or (iii) a donor nucleic acid or a nucleic acid encoding the donor nucleic acid to a subject comprising the cell and b) administering a prodrug to the subject. Any suitable suicide gene and prodrug is contemplated this disclosure, such as, for example, the suicide gene/prodrug combinations depicted in Table 1.

TABLE 1

| EFFECTOR GENES AND PRODRUGS | |
|---|---|
| Effector (suicide) Gene | Prodrug |
| HSV thymidine kinase (TK) | Ganciclovir (GCV); Ganciclovir elaidic acid ester; Penciclovir (PCV); Acyclovir (ACV); Valacyclovir (VCV); (E)-5-(2-bromovinyl)-2'-deoxyuridine (BVDU); Zidovuline (AZT); 2'-exo-methanocarbathymidine (MCT) |
| Cytosine Deaminase (CD) | 5-fluorocytosine (5-FC) |
| Purine nucleoside phosphorylase (PNP) | 6-methylpurine deoxyriboside (MEP); fludarabine (FAMP) |
| Cytochrome p450 enzymes (CYP) | Cyclophosphamide (CPA); Ifosfamide (IFO); 4-ipomeanol (4-IM) |
| Carboxypeptidases (CP) | 4-[(2-chloroethyl)(2-mesyloxyethyl)amino]benzoyl-L-glutamic acid (CMDA); Hydroxy-and amino-aniline mustards; Anthracycline glutamates; Methotrexate α-peptides (MTX-Phe) |

TABLE 1-continued

EFFECTOR GENES AND PRODRUGS

| Effector (suicide) Gene | Prodrug |
| --- | --- |
| Caspase-9 | AP1903 |
| Carboxylesterase (CE) | Irinotecan (IRT); Anthracycline acetals |
| Nitroreductase (NTR) | dinitroaziridinylbenzamide CB1954; dinitrobenzamide mustard SN23862; 4-Nitrobenzyl carbamates; Quinones |
| Horse radish peroxidase (HRP) | Indole-3-acetic acid (IAA); 5-Fluoroindole-3-acetic acid (FIAA) |
| Guanine Ribosyltransferase (XGRTP) | 6-Thioxanthine (6-TX) |
| Glycosidase enzymes | HM1826; Anthracycline acetals |
| Methionine-α,γ-lyase (MET) | Selenomethionine (SeMET) |
| Thymidine phosphorylase (TP) | 5'-Deoxy-5-fluorouridine (5'-DFU) |

A protein of interest encoded by an effector gene can be of various lengths. For example, the protein of interest can be at least about 200 amino acids, at least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer in length. In some embodiments, the protein of interest is at least about 480 amino acids in length. In some embodiments, the protein of interest is at least about 500 amino acids in length. In some embodiments, the protein of interest is about 750 amino acids in length.

A donor nucleic acid can comprise one effector gene, or more than one effector gene. The effector genes can have different lengths in different implementations. In some embodiments, an effector genes is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, 10000, or a number or a range between any two of these values, nucleotides in length. In some embodiments, an effector gene is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, or 10000 nucleotides in length.

Methods of Diagnosing and Treating Diseases and Disorders

Disclosed herein include methods of treating a disease or disorder. In some embodiments, the unique cell type and/or the cell in the unique cell state causes and/or aggravates a disease or disorder. The unique cell type and/or the cell in the unique cell state can be associated with the pathology of a disease or disorder. The cell can be the cell of a subject. The cell can be the cell of a subject suffering from a disease or disorder. The disease or disorder can be a blood disease, an immune disease, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or any combination thereof. In some embodiments, the unique cell type and/or the cell in the unique cell state causes and/or aggravates a disease or disorder. The unique cell type and/or the cell in the unique cell state can be associated with the pathology of a disease or disorder.

The disease or disorder can comprise a neurological disease or disorder. The cell, the unique cell type and/or the cell in the unique cell state can comprise a neuron. The cell, the unique cell type and/or the cell in the unique cell state can comprise a cell in a brain region. The neuron can be involved in memory expression, involved in eating control, involved in addiction, a component of a motor control circuit, an anxiety processing neuron, an analgesia inducing neuron, an analgesia processing neuron, a pain-processing neuron, or any combination thereof. The neuron can be associated with a neurological disease or disorder. In some embodiments, the neuron can compensate, reverse or alleviate a disorder/disease state. The neurological disease or disorder can comprise Alzheimer's disease, Creutzfeld-Jakob's syndrome/disease, bovine spongiform encephalopathy (BSE), prion related infections, diseases involving mitochondrial dysfunction, diseases involving β-amyloid and/or tauopathy, Down's syndrome, hepatic encephalopathy, Huntington's disease, motor neuron diseases, amyotrophic lateral sclerosis (ALS), olivoponto-cerebellar atrophy, post-operative cognitive deficit (POCD), systemic lupus erythematosus, systemic clerosis, Sjogren's syndrome, Neuronal Ceroid Lipofuscinosis, neurodegenerative cerebellar ataxias, Parkinson's disease, Parkinson's dementia, mild cognitive impairment, cognitive deficits in various forms of mild cognitive impairment, cognitive deficits in various forms of dementia, dementia pugilistica, vascular and frontal lobe dementia, cognitive impairment, learning impairment, eye injuries, eye diseases, eye disorders, glaucoma, retinopathy, macular degeneration, head or brain or spinal cord injuries, head or brain or spinal cord trauma, convulsions, epileptic convulsions, epilepsy, temporal lobe epilepsy, myoclonic epilepsy, tinnitus, dyskinesias, chorea, Huntington's chorea, athetosis, dystonia, stereotypy, ballism, tardive dyskinesias, tic disorder, torticollis spasmodicus, blepharospasm, focal and generalized dystonia, nystagmus, hereditary cerebellar ataxias, corticobasal degeneration, tremor, essential tremor, addiction, anxiety disorders, panic disorders, social anxiety disorder (SAD), attention deficit hyperactivity disorder (ADHD), attention deficit syndrome (ADS), restless leg syndrome (RLS), hyperactivity in children, autism, dementia, dementia in Alzheimer's disease, dementia in Korsakoff syndrome, Korsakoff syndrome, vascular dementia, dementia related to HIV infections, HIV-1 encephalopathy, AIDS encephalopathy, AIDS dementia complex, AIDS-related dementia, major depressive disorder, major depression, depression, memory loss, stress, bipolar manic-depressive disorder, drug tolerance, drug tolerance to opioids, movement disorders, fragile-X syndrome, irritable bowel syndrome (IBS), migraine, multiple sclerosis (MS), muscle spasms, pain, chronic pain, acute pain, inflammatory pain, neuropathic pain, posttraumatic stress disorder (PTSD), schizophrenia, spasticity, Tourette's syndrome, eating disorders, food addiction, binge eating disorders, agoraphobia, generalized anxiety disorder, obsessive-compulsive disorder, panic disorder, social phobia, phobic disorders, substance-induced anxiety disorder, delusional disorder, schizoaffective disorder, schizophreniform disorder, substance-induced psychotic disorder, hypertension, or any combination thereof. The neurological disease or disorder can comprise a neuro-psychiatric disorder.

The neurological disease or disorder can comprise pain (e.g., acute pain and/or chronic pain). The pain can be selected from the group comprising neuropathic pain, allodynia, hyperalgesia, dysesthesia, causalgia, neuralgia, and arthralgia. The pain can be associated with cancer, tumor pressure, bone metastasis, chemotherapy peripheral neuropathy, sciatica radiculopathy, lumbar radiculopathy, cervical radiculopathy, failed back surgery syndrome, *piriformis* syndrome, phantom pain, arachnoiditis, fibromyalgia, facet joint mediated pain, sympathetically-mediated pain syndrome, complex regional pain syndromes (crps), sacroiliac (si) joint mediated pain, meralgia paresthetica, localized myofacial pain syndromes, myofacial trigger points, diffuse myofacial pain syndrome, post-herpetic neuralgia, trigeminal neuralgia, glossopharyngeal neuralgia, post-epesiotomy scar pain, post-hernia repair scar pain, post-surgery scar pain, post-radiotherapy scar pain, vulvodynia, vaginismus, levator ani syndrome, chronic prostatitis, interstitial cystitis, first bite syndrome, rheumatoid arthritis pain, osteoarthritis pain, atypical odontalgia, phantom tooth pain, neuropathic orofacial pain, primary erythermalgia, atypical facial pain, or any combination thereof.

The compositions, systems, and methods described herein can be used to express one or more effector genes in a unique cell type and/or in a cell during a unique cell state to treat, prevent, and/or diagnose various diseases or disorders. Non-limiting examples of the diseases include cancer such as carcinoma, sarcoma, leukemia, lymphoma; and autoimmune diseases such as multiple sclerosis. Non-limiting examples of carcinomas include esophageal carcinoma; hepatocellular carcinoma; basal cell carcinoma, squamous cell carcinoma (various tissues); bladder carcinoma, including transitional cell carcinoma; bronchogenic carcinoma; colon carcinoma; colorectal carcinoma; gastric carcinoma; lung carcinoma, including small cell carcinoma and non-small cell carcinoma of the lung; adrenocortical carcinoma; thyroid carcinoma; pancreatic carcinoma; breast carcinoma; ovarian carcinoma; prostate carcinoma; adenocarcinoma; sweat gland carcinoma; sebaceous gland carcinoma; papillary carcinoma; papillary adenocarcinoma; cystadenocarcinoma; medullary carcinoma; renal cell carcinoma; ductal carcinoma in situ or bile duct carcinoma; choriocarcinoma; seminoma; embryonal carcinoma; Wilm's tumor; cervical carcinoma; uterine carcinoma; testicular carcinoma; osteogenic carcinoma; epithelieal carcinoma; and nasopharyngeal carcinoma. Non-limiting examples of sarcomas include fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas. Non-limiting examples of solid tumors include glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Non-limiting examples of leukemias include chronic myeloproliferative syndromes; acute myelogenous leukemias; chronic lymphocytic leukemias, including B-cell CLL, T-cell CLL prolymphocyte leukemia, and hairy cell leukemia; and acute lymphoblastic leukemias. Examples of lymphomas include, but are not limited to, B-cell lymphomas, such as Burkitt's lymphoma; Hodgkin's lymphoma; and the like. Other non-liming examples of the diseases that can be treated using the Cell-SELECT methods and compositions disclosed herein include genetic disorders including sickle cell anemia, cystic fibrosis, lysosomal acid lipase (LAL) deficiency 1, Tay-Sachs disease, Phenylketonuria, Mucopolysaccharidoses, Glycogen storage diseases (GSD, e.g., GSD types I, II, III, IV, V, VI, VII, VIII, IX, X, XI, XII, XIII, and XIV), Galactosemia, muscular dystrophy (e.g., Duchenne muscular dystrophy), and hemophilia.

Additionally, the Cell-SELECT compositions, systems, and methods provided herein may be used for the diagnosis, treatment, and/or prevention of infectious diseases. As used herein, the term "infectious diseases" refers to diseases caused by any pathogen or agent that infects mammalian cells, preferably human cells and causes a disease condition, such as, for example, bacteria, yeast, fungi, protozoans, *mycoplasma*, viruses, prions, and parasites. Non-limiting examples of infectious diseases include (a) viral diseases such as, for example, diseases resulting from infection by an adenovirus, a herpesvirus (e.g., HSV-i, HSV-II, CMV, or VZV), a poxvirus (e-g~, an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenza virus, mumps virus, measles vims, and respiratory syncytial virus (RSV)), a coronavirus (e.g., SARS, SARS-Cov-2), a papovavirus (e.g., papillomaviruses, such as those that cause genital warts, common warts, or plantar warts), a hepadnavirus (e.g., hepatitis B vims), a flavivirus (e.g., hepatitis C virus or Dengue virus), or a retrovirus (e.g., a lentivirus such as HIV); (b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or Bordeteila; (c) other infectious diseases, such *chlamydia*, fungal diseases including but not limited to candidiasis, aspergillosis, histoplasmosis, cryptococcal meningitis, parasitic diseases including but not limited to malaria, *Pneumocystis* carnii pneumonia, leishmaniasis, cryptosporidiosis, toxoplasmosis, and trypanosome infection and prions that cause human disease such as Creutzfeldt-Jakob Disease (CJD), variant Creutzfeldt-Jakob Disease (vCJD), Gerstmann-Straussler-Scheinker syndrome, Fatal Familial Insomnia and kuru.

Diagnostic Applications

In some embodiments, the methods and compositions provided herein are useful in detecting a disease or disorder and/or monitoring the progression of a disease or disorder. As used herein, the term "diagnostic" refers identifying the presence or absence of or nature of a disease or disorder. Such detection methods can be used, for example, for early diagnosis of the condition, to determine whether a subject is predisposed to a disease or disorder, to monitor the progress of the disease or disorder or the progress of treatment protocols, to assess the severity of the disease or disorder, to forecast the an outcome of a disease or disorder and/or prospects of recovery, or to aid in the determination of a suitable treatment for a subject. The detection can occur in vitro or in vivo. The effector gene can comprise a diagnostic agent. The effector gene can comprise a diagnostic contrast agent.

In some embodiments, the effector gene encodes a diagnostic agent. In some embodiments, the diagnostic agent aids in the identification of a unique cell type and/or a unique cell state. The diagnostic agent can be a molecule capable of detection, including, but not limited to, fluorescers, chemiluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. For example, the diagnostic agent may comprise, in some embodiments, a fluorescent protein, such as, but not limited to, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, rsCherry, rsCherryRev, or any combination thereof. In some embodiments, the expression, stability, and/or activity (e.g., fluorescence) of the diagnostic agent is configured to be responsive to a disease state or a disorder state.

In some embodiments, the diagnostic agent aids in the identification of a unique cell type and/or a unique cell state. The unique cell type and/or a unique cell state can comprise lesions (e.g. tumors, infected cells). Detection and/or imaging of the diagnostic agent can enable a clinician to intraoperatively, laparoscopically, intravascularly or endoscopically detect said lesions. In some such embodiments, discrimination between lesions (e.g. tumors) and non-lesions (e.g. non-tumor tissue) is enhanced by the detection and/or imaging of the diagnostic agent. In some embodiments, detection and/or imaging of the diagnostic agent can enable a clinician to accurately locate lesions in a patient and thereby aid resection, irradiation, biopsy and/or lesion removal. In some embodiments, detection and/or imaging of the diagnostic agent aids the detection of non-malignant pathological lesions, such as, an infarct, including myocardial, atherosclerotic plaque, clot, including thrombosis, pulmonary embolism, infectious or inflammatory lesion, non-tumorous or noninfectious inflammation, or hyperplasia. The detection and/or imaging of the diagnostic agent may also be used to detect various stages of progression or severity of disease (e.g., benign, premalignant, and malignant breast lesions, tumor growth, or metastasis). The detection and/or imaging of the diagnostic agent may also be used to detect the response of the disease to prophylactic or therapeutic treatments or other interventions. The detection and/or imaging of the diagnostic agent can furthermore be used to help the medical practitioner in determining prognosis (e.g., worsening, status-quo, partial recovery, or complete recovery) of the patient, and the appropriate course of action.

Detection and/or imaging of the diagnostic agent can be performed, for example, using an ultrasound scanner, a magnetic resonance imaging instrument (MM scanner), an X-ray source with film or a detector (e.g., conventional or digital radiography system), an X-ray computed tomography (CT) or computed axial tomography (CAT) scanner, a gamma camera, or a positron emission tomography (PET) scanner. Various medical imaging systems have been developed for open surgery as well as for laparoscopic, thoracoscopic, and robot-assisted surgery and can be used in the practice of the invention. Conventional laparoscopes and endoscopes can be equipped with a photodetector (e.g., camera or CCD detector) to provide guidance during medical procedures. Fiber-optic imaging systems can also be used, which include portable handheld microscopes, flexible endoscopes, and microendoscopes. For example, an illumination source can be added to such devices to allow fluorescence imaging. A miniaturized ultrasound transducer can be added to the tip of a laparoscope or catheter for intravascular ultrasound (NUS) imaging. Miniaturized imaging systems can be used that allow imaging inside small cavities and constricted spaces. In addition, miniaturized imaging devices (e.g., microendoscopes) may be implanted within a subject for long-term imaging studies. In addition, a camera may be used to take both photographic images of a subject and to detect signals from the diagnostic agent, so that photographic images of the subject and images of the signals from the diagnostic agent can be superimposed to allow regions containing the diagnostic agent to be mapped to the subject's anatomy.

Donor Nucleic Acids

There are provided, in some embodiments, donor nucleic acids. The donor nucleic acid can comprise one or more of a recognition site, a splice acceptor site, a self-cleaving peptide sequence, an effector gene, and a transcript stabilization element. The self-cleaving peptide sequence can comprise porcine teschovirus-1 2A peptide (P2A), Thosea asigna virus 2A peptide (T2A), equine rhinitis A virus 2A peptide (E2A), foot-and-mouth disease virus 2A peptide (F2A), or any combination thereof. The transcript stabilization element can be capable of enhancing the stability of a transcript of the effector gene. The transcript stabilization element can comprise woodchuck hepatitis post-translational regulatory element (WPRE), bovine growth hormone polyadenylation (bGH-polyA) signal sequence, human growth hormone polyadenylation (hGH-polyA) signal sequence, or any combination thereof. The splice acceptor site can be capable of being recognized and cleaved by a spliceosome. The splice acceptor site can comprise a branchpoint, a polypyrimidine tract, a 3' splice site, or any combination thereof. The translation frame linker can ensure that the effector gene is expressed in frame with the preceding exon of the target gene. The translation frame linker can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. In some embodiments, the translation frame linker places the effector gene in translational frame with the preceding exon of the target gene. The recognition site can be adjacent to a protospacer adjacent motif (PAM) capable of being recognized by the programmable nuclease. The donor nucleic acid can comprise a translation frame linker. The donor nucleic acid can comprise the structure 5'-[recognition site]-[splice acceptor site]-[translation frame linker]-[self-cleaving peptide sequence]-[effector gene]-3'. The donor nucleic acid can comprise the structure 5'-[recognition site]-[splice acceptor site]-[translation frame linker]-[self-cleaving peptide sequence]-[effector gene]-[transcript stabilization element]-3'. The donor nucleic acid can comprise the target gene coding sequence downstream of the intron. The donor nucleic acid can comprise the structure 5'-[recognition site]-[splice acceptor site]-[target gene coding sequence downstream of the intron]-[self-cleaving peptide sequence]-[effector gene]-3'. The donor nucleic acid can comprise the structure 5'-[recognition site]-[splice acceptor site]-[target gene coding sequence downstream of the intron]-[self-cleaving peptide sequence]-[transcript stabilization element]-3'. The recognition site of the donor nucleic acid and the recognition site of the intron can be the same. In some embodiments, the recognition site does not exist after the donor nucleic acid has been properly incorporated into the intron. In some embodiments, the donor nucleic acid does not comprise a promoter. In some embodiments, the integration of the donor nucleic acid into the target gene through NHEJ can initially result in integration in the wrong orientation. In some such embodiments, the integration in the wrong orientation will reconstitute the recognition site in the genome and the wrongly integrated donor nucleic acid will be cut out again. In some embodiments, only the integration in the correct orientation will break the original recognition site and allow the donor nucleic acid to remain in the genome. In some embodiments, the donor nucleic acid does not comprise transcript stabilization element. In some embodiments, the donor nucleic acid encodes a degron. In some embodiments, the degron is 5' of the self-cleaving peptide. In some embodiments, the degron prevents accumulation of an incomplete target gene product. The degron can comprise a DHFR degron, an N-degron, a phospho degron, a heat inducible degron, a photosensitive degron, an oxygen dependent degron, ornithine decarboxylase degron, estrogen receptor domain degrons, a ecDHFR degron, an FKBP degron, a UnaG degron, or any combination thereof. The donor nucleic acid can comprise an IRES. In some embodiments, the Cell-SELECT donor can further comprise gRNA expression constructs, multiple gRNA cutting sites and/or other components facilitating efficient cellular transduction of the Cell-SELECT reagents.

Figure 3A:
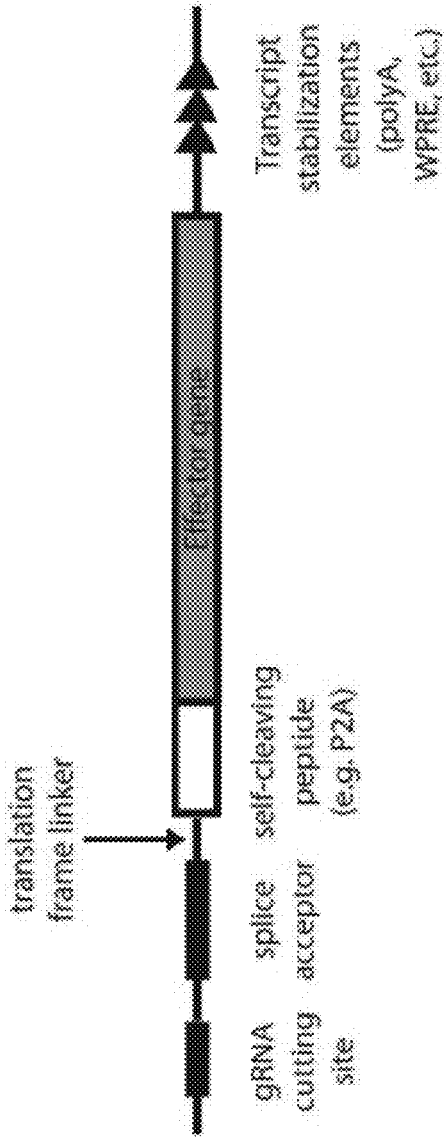
FIGS. 3A-3B show non-limiting exemplary schematic illustrations of Cell-SELECT donor constructs (e.g., donor nucleic acids) for cell type specific expression of effector genes with their respective structural elements.
Figure 3B:
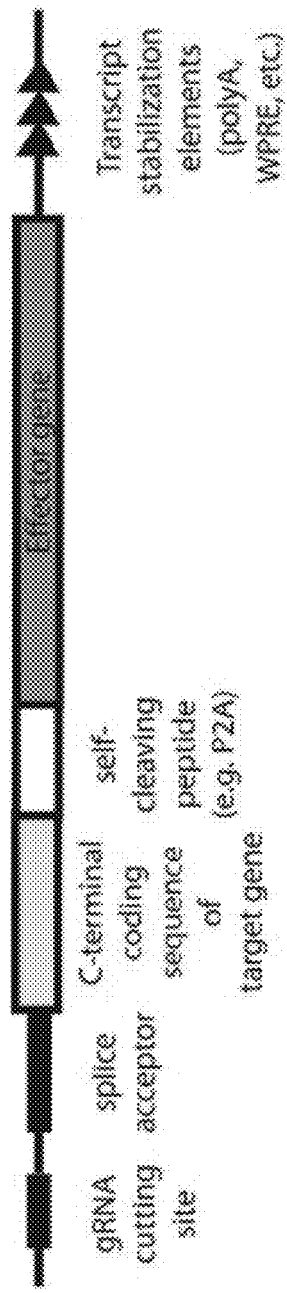

FIGS. 3A-3B show non-limiting exemplary schematic illustrations of Cell-SELECT donor constructs (e.g., donor nucleic acids) for cell type specific expression of effector genes with their respective structural elements. FIG. 3A shows the basic design of a CELL-SELECT donor (e.g., donor nucleic acid) comprising the following elements: gRNA cutting site—for linearizing the donor construct that primes it for genomic integration through NHEJ; splice acceptor site—ensures splicing of the effector gene to the preceding exon of the target gene; translation frame linker—short DNA sequence ensuring that the effector gene is in translational frame with the preceding exon of the target gene; self-cleaving peptide—enables separation of the effector protein from the target gene product and therefore independent intracellular localization for the former; transcript stabilization elements—DNA sequences that facilitate the nuclear export and resulting chimeric transcript stability for enhanced expression (e.g. WPRE sequences, polyA sequences and others). FIG. 3B depicts a Cell-SELECT donor (e.g., donor nucleic acid) that preserves the function of the target gene. In some embodiments, this donor nucleic acid can be used to prevent functional disruption of the target gene and therefore includes the C-terminal coding sequence of the targeted gene. In some embodiments, this target gene-preserving donor nucleic acid prevents functional disruption of the genomic locus while still affording precise effector gene expression.

The Cell-SELECT donor (e.g., donor nucleic acid) can enable selective and high efficiency expression of desired effector genes. The donor construct can comprise one or more functional components, including, but not limited to: a) a recognition site (e.g., a sgRNA cutting site), that is cleaved in the presence of a programmable nuclease (e.g., Cas9 nuclease) and respective targeting molecule (e.g., gRNA) that primes the donor for genomic integration through NHEJ; b) splice acceptor site, which can comprise both branch point and polypyrimidine stretches that function to capture the splice machinery after transcription of the hybrid transcript; c) translation frame linker—short DNA sequence that places the downstream effector gene in translational frame with the targeted gene's exon; d) self-cleaving peptide—this DNA stretch encodes the sequence of a self-cleaving peptide (e.g., P2A, T2A) that releases the effector gene from the targeted gene product enabling independent subcellular targeting of the effector gene product; e) effector gene coding sequence—this can be any protein encoding gene that brings about desired functional alteration in the targeted cell-type; and/or f) one or more transcript stabilization sequences—these include DNA sequences that ensure extended transcript stability following transcription that may include WPRE sequences, polyA sequences (e.g. bGH-polyA, hGH-polyA or others) (FIG. 3A). In embodiments of the disclosed methods requiring the preservation of the targeted gene function, the Cell-SELECT donor can also include the C-terminal coding sequence of the targeted gene that reconstitutes a fully functional targeted gene product followed by the effector gene sequence (FIG. 3B). This design can preclude the disruption of the targeted gene.

Programmable nucleases and Targeting Molecules

The programmable nuclease can be capable of inducing a double-stranded DNA break. The programmable nuclease can comprise *Streptococcus pyogenes* Cas9 (SpCas9) and/or *Staphylococcus aureus* Cas9 (SaCas9). The programmable nuclease can comprise Cas1, Cas1B, Cas2, Cas3, Cas4, Cas5, Cash, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c3, Cas12a, Cas12b, Cas12c, Cas12d, Cas12e, Cas13a, Cas13b, Cas13c, derivatives thereof, or any combination thereof. The programmable nuclease can comprise a zinc finger nuclease, TAL effector nuclease, meganuclease, MegaTAL, Tev-m TALEN, MegaTev, homing endonuclease, derivatives thereof, or any combination thereof. The targeting molecule can be capable of associating with the programmable nuclease. The targeting molecule can comprise single strand DNA or single strand RNA. The targeting molecule can comprise a single guide RNA (sgRNA). The targeting molecule can comprise a synthetic nucleic acid. There are provided, in some embodiments, programmable gene editing reagents. In some embodiments, the programmable nuclease comprises a nucleic acid guided DNA endonuclease (e.g., Cas9). Some embodiments of the methods and compositions provided herein employ *Streptococcus pyogenes* Cas9 (SpCas9), *Staphylococcus aureus* Cas9 (SaCas9), or any other nuclease that can be guided to cut specific DNA sequences and introduce double-stranded DNA breaks fulfills the function of both specifying the targeted genomic region as well as priming the Cell-SELECT donor for NHEJ dependent genomic integration. Some embodiments of the methods and compositions provided herein employ a targeting molecule (e.g, a gRNA or other nuclease targeting mechanism). The targeting molecule can fulfill two functions in the Cell-SELECT method: 1) it can specify the genomic region (targeted gene intron) for targeted integration of the Cell-SELECT donor; and/or 2) it can function to linearize or cut out the Cell-SELECT donor sequence priming it for genomic integration. The nuclease targeting mechanism can also be an integral part of the nuclease as is the case with TALENs or zinc-finger nucleases (ZFNs).

Compositions and Methods of Administration

All cell-SELECT components described herein can be delivered to desired tissues by a range of viral or non-viral methods as described herein. The selection of a delivery method can depend on the embodiment, including on the specific type of cells and tissues to which the Cell-SELECT method is deployed, whether the cells are dividing or non-dividing, the efficiency of cellular uptake of particular delivery reagents in a tissue of interest, the desired duration of delivery and many other factors. One factor in determining the choice of delivery method is the achievement of a sufficiently high nuclear concentration of the Cell-SELECT donor construct for successful genomic integration.

Targeting molecules (e.g., gRNA or other nuclease activity guiding entities) can be introduced to the cell in one of many formulations that include but are not limited to the following examples: a) guide-RNA expression construct where the genome targeting and donor linearizing gRNA is expressed under the U6 promoter. The DNA that harbors the gRNA expression cassette can be introduced to the cell by either non-viral methods (e.g. electroporation, lipid based transfection, etc.), or as part of a viral vector based delivery strategy (e.g. AAV or lentiviral vectors); b) as a ribonucleoprotein (RNP) complex where the gRNA forms an active complex with the programmable nuclease prior to delivery; c) delivered in the RNA form; and/or d) synthetic non-RNA based guide polymers. The disclosed Cell-SELECT donors can be delivered in various formulations depending on the embodiment. For example, they can be targeted to the cell nucleus as DNA plasmids (e.g. in a minicircle plasmid form lacking any superfluous components or regular plasmids with bacterial backbone). They can also be delivered with a viral vector (e.g. AAV or lentiviral vector) that comprises the donor sequences and can be partially or fully integrated to the genome after cleavage of respective gRNA target sites. The programmable nuclease can be delivered in one of many formulations that include but are not limited to the following examples: a) a programmable nuclease can be delivered as a DNA based expression construct following a promoter sequence, and this can be delivered as a mini-circle DNA or regular plasmid or part of a viral genome (e.g. AAV or lentiviral vector) that facilitates the delivery of the DNA to the nucleus; b) a ribonucleoprotein that includes the gRNA specifying the targeted DNA cutting sequence; c) as an mRNA bringing about transient expression of the nuclease; and/or d) from a transgenic expression construct in the organism's genome.

Disclosed herein include compositions. In some embodiments, the composition comprises: (i) a programmable nuclease or a nucleic acid encoding the programmable nuclease; (ii) a targeting molecule or a nucleic acid encoding the targeting molecule, and/or (iii) a donor nucleic acid or a nucleic acid encoding the donor nucleic acid. The programmable nuclease, the targeting molecule, and/or the donor nucleic acid can be encoded on the same nucleic acid. The programmable nuclease, the targeting molecule, and/or the donor nucleic acid can be encoded on different nucleic acids. In some embodiments, the nucleic acid encoding the programmable nuclease, the nucleic acid encoding the targeting molecule, and/or the nucleic acid encoding the donor nucleic acid comprise DNA and/or RNA. The nucleic acid encoding the programmable nuclease, the nucleic acid encoding the targeting molecule, and/or the nucleic acid encoding the donor nucleic acid can be component(s) of a vector. The vector can comprise (i) a programmable nuclease or a nucleic acid encoding the programmable nuclease; (ii) a targeting molecule or a nucleic acid encoding the targeting molecule, and/or (iii) a donor nucleic acid or a nucleic acid encoding the donor nucleic acid. The vector can be an AAV vector, a lentivirus, an integration-deficient lentivirus (IDLY), a plasmid vector, a naked DNA vector, a lipid nanoparticle, or any combination thereof. The plasmid vector can comprise a minicircle plasmid. The AAV vector can comprise AAV1, AAV2, AAV3, AAV4, AAV5, AAV6, AAV7, AAV8, AAV9, or any combination thereof. The vector can be a neurotropic viral vector. The neurotropic viral vector can comprise or can be derived from Herpesviridae, varicella zoster virus, pseudorabies virus, cyromegalovirus, Epstein-barr virus, encephalitis virus, polio virus, coxsackie virus, echo virus, mumps virus, measles virus, rabies virus, or any combination thereof. The vector can comprise a heterologous promoter that drives expression of the programmable nuclease, the targeting molecule, and/or the donor nucleic acid. The heterologous promoter can be an inducible promoter. The programmable nuclease, the targeting molecule, and/or the donor nucleic acid can be encoded by a transgenic construct in the genome of the cell. The (i) a programmable nuclease or a nucleic acid encoding the programmable nuclease; (ii) a targeting molecule or a nucleic acid encoding the targeting molecule, and/or (iii) a donor nucleic acid or a nucleic acid encoding the donor nucleic acid can be a component of a ribonucleoprotein (RNP) complex. As disclosed herein, glycoprotein of the viral vector can be modified so that the viral vector is targeted to a particular target environment of interest such as central nervous system, and to enhance tropism to the target environment of interest (e.g, CNS tropism). In some embodiments, the viral vector delivers a polynucleotide to the heart, peripheral nerves, or a combination thereof. Pharmaceutical compositions can be prepared, for example, as injectable formulations.

In some embodiments, the vector can comprise an adenovirus vector, an adeno-associated virus vector, an Epstein-Barr virus vector, a Herpes virus vector, an attenuated HIV vector, a retroviral vector, a vaccinia virus vector, or any combination thereof. In some embodiments, the vector can comprise an RNA viral vector. In some embodiments, the vector can be derived from one or more negative-strand RNA viruses of the order Mononegavirales. In some embodiments, the vector can be a rabies viral vector. Many such vectors useful for transferring exogenous genes into target mammalian cells are available. The vectors may be episomal, e.g. plasmids, virus-derived vectors such cytomegalovirus, adenovirus, etc., or may be integrated into the target cell genome, through homologous recombination or random integration, e.g. retrovirus-derived vectors such as MMLV, HIV-1, ALV, etc. In some embodiments, combinations of retroviruses and an appropriate packaging cell line may also find use, where the capsid proteins will be functional for infecting the target cells. Retroviral vectors can be "defective", i.e. unable to produce viral proteins required for productive infection. Replication of the vector can require growth in the packaging cell line. The term "vector", as used herein, can refer to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc. There are provided, in some embodiments, expression vectors. As used herein, the term "expression vector" refers to a vector that directs expression of an RNA or polypeptide (e.g., a Cell-SELECT component) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

Integrating vectors have their delivered RNA/DNA permanently incorporated into the host cell chromosomes. Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector. One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs. Another non-integrative viral vector is adenoviral vector and the adenoassociated viral (AAV) vector. Other non-integrative viral vectors contemplated herein are single-strand negative-sense RNA viral vectors, such Sendai viral vector and rabies viral vector. Another example of a non-integrative vector is a minicircle vector. Minicircle vectors are circularized vectors in which the plasmid backbone has been released leaving only the eukaryotic promoter and cDNA(s) that are to be expressed. As used herein, the term "viral vector" can refer to a nucleic acid vector construct that includes at least one element of viral origin and has the capacity to be packaged into a viral vector particle. The viral vector can contain a nucleic acid encoding a polypeptide as described herein in place of nonessential viral genes. The vector and/or particle may be utilized for the purpose of transferring nucleic acids into cells either in vitro or in vivo. Numerous forms of viral vectors are known in the art.

In some embodiment, the vectors can include a regulatory sequence that allows, for example, the translation of multiple proteins from a single mRNA. Non-limiting examples of such regulatory sequences include internal ribosome entry site (IRES) and 2A self-processing sequence. In some embodiments, the 2A sequence is a 2A peptide site from foot-and-mouth disease virus (F2A sequence). In some embodiments, the F2A sequence has a standard furin cleavage site. In some embodiments, the vector can also comprise regulatory control elements known to one of skill in the art to influence the expression of the RNA and/or protein products encoded by the polynucleotide within desired cells of the subject. In some embodiments, functionally, expression of the polynucleotide is at least in part controllable by the operably linked regulatory elements such that the element(s) modulates transcription of the polynucleotide, transport, processing and stability of the RNA encoded by the polynucleotide and, as appropriate, translation of the transcript. A specific example of an expression control element is a promoter, which is usually located 5' of the transcribed sequence. Another example of an expression control element is an enhancer, which can be located 5' or 3' of the transcribed sequence, or within the transcribed sequence. Another example of a regulatory element is a recognition sequence for a microRNA. Another example of a regulatory element is an ration and the splice donor and splice acceptor sequences that regulate the splicing of said intron. Another example of a regulatory element is a transcription termination signal and/or a polyadenylation sequence.

An effective amount of the disclosed Cell-SELECT reagents can be introduced into a cell and/or delivered into a subject may any means known in the art. The method can comprise: isolating the cell from the subject prior to the introducing step. The method can comprise: administering the cell into a subject after the introducing step. The introducing step can be performed in vivo, in vitro, and/or ex vivo. The introducing step can comprise calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof. The introducing step can comprise administering (i) a programmable nuclease or a nucleic acid encoding the programmable nuclease; (ii) a targeting molecule or a nucleic acid encoding the targeting molecule, and/or (iii) a donor nucleic acid or a nucleic acid encoding the donor nucleic acid to a subject comprising the cell. The introducing step can comprise administering a vector to a subject comprising the cell. The vector can comprise (i) a programmable nuclease or a nucleic acid encoding the programmable nuclease; (ii) a targeting molecule or a nucleic acid encoding the targeting molecule, and/or (iii) a donor nucleic acid or a nucleic acid encoding the donor nucleic acid.

The administering can comprise aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof. There are provided, in some embodiments, pharmaceutical composition for administration of any of the compositions provided herein. The pharmaceutical composition can be formulated with a pharmaceutically acceptable carrier or excipient. A pharmaceutically acceptable carrier or excipient refers to a carrier (e.g., carrier, media, diluent, solvent, vehicle, etc.) which does not significantly interfere with the biological activity or effectiveness of the active ingredient(s) of a pharmaceutical composition and which is not excessively toxic to the host at the concentrations at which it is used or administered. Other pharmaceutically acceptable ingredients can be present in the composition as well. Suitable substances and their use for the formulation of pharmaceutically active compounds are well known in the art. A pharmaceutical composition is typically formulated to be compatible with its intended route of administration. For topical application, a pharmaceutical composition may be formulated in a suitable ointment, lotion, gel, or cream containing the active components suspended or dissolved in one or more pharmaceutically acceptable carriers suitable for use in such compositions. For some applications, the composition is formulated as a solid (e.g., lyophilized), liquid, gel, or hydrogel and may contain additives such as surfactants, buffers (e.g., succinate), salts (e.g., sodium chloride), polymers (e.g., polysaccharides, hyaluronic acid), proteins (e.g., albumin, human serum albumin), or amino acids (e.g., methionine).

Also disclosed herein are pharmaceutical compositions comprising one or more of the Cell-SELECT reagents disclosed herein and one or more pharmaceutically acceptable carriers. The compositions can also comprise additional ingredients such as diluents, stabilizers, excipients, and adjuvants. As used herein, "pharmaceutically acceptable" carriers, excipients, diluents, adjuvants, or stabilizers are the ones nontoxic to the cell or subject being exposed thereto (preferably inert) at the dosages and concentrations employed or that have an acceptable level of toxicity as determined by the skilled practitioners.

The carriers, diluents and adjuvants can include buffers such as phosphate, citrate, or other organic acids: antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, di saccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG). In some embodiments, the physiologically acceptable carrier is an aqueous pH buffered solution.

Titers of the disclosed Cell-SELECT reagents to be administered will vary depending, for example, on the particular delivery composition (e.g., viral vector), the mode of administration, the treatment goal, the individual, and the cell type(s) being targeted, and can be determined by methods standard in the art.

Actual administration of the disclosed Cell-SELECT reagents can be accomplished by using any physical method that will transport the disclosed Cell-SELECT reagents into the cells (e.g., target tissue) of the subject. For example, the disclosed Cell-SELECT reagents can be administered intravenously.

A therapeutically effective amount of the disclosed Cell-SELECT reagents can be administered to a subject at various points of time. For example, the disclosed Cell-SELECT reagents can be administered to the subject prior to, during, or after the subject has developed a disease, disorder, and/or infection. The disclosed Cell-SELECT reagents can also be administered to the subject prior to, during, or after the occurrence of a disease, disorder, and/or infection. In some embodiments, the disclosed Cell-SELECT reagents are administered to the subject during remission of the disease or disorder. In some embodiments, the disclosed Cell-SELECT reagents are administered prior to the onset of the disease or disorder in the subject. In some embodiments, the disclosed Cell-SELECT reagents are administered to a subject at a risk of developing the disease or disorder.

Administering can comprise intracranial injection, aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof. Administering can comprise an injection into a brain region. The brain region can comprise the Lateral parabrachial nucleus, brainstem, Medulla oblongata, Medullary pyramids, Olivary body, Inferior olivary nucleus, Rostral ventrolateral medulla, Respiratory center, Dorsal respiratory group, Ventral respiratory group, Pre-Botzinger complex, Botzinger complex, Paramedian reticular nucleus, Cuneate nucleus, *Gracile* nucleus, Intercalated nucleus, Area postrema, Medullary cranial nerve nuclei, Inferior salivatory nucleus, Nucleus *ambiguus*, Dorsal nucleus of vagus nerve, Hypoglossal nucleus, Solitary nucleus, Pons, Pontine nuclei, Pontine cranial nerve nuclei, chief or pontine nucleus of the trigeminal nerve sensory nucleus (V), Motor nucleus for the trigeminal nerve (V), Abducens nucleus (VI), Facial nerve nucleus (VII), vestibulocochlear nuclei (vestibular nuclei and cochlear nuclei) (VIII), Superior salivatory nucleus, Pontine tegmentum, Respiratory centers, Pneumotaxic center, Apneustic center, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, Tectum, Corpora quadrigemina, inferior colliculi, superior colliculi, Pretectum, Tegmentum, Periaqueductal gray, Parabrachial area, Medial parabrachial nucleus, Subparabrachial nucleus (Kölliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars *compacta, Pars reticulata*, Interpeduncular nucleus, Cerebral peduncle, Crus cerebri, Mesencephalic cranial nerve nuclei, Oculomotor nucleus (III), Trochlear nucleus (IV), Mesencephalic duct (cerebral aqueduct, aqueduct of Sylvius), Pineal body, Habenular nucleim Stria medullares, *Taenia* thalami, Subcommissural organ, Thalamus, Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedial nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventral lateral nucleus, Ventral posterior nucleus, Ventral posterior lateral nucleus, Ventral posterior medial nucleus, Metathalamus, Medial *geniculate* body, Lateral *geniculate* body, Thalamic reticular nucleus, Hypothalamus, limbic system, HPA axis, preoptic area, Medial preoptic nucleus, Suprachiasmatic nucleus, Paraventricular nucleus, Supraoptic nucleusm Anterior hypothalamic nucleus, Lateral preoptic nucleus, median preoptic nucleus, periventricular preoptic nucleus, Tuberal, Dorsomedial hypothalamic nucleus, Ventromedial nucleus, Arcuate nucleus, Lateral area, Tuberal part of Lateral nucleus, Lateral tuberal nuclei, Mammillary nuclei, Posterior nucleus, Lateral area, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, Subthalamus, Subthalamic nucleus, Zona incerta, Pituitary gland, neurohypophysis, Pars *intermedia*, adenohypophysis, cerebral hemispheres, Corona *radiata*, Internal capsule, External capsule, Extreme capsule, Arcuate fasciculus, Uncinate fasciculus, Perforant Path, Hippocampus, Dentate gyms, Cornu ammonis, Cornu ammonis area 1, Cornu ammonis area 2, Cornu ammonis area 3, Cornu ammonis area 4, Amygdala, Central nucleus, Medial nucleus (accessory olfactory system), Cortical and basomedial nuclei, Lateral and basolateral nuclei, extended amygdala, Stria terminalis, Bed nucleus of the stria terminalis, Claustrum, Basal ganglia, Striatum, Dorsal striatum (aka neostriatum), Putamen, Caudate nucleus, Ventral striatum, Striatum, Nucleus accumbens, Olfactory tubercle, Globus pallidus, Subthalamic nucleus, Basal forebrain, Anterior perforated substance, Substantia innominata, Nucleus basalis, Diagonal band of Broca, Septal nuclei, Medial septal nuclei, Lamina terminalis, Vascular organ of lamina terminalis, Olfactory bulb, Piriform cortex, Anterior olfactory nucleus, Olfactory tract, Anterior commissure, Uncus, Cerebral cortex, Frontal lobe, Frontal cortex, Primary motor cortex, Supplementary motor cortex, Premotor cortex, Prefrontal cortex, frontopolar cortex, Orbitofrontal cortex, Dorsolateral prefrontal cortex, dorsomedial prefrontal cortex, ventrolateral prefrontal cortex, Superior frontal gyms, Middle frontal gyms, Inferior frontal gyms, Brodmann areas (4, 6, 8, 9, 10, 11, 12, 24, 25, 32, 33, 44, 45, 46, and/or 47), Parietal lobe, Parietal cortex, Primary somatosensory cortex (51), Secondary somatosensory cortex (S2), Posterior parietal cortex, postcentral gyms, precuneus, Brodmann areas (1, 2, 3 (Primary somesthetic area), 5, 7, 23, 26, 29, 31, 39, and/or 40), Occipital lobe, Primary visual cortex (V1), V2, V3, V4, V5/MT, Lateral occipital gyms, Cuneus, Brodmann areas (17 (V1, primary visual cortex), 18, and/or 19), temporal lobe, Primary auditory cortex (A1), secondary auditory cortex (A2), Inferior temporal cortex, Posterior inferior temporal cortex, Superior temporal gyms, Middle temporal gyms, Inferior temporal gyms, Entorhinal Cortex, Perirhinal Cortex, Parahippocampal gyms, Fusiform gyms, Brodmann areas (9, 20, 21, 22, 27, 34, 35, 36, 37, 38, 41, and/or 42), Medial superior temporal area (MST), insular cortex, cingulate cortex, Anterior cingulate, Posterior cingulate, dorsal cingulate, Retrosplenial cortex, Indusium *griseum*, Subgenual area 25, Brodmann areas (23, 24; 26, 29, 30 (retrosplenial areas), 31, and/or 32), cranial nerves (Olfactory (I), Optic (II), Oculomotor (III), Trochlear (IV), Trigeminal (V), Abducens (VI), Facial (VII), Vestibulocochlear (VIII), Glossopharyngeal (IX), Vagus (X), Accessory (XI), Hypoglossal (XII)), or any combination thereof.

The brain region can comprise neural pathways Superior longitudinal fasciculus, Arcuate fasciculus, Thalamocortical radiations, Cerebral peduncle, Corpus callosum, Posterior commissure, Pyramidal or corticospinal tract, Medial longitudinal fasciculus, dopamine system, Mesocortical pathway, Mesolimbic pathway, Nigrostriatal pathway, Tuberoinfundibular pathway, serotonin system, Norepinephrine Pathways, Posterior column-medial lemniscus pathway, Spinothalamic tract, Lateral spinothalamic tract, Anterior spinothalamic tract, or any combination thereof.

EXAMPLES

Some aspects of the embodiments discussed above are disclosed in further detail in the following examples, which are not in any way intended to limit the scope of the present disclosure.

Example 1

Figure 4A:
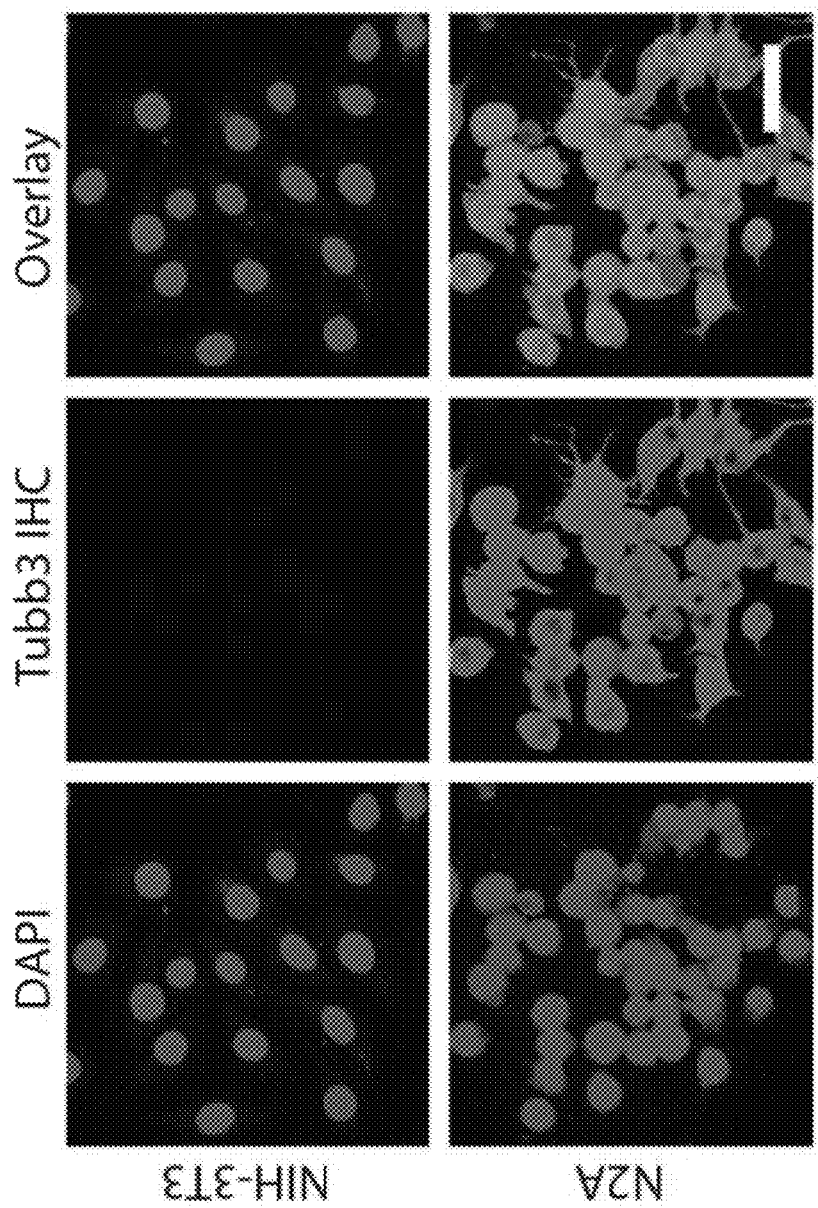
FIGS. 4A-4E depict data related to the ability of the Cell-SELECT method to target the expression of the effector gene to molecularly defined cell types in cell culture.
Figure 4B:
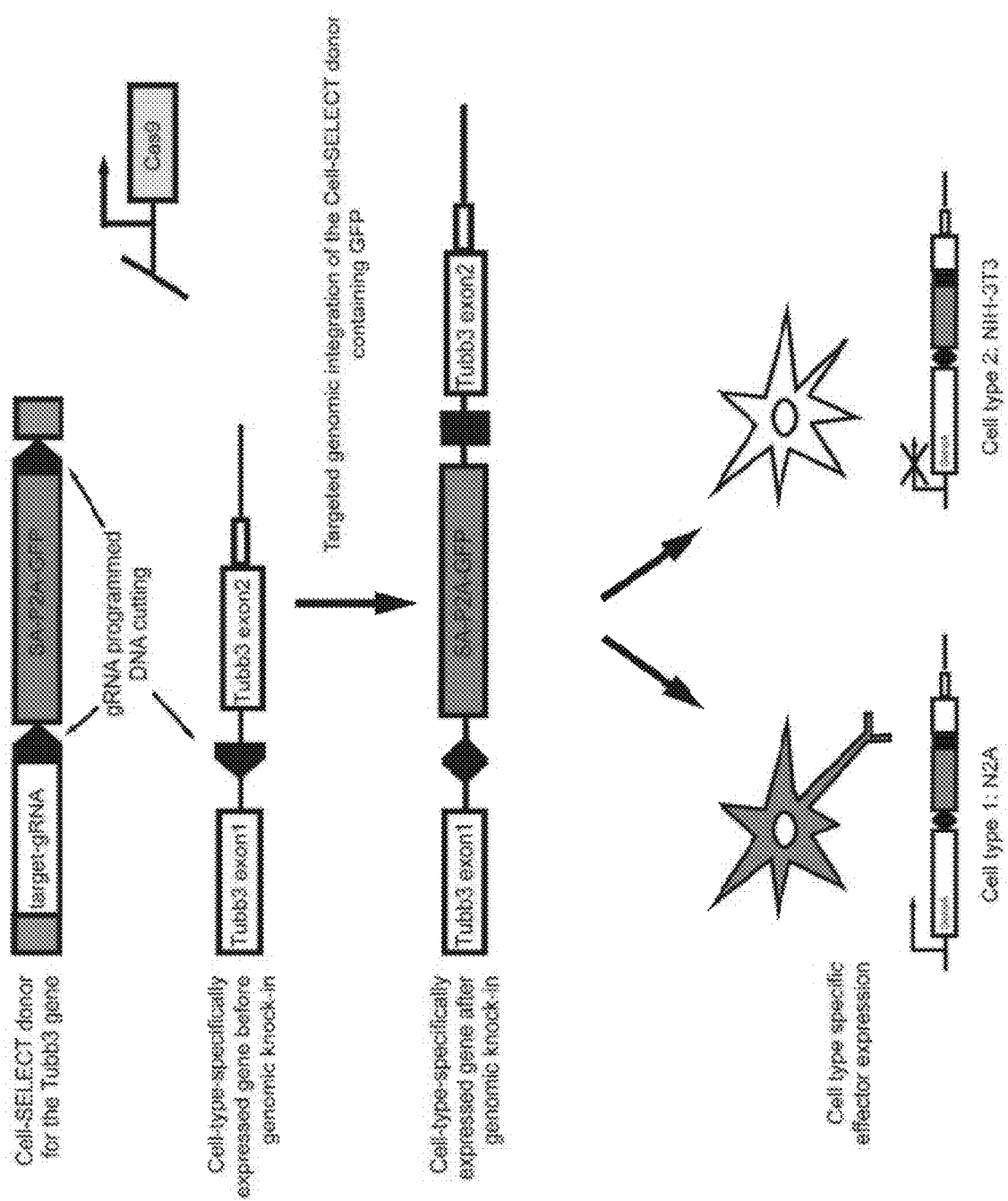
Figure 4C:
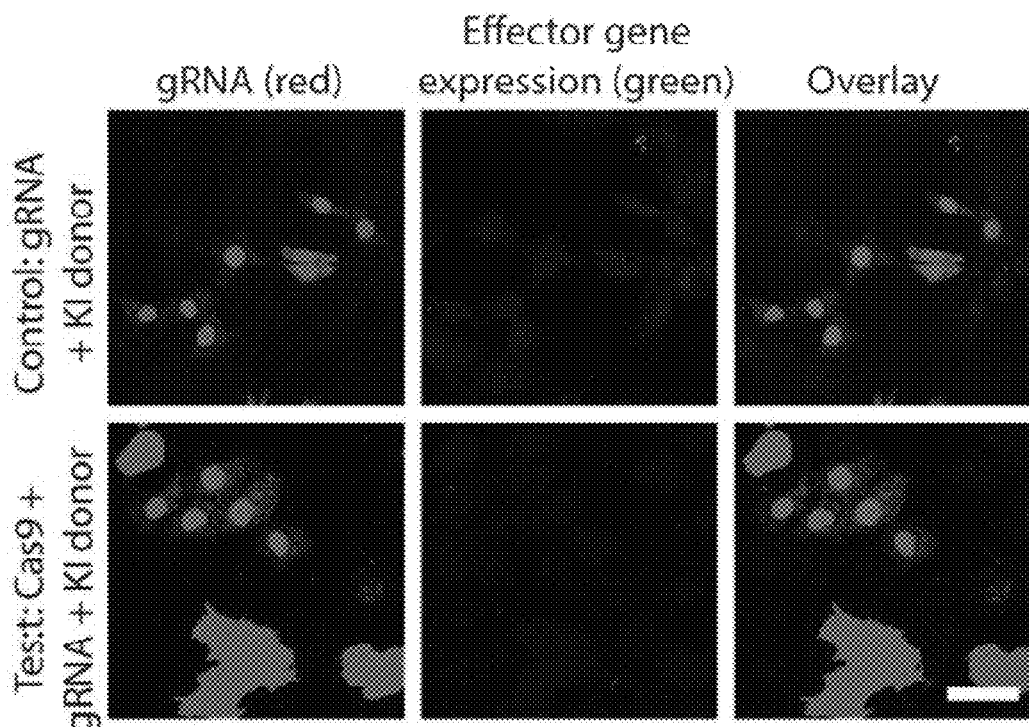
Figure 4D:
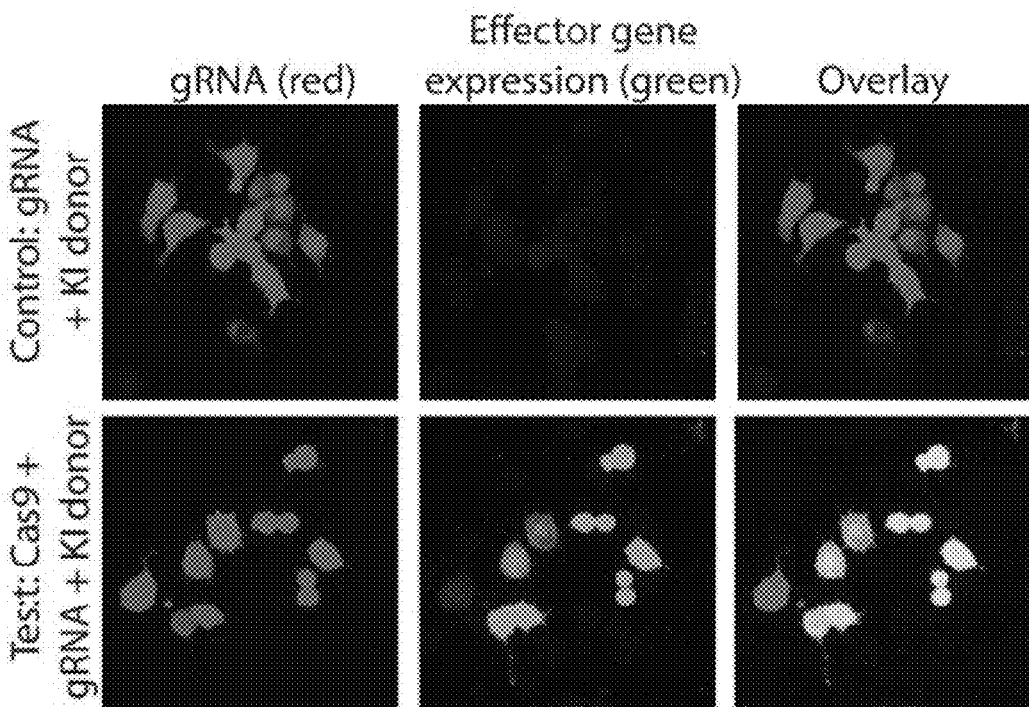
Figure 4E:
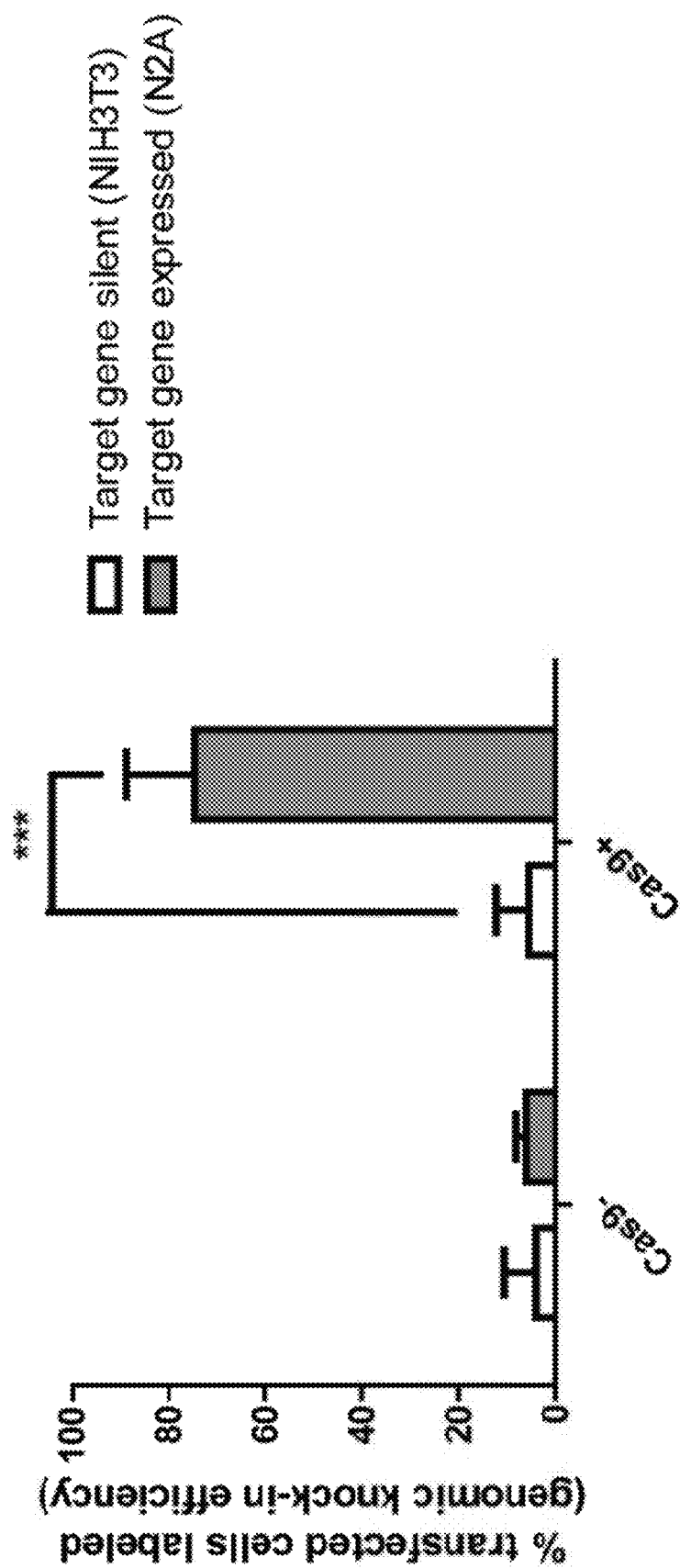

Targeted Expression of an Effector Gene in Molecularly Defined Cell Types in Cell Culture by the Cell-SELECT Method This example provides proof of concept for the Cell-SELECT method provided herein. It was demonstrated that the Cell-SELECT constructs described herein can reliably and robustly reproduce the expression pattern of the genetic locus being targeted. This was initially done in primary neural cultures. The gene editing machinery (e.g., guide RNA) was designed to target Cell-SELECT construct integration to the first intron of a pan-neuronally expressed gene (Tubb3). The Cell-SELECT donor vectors carried a fluorescent reporter gene for rapid integration read-out. In some embodiments, intronic integration, splice acceptor and transcript stabilization components were optimized to yield the highest efficiency expression of Cell-SELECT delivered genes. Some embodiments of the Cell-SELECT donor and guide RNA combinations were further validated in vivo by adeno-associated virus dependent vector delivery through stereotactic brain injections (see below Examples). FIGS. 4A-4E demonstrate the ability of the disclosed Cell-SELECT method to target the expression of the effector gene to a molecularly defined cell types in cell culture. FIG. 4A shows that the gene Tubb3 was expressed in the neuroblastoma cell line N2A whereas it was absent in the fibroblast cell line NIH-3T3 (scale bar–25 microns). Tubb3 IHC—immunohistochemical labeling of Tubb3 protein. DAPI—nuclear stain. FIG. 4B depicts an exemplary experimental design for demonstrating cell-type-specific targeting efficiency of the Cell-SELECT technology. The cell-SELECT donor was knocked into the Tubb3 gene locus. Since Tubb3 was only expressed in one of the tested cell lines (N2A) and not expressed in the other (NIH-3T3), the effector gene was expected to be active (cells labeled by GFP fluorescence) only in Tubb3 expressing cells. The Cell-SELECT effector gene was spliced to the exon of the cell-type-specifically expressed gene (Tubb3) and during translation released as an independent protein due to self-cleavage of the P2A peptide linker. SA—splice acceptor. P2A—self cleaving linker peptide sequence, GFP—green fluorescent protein. In some embodiments, the Cell-SELECT donor construct comprises SEQ ID NO: 1. FIG. 4C shows that transfection of cells lacking the expression of the targeted Tubb3 gene (NIH-3T3) with Cell-SELECT knock-in construct carrying the GFP effector gene, Cas9 nuclease and Tubb3 intron targeting gRNA does not lead to expression of the effector gene. The control condition lacks Cas9 nuclease, and the test condition includes all three Cell-SELECT gene editing components. gRNA expression cassette includes the red mCherry reporter, and successful effector gene activity labels cells green. FIG. 4D shows that transfection of Tubb3 expressing cells (N2A) gene with Cell-SELECT knock-in construct carrying the GFP effector gene, Cas9 nuclease and Tubb3 intron targeting gRNA leads to high efficiency expression of the effector gene (GFP). Overlap between gRNA and successful effector-gene expressing cells shown in yellow in the "Overlay" panel. The control condition lacks Cas9 nuclease, and the test condition includes all three Cell-SELECT gene editing components. FIG. 4E shows the quantification of cell-type-specific targeting efficiency of the Cell-SELECT technology (n=8, *** –p<0.001, unpaired t-test).

Example 2

Figure 5A:
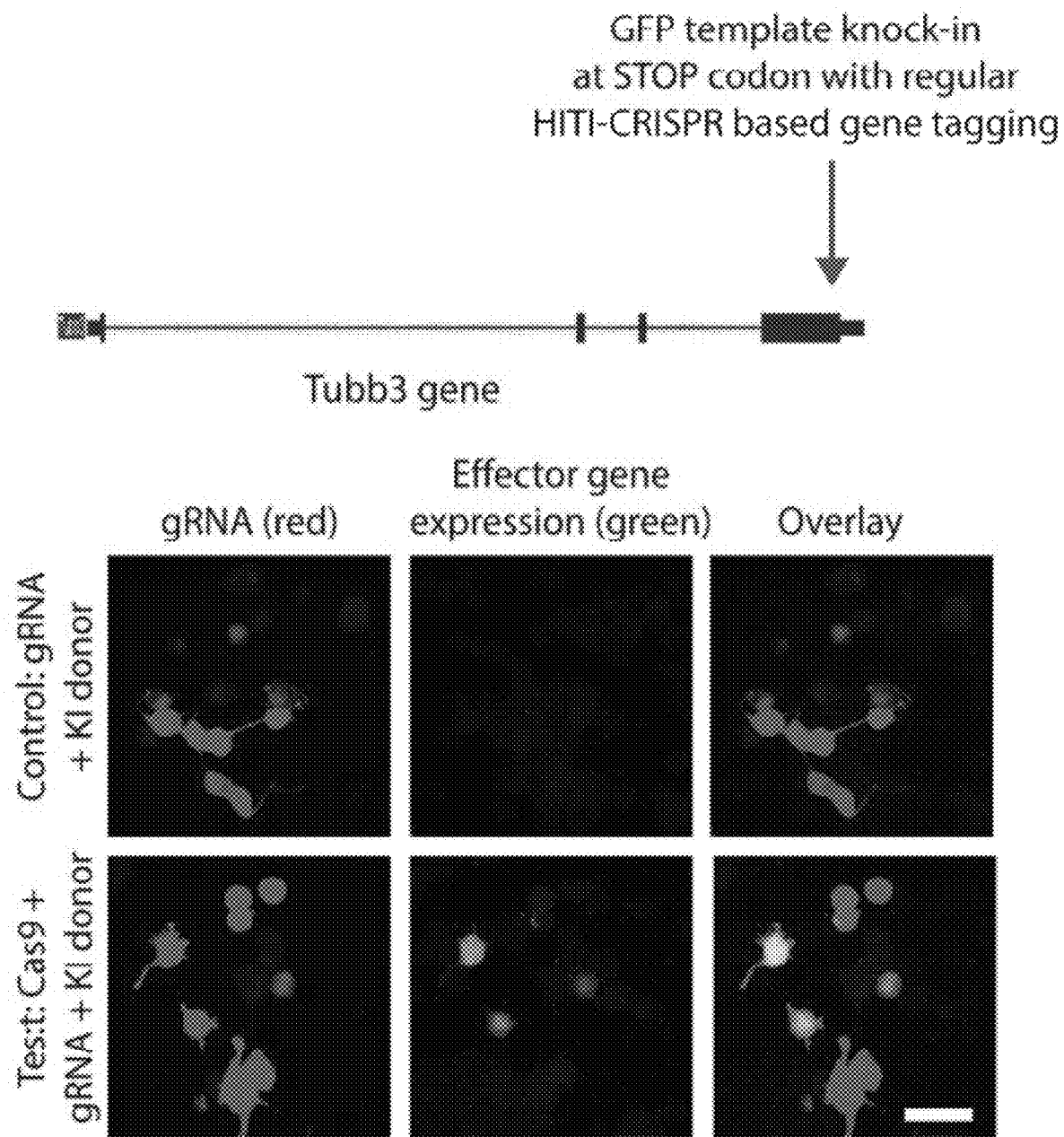
FIGS. 5A-5C depict data related to the knock-in efficiency of the Cell-SELECT method as compared to other gene editing methods in a cell culture model expressing the targeted Tubb3 gene (N2A cell line).
Figure 5B:
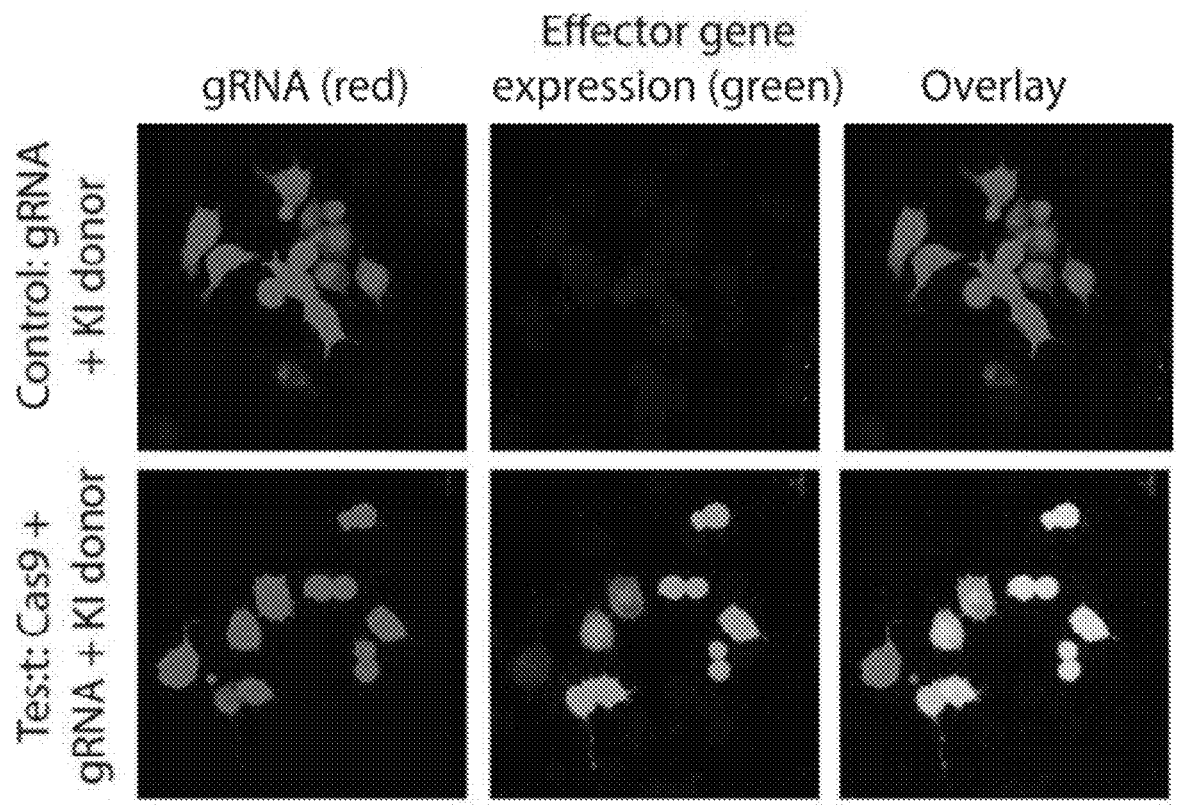
Figure 5C:
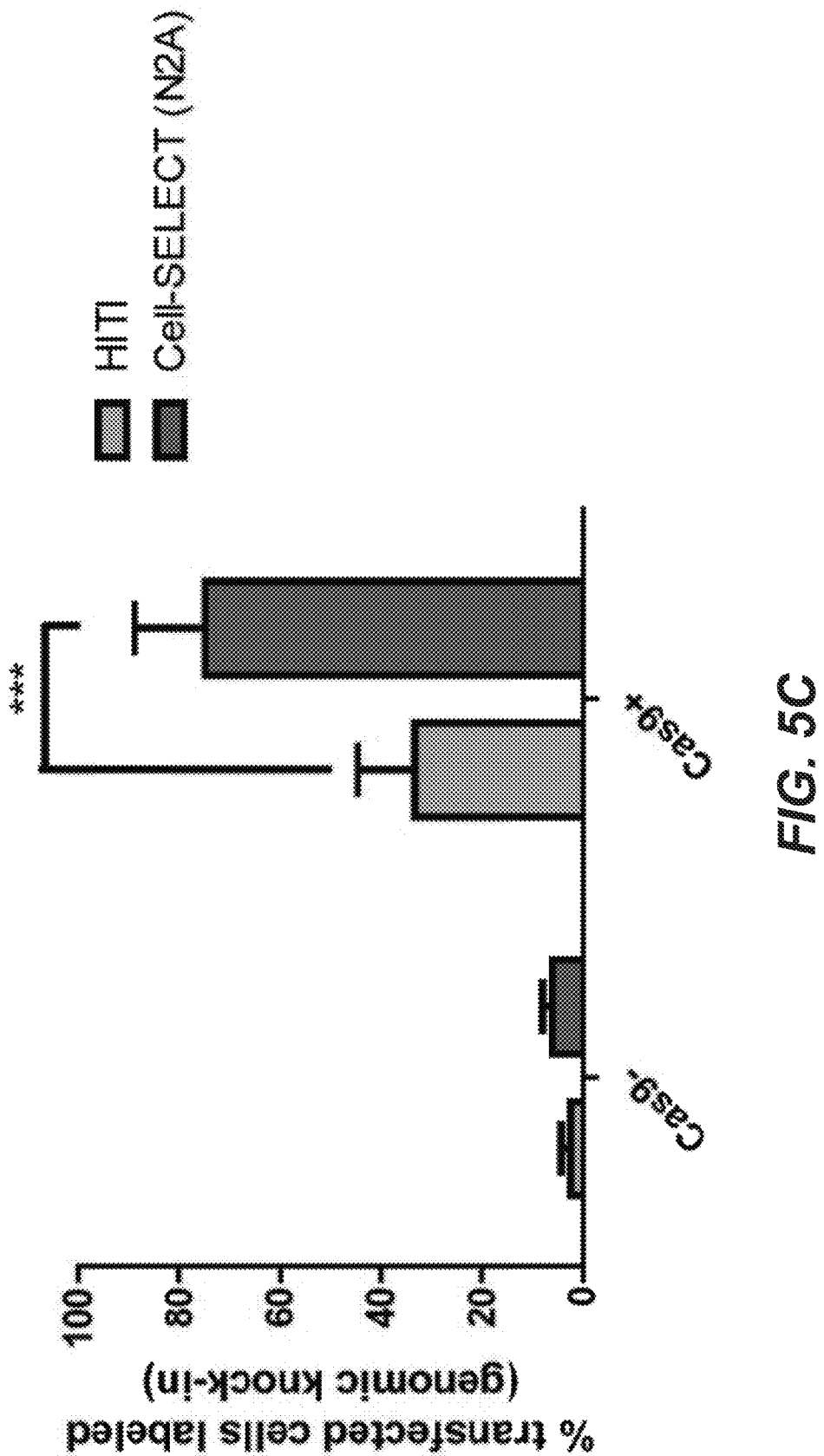
Figure 6A:
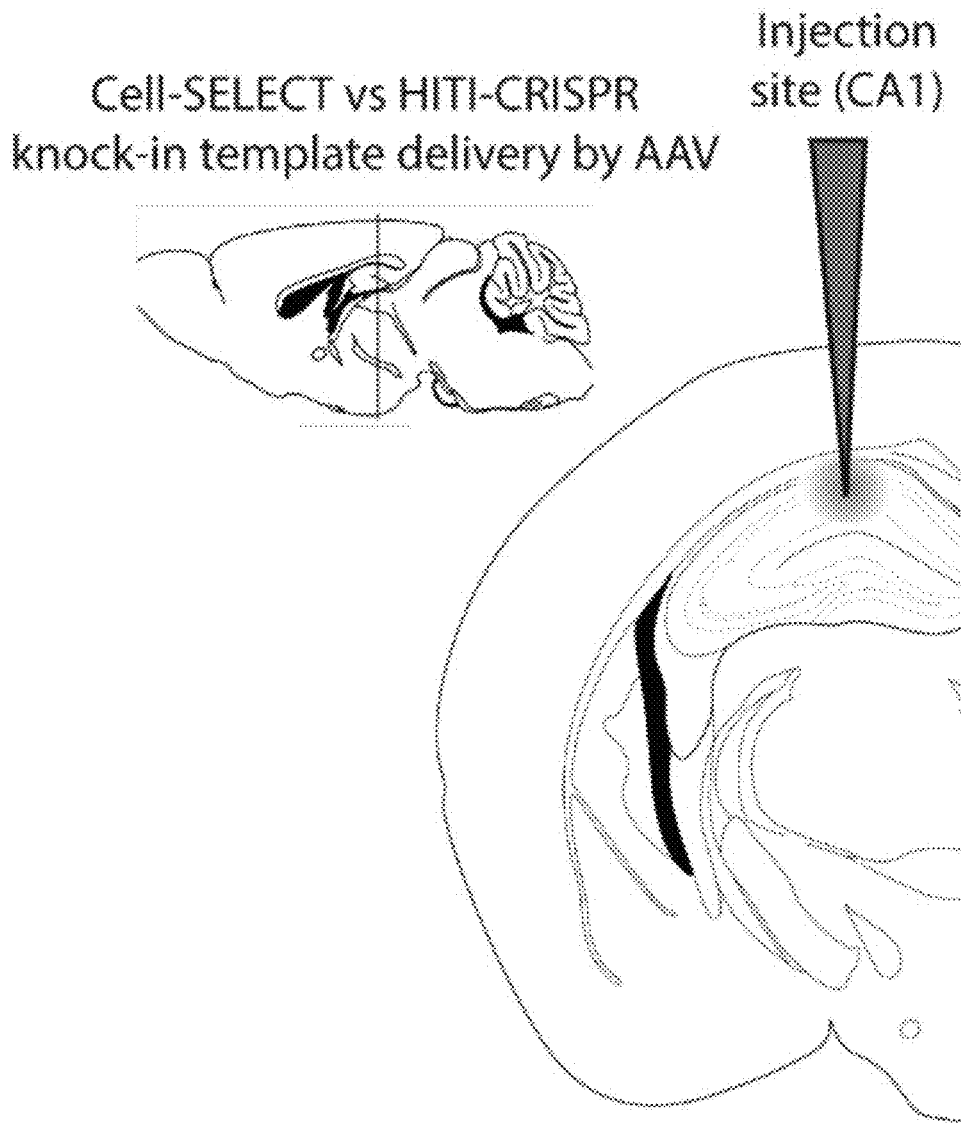
FIGS. 6A-6C depict data related to in vivo gene editing in live animals.
Figure 6B:
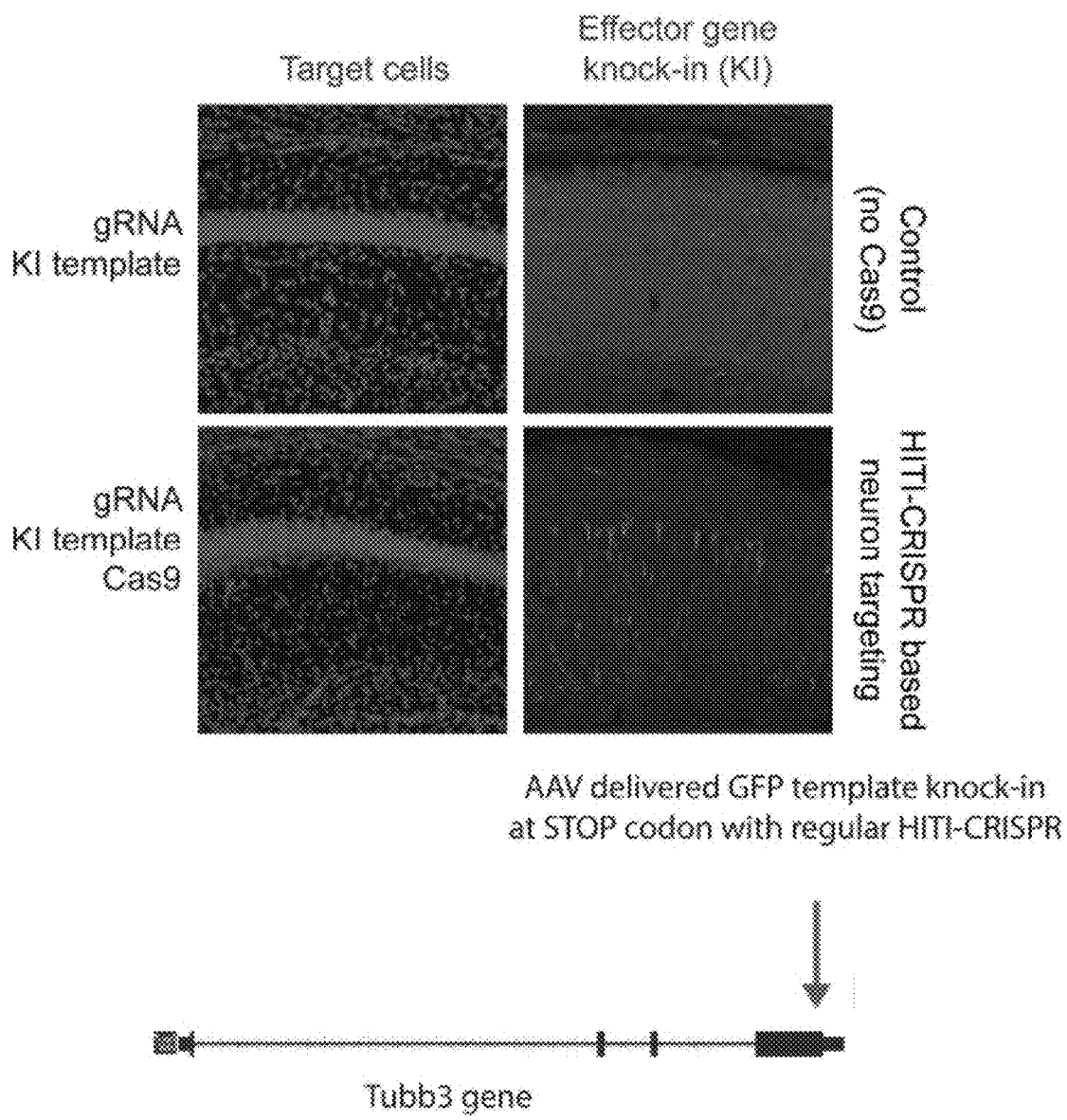
Figure 6C:
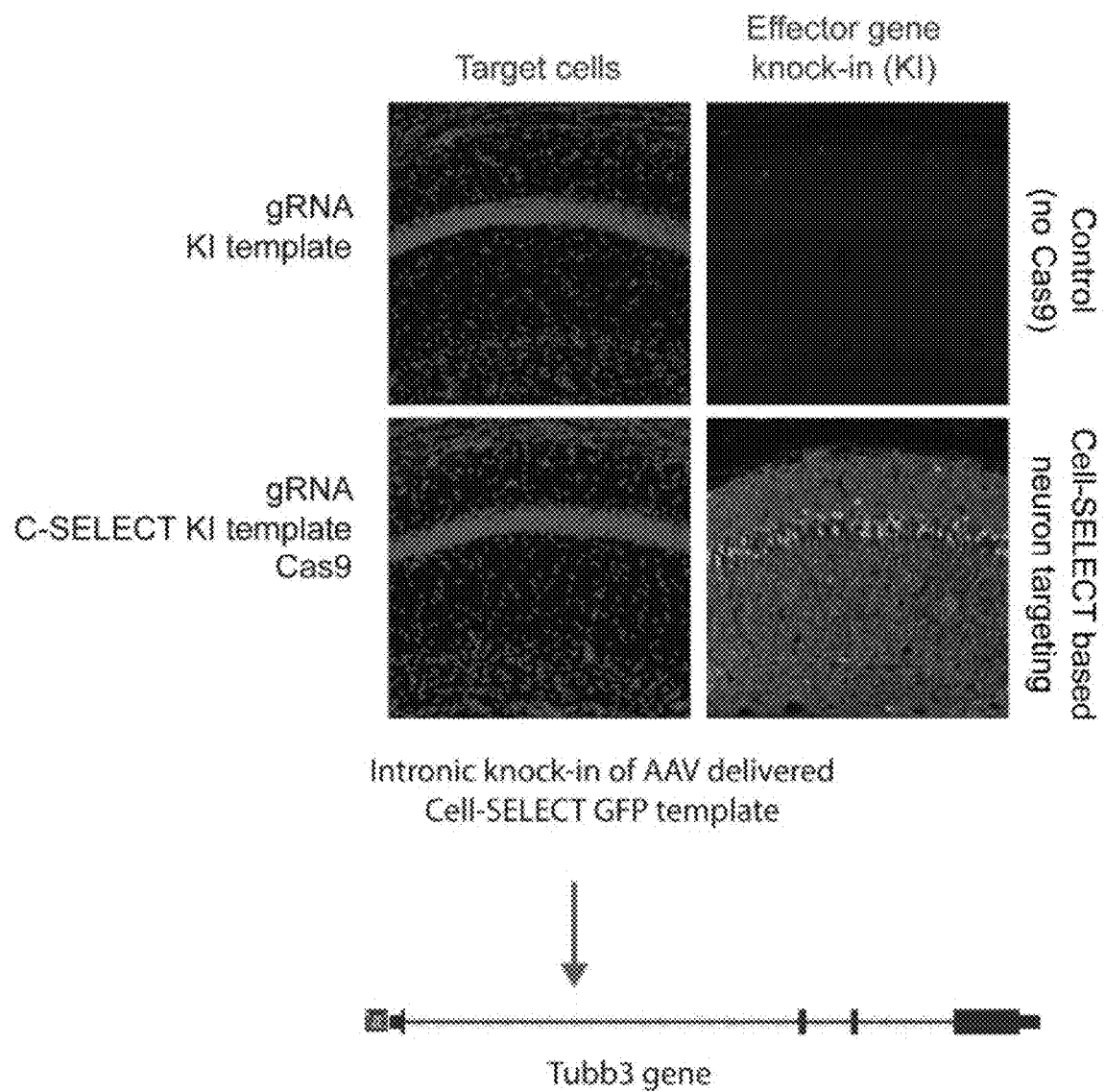

Comparison of HITI-CRISPR and Cell-SELECT Methods in Cell Culture and Live Animals This example provides proof of concept for the Cell-SELECT method provided herein and demonstrates the several fold higher cell targeting efficiencies achieved with the disclosed methods and compositions as compared to currently available solutions. FIGS. 5A-5C demonstrate the high yield knock-in efficiency of the Cell-SELECT method as compared to other gene editing based gene tagging technologies in a cell culture model expressing the targeted Tubb3 gene (N2A cell line). FIG. 5A shows the regular gene tagging approach that uses homology-independent-targeted integration (HITI) CRISPR based knock-in of the GFP reporter at the stop-codon of the Tubb3 gene. The sensitivity of the traditional gene tagging methods to imprecisions of the NHEJ dependent DNA repair and of Cas9 cleavage result in modest effector gene expression in cells where the target gene was expressed. The control condition lacks Cas9 expression. The test condition cells have been transfected with Cas9, Tubb3 stop codon targeting gRNA and promoter-less GFP knock-in construct. SEQ ID NO: 2 comprises a pAAV-CELL-SELECT construct for targeted viral knock-in of fluorescent reporter EYFP. In some embodiments, the expression of the targeting molecule (e.g., gRNA) can be driven by an RNA polymerase III promoter (e.g., U6 snRNA promoter). FIG. 5B shows the high efficiency of Cell-SELECT based effector gene (GFP) targeting to Tubb3 expressing cells. Cell-SELECT donor insertions was guided to the first intron of the Tubb3 gene and the effector gene was spliced to the expressed Tubb3 first exon. Effector gene expression was dependent on the presence of Cas9 nuclease. FIG. 5C shows the quantification of cell targeting efficiencies with regular HITI-CRISPR based gene tagging and contrasts that to the Cell-SELECT method. Cell-SELECT achieves 2.5× higher cellular targeting efficiency as compared to the state of the art gene editing based effector-gene knock-in approaches (n=8, ***-p<0.001, unpaired t-test). FIGS. 6A-6C shows that Cell-SELECT based in vivo gene editing as disclosed herein achieve efficient and high levels of effector gene expression in desired cell types in live animals. FIG. 6A shows a non-limiting exemplary schematic illustration of the injection and testing of AAV viral vector based in vivo gene editing in the mouse brain. Effector gene (GFP) carrying HITI CRISPR or Cell-SELECT templates and gRNA targeting effector gene integration to the pan-neuronally expressed Tubb3 locus were employed. Cas9 gene was supplied in trans from H11 locus. AAV injections (300 nL of virus at 10'12 virus particles/ml) were directed to the CA1 region of hippocampus. Cell-SELECT was found to achieve efficient and high levels of effector gene expression in desired cell types in vivo reaching more than an order of magnitude higher effector gene knock-in efficiencies than regular HITI-CRISPR based gene tagging. FIG. 6B depicts Tubb3 integration site and representative knock in efficiency with regular HITI-CRISPR based in vivo gene editing. FIG. 6C depicts Tubb3 integration site and representative knock in efficiency with Cell-SELECT based in vivo gene editing.

Example 3

In Vivo Gene Editing

Figure 7A:
Figure 7B:
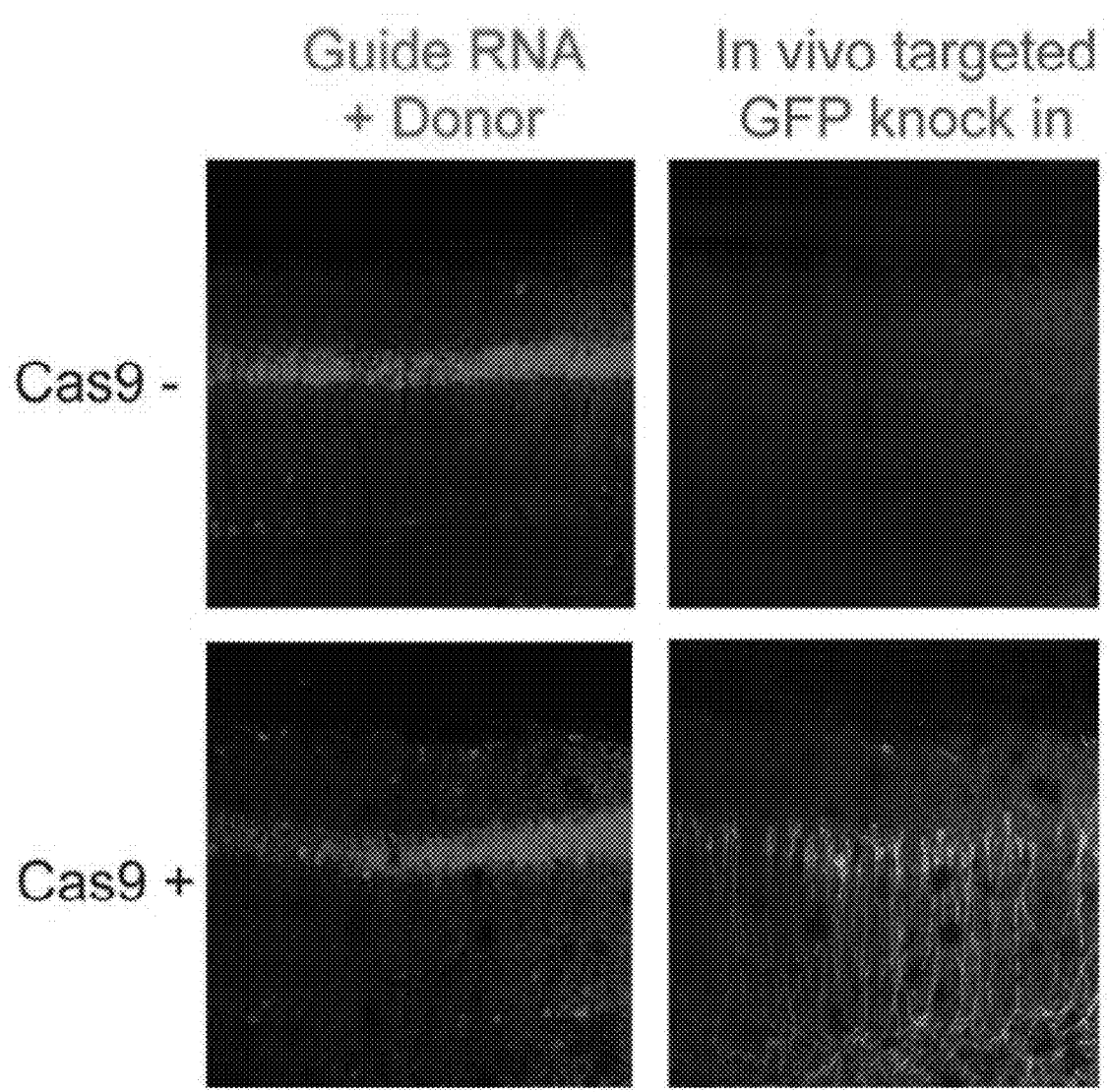

FIGS. 7A-7B demonstrate the cell targeting efficiency of Tubb3 expressing neurons with in vivo gene editing based effector gene knock-in. FIG. 7A shows a non-limiting exemplary schematic illustration of the experimental design, where AAV-based viral vectors were used to deliver the knock-in construct carrying the GFP gene and gene editing nuclease reagents to the mouse hippocampal CA1 region via stereotactic injections. FIG. 7B shows the results of an experiment for an unoptimized targeted in vivo genomic integration of a GFP construct into the pan-neuronally expressed Tubb3 locus using HITI CRISPR based knock-in donor introduction. The experiment yielded~10% targeting efficiency for the effector gene expression with successful targeting taking place only in the presence of the Cas9 recombinase.

Example 4

Identification of a Candidate Locus for Cell-SELECT Targeting

This example provides further validation for the Cell-SELECT method disclosed herein. In some embodiments, the methods and compositions provided herein can be employed to manipulate behavior-mediating neuron types in a mammalian brain. The disclosed Cell-SELECT methods can be used as a method to functionally manipulate molecularly defined neurons in the mammalian central nervous system that control essential physiological or behavioral functions. For example, the expression of pain is mediated by activity in molecularly distinct cell types in various mammalian brain centers such as the lateral parabrachial nucleus (LPBN). These cell types differ from other neurons in these brain centers by virtue of distinct gene expression programs that are active in these cells.

Figure 8A:
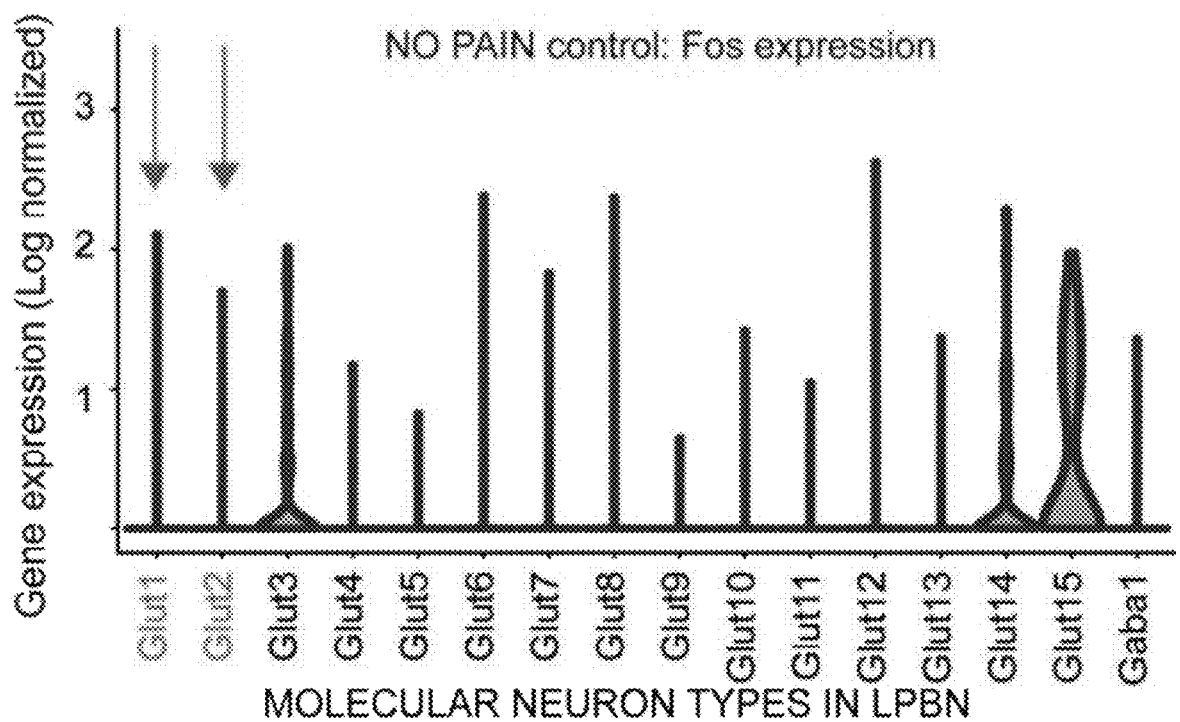
FIGS. 8A-8C depict single cell RNA-seq data in the major mammalian brain pain relay—lateral parabrachial nucleus (LPBN).
Figure 8B:
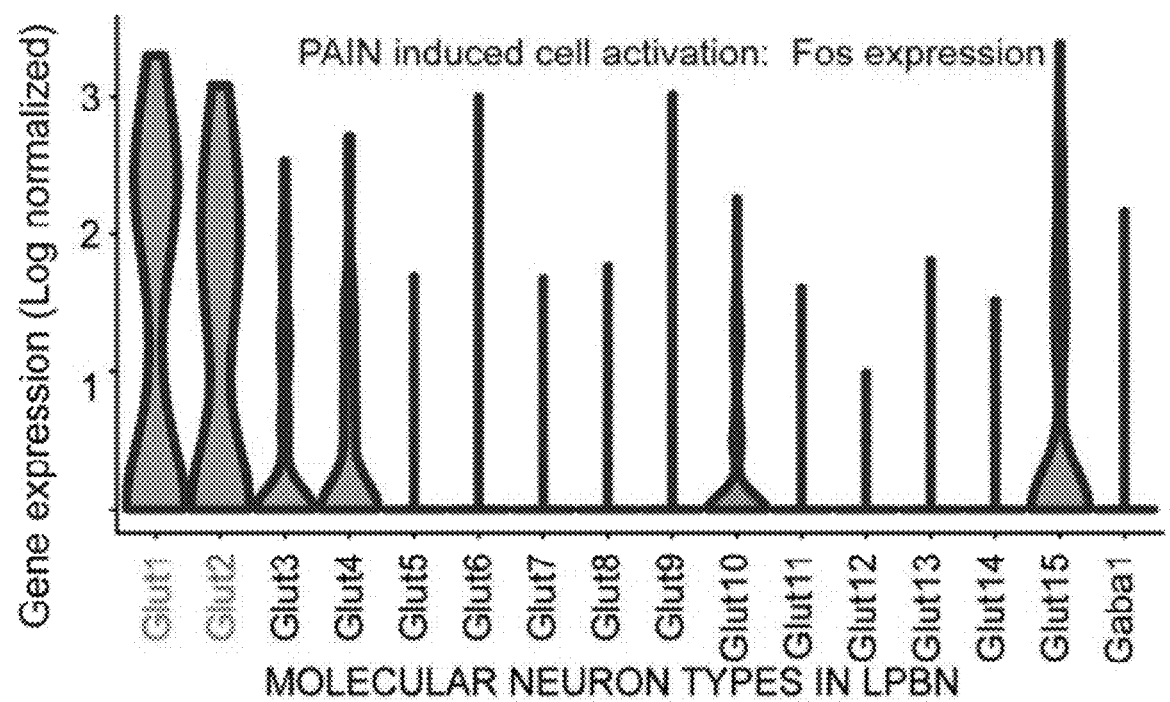
Figure 8C:
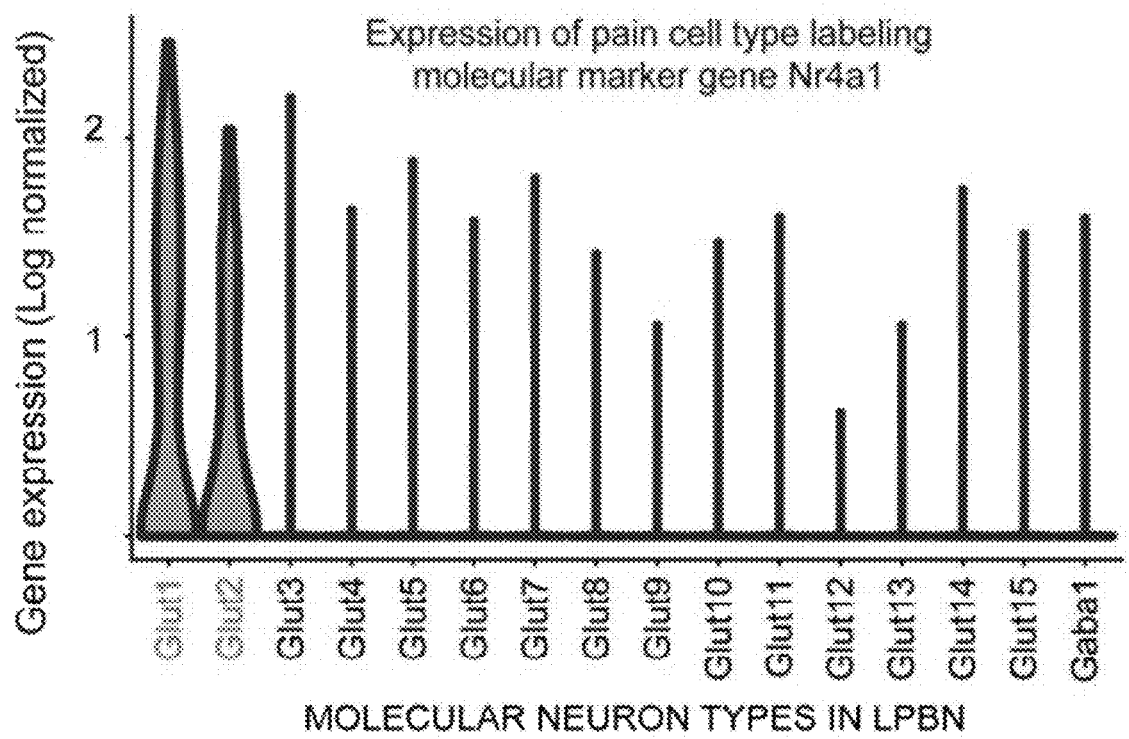

FIGS. 8A-8B show the neural activity induced immediate early gene expression in control condition or after pain induction in molecular cell-types in the major mammalian brain pain relay—lateral parabrachial nucleus (LPBN). Single cell RNA-seq in the midbrain nucleus LPBN revealed two cell types that are robustly activated by exposure to pain (Glut1, Glut2, red arrows). Width and height of violin plots indicates proportion of cells expressing a given gene. FIG. 8C shows the expression of pain cell type labeling molecular marker gene Nr4a1. Pain activated cells are selectively labeled by the expression of Nr4a1 gene identifying candidate locus for Cell-SELECT targeting. Thus, an identification of two pain activated molecular cell types in the mouse midbrain nucleus LPBN— a pain relay in the central nervous system that is essential for pain perception was made as shown in FIGS. 8A-8C. This context is an ideal challenge, as the LPBN contains 14 other molecular cell types that regulate taste, blood pressure, breathing and other essential physiological functions. Cells that are essential for the detection of pain and are concomitantly driven by peripheral noxious stimuli express the gene Nr4a1 (FIGS. 8A-8C). The Cell-SELECT methods provided herein can be used to control the animal's sensitivity to pain inducing stimuli by delivering a synaptic function blocking gene TNT to LPBN neurons with AAV viral vectors carrying the Cell-SELECT knock in donor as well as Cas9 and gRNA constructs targeting Cell-SELECT donor integration to the first intron of Nr4a1 gene. This can result in selective synaptic blockade of pain processing neurons in LPBN and consequently downregulates the pain experience by directly functionally re-engineering the underlying circuit function.

Single cell profiling by RNA-seq revealed both molecular cell types as well as cell type specifically expressed genetic programs. The disclosed single cell RNA-seq data from LPBN has identified several genes that are selectively expressed in pain neurons (e.g. Nr4a1 in FIG. 8C). This information enables the design of an AAV viral vector delivering Cell-SELECT constructs containing an effector gene (e.g., fluorescent reporter) targeting the intron of one or more of those genes. In some embodiments, Cell-SELECT reagents can be delivered to the midbrain by stereotactic brain injection. The analysis provided herein identifies genetic loci that reliably and selectively label pain mediating molecular neuron types in the midbrain. In some embodiments, the effector gene comprises a synaptic or chronic activity blocking gene (e.g., TNT, Kir2.1 etc.) to functionally silence pain mediating cells in LPBN, which can result in changes in pain sensitivity and perception in a panel of acute and chronic pain assays.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A composition, comprising:
(i) a programmable nuclease or a nucleic acid encoding the programmable nuclease, wherein the programmable nuclease comprises *Streptococcus pyogenes* Cas9 (SpCas9), *Staphylococcus aureus* Cas9 (SaCas9), Cas9, or any combination thereof, optionally wherein the programmable nuclease is capable of inducing a double-stranded DNA break;
(ii) a targeting molecule or a nucleic acid encoding the targeting molecule, wherein the targeting molecule is capable of associating with the programmable nuclease, optionally wherein the targeting molecule comprises single strand DNA or single strand RNA, further optionally wherein the targeting molecule comprises a single guide RNA (sgRNA), and/or
(iii) a donor nucleic acid or a nucleic acid encoding the donor nucleic acid, wherein the donor nucleic acid comprises a recognition site, a splice acceptor site, a self-cleaving peptide sequence, an effector gene,
  (a) a translation frame linker, optionally wherein the translation frame linker places the effector gene in translational frame with the preceding exon of a target gene, or
  (b) a target gene coding sequence downstream of an intron comprised in the target gene, and
an optional transcript stabilization element, and wherein the targeting molecule is complementary to the recognition site and the programmable nuclease is capable of cleaving the recognition site.

2. The composition of claim 1,
wherein upon introduction into a cell of a subject comprising a target gene differentially expressed in a unique cell type and/or in a cell during a unique cell state, wherein the intron comprising the recognition site, the donor nucleic acid is capable of being incorporated into the intron through non-homologous end joining (NHEJ)-dependent DNA repair.

3. The composition of claim 2, wherein the donor nucleic acid comprises the structure 5'-[recognition site]-[splice acceptor site]-[translation frame linker]-[self-cleaving peptide sequence]-[effector gene]-3'.

4. The composition of claim 2, wherein the donor nucleic acid comprises the structure 5'-[recognition site]-[splice acceptor site]-[target gene coding sequence downstream of the intron]-[self-cleaving peptide sequence]-[effector gene]-3'.

5. The composition of claim 2, wherein the recognition site of the donor nucleic acid and the recognition site of the intron are the same, optionally wherein the recognition site does not exist after the donor nucleic acid has been properly incorporated into the intron.

6. The composition of claim 2, wherein the unique cell type and/or the cell in the unique cell state is associated with the pathology of a disease or disorder.

7. The composition of claim 1, wherein the expression of the effector gene is capable of modulating cellular membrane potential, optionally wherein the expression of the effector gene is capable of altering the membrane potential of the cell by depolarizing the cell and/or hyperpolarizing the cell.

8. The composition of claim 1, wherein the expression of the effector gene is capable of reducing synaptic transmission by at least 10 percent.

9. The composition of claim 1, wherein the effector gene comprises interleukin-12 (IL-12), Kir2.1, tetanus toxin (TNT), a DREADD receptor, Channelrhodopsin-2, or any combination thereof.

10. The composition of claim 1, wherein the expression of the effector gene is capable of sensitizing the cell to a drug, a prodrug a pharmacological compound, temperature change, or light.

11. The composition of claim 1, wherein the effector gene is capable of inducing cell death, optionally wherein the effector gene comprises cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof.

12. The composition of claim 1, wherein, upon introduction into a cell, the composition achieves an at least 10 percent higher targeting efficiency as compared to a homology directed repair (HDR)-based method and/or an at least 10 percent higher targeting efficiency as compared to a Homology Independent Targeted Integration (HITI)-based method integrating an effector gene into an exon.

13. The composition of claim 1, wherein the self-cleaving peptide sequence comprises porcine teschovirus-1 2A peptide (P2A), Thosea asigna virus 2A peptide (T2A), equine rhinitis A virus 2A peptide (E2A), foot-and-mouth disease virus 2A peptide (F2A), or any combination thereof.

14. The composition of claim 1, wherein the transcript stabilization element is capable of enhancing the stability of a transcript of the effector gene, optionally wherein the transcript stabilization element comprises woodchuck hepatitis post-translational regulatory element (WPRE), bovine growth hormone polyadenylation (bGH-polyA) signal sequence, human growth hormone polyadenylation (hGH-polyA) signal sequence, or any combination thereof.

15. The composition of claim 1, wherein the splice acceptor site is recognizable and cleavable by a spliceosome, optionally wherein the splice acceptor site comprises a branchpoint, a polypyrimidine tract, a 3' splice site, or any combination thereof.

16. The composition of claim 1, wherein at least two of the programmable nuclease, the targeting molecule, and the donor nucleic acid are encoded on the same nucleic acid.

17. The composition of claim 1, wherein at least two of the programmable nuclease, the targeting molecule, and the donor nucleic acid are encoded on different nucleic acids.

18. The composition of claim 1, wherein the nucleic acid encoding the programmable nuclease, the nucleic acid encoding the targeting molecule, and/or the nucleic acid encoding the donor nucleic acid are component of a vector and/or a ribonucleoprotein (RNP) complex.

* * * * *

SEQUENCE LISTING

```
Sequence total quantity: 3
SEQ ID NO: 1              moltype = DNA   length = 1405
FEATURE                   Location/Qualifiers
misc_feature              1..1405
                          note = Cell-SELECT donor construct
misc_feature              26..48
                          note = CRISPR gRNA target
misc_feature              55..120
                          note = Adenovirus Splice acceptor
misc_feature              80..84
                          note = Branch point
misc_feature              121..126
                          note = Translation frame linker
misc_feature              127..183
                          note = P2A (self cleaving peptide)
misc_feature              184..900
                          note = Effector/reporter gene (EYFP)
misc_feature              910..1158
                          note = WPRE3 (transcription stabilization element)
misc_feature              1159..1383
                          note = bGH poly(A) signal (transcription stabilization
                           element)
source                    1..1405
                          mol_type = other DNA
                          organism = synthetic construct
SEQUENCE: 1
aaaaaccgg  gcgcgacttc tagatgagca taagagacct cagctgggaa gctttagggc   60
gcagtagtcc agggtttcct tgatgatgtc atacttatcc tgtcccttt  ttttccacag   120
gtcgacgcca cgaacttctc tctgttaaag caagcaggag acgtggaaga aaaccccggt  180
cctgtgagca agggcgagga gctgttcacc ggggtggtgc ccatcctggt cgagctggac  240
ggcgacgtaa acggccacaa gttcagcgtg tccggcgagg gcgagggcga tgccacctac  300
ggcaagctga cccctgaagtt catctgcacc accggcaagc tgcccgtgcc ctggcccacc  360
ctcgtgacca ccctgaccta cggcgtgcag tgcttcagcc gctaccccga ccacatgaag  420
cagcacgact tcttcaagtc cgccatgccc gaaggctacg tccaggagcg caccatcttc  480
ttcaaggacg acggcaacta caagacccgc gccgaggtga agttcgaggg cgacaccctg  540
gtgaaccgca tcgagctgaa gggcatcgac ttcaaggagg acggcaacat cctggggcac  600
aagctggagt acaactacaa cagccacaac gtctatatca tggccgacaa gcagaagaac  660
ggcatcaagg tgaacttcaa gatccgccac aacatcgagg acggcagcgt gcagctcgcc  720
gaccactacc agcagaacac ccccatcggc gacggccccg tgctgctgcc cgacaaccac  780
tacctgagca cccagtccgc cctgagcaaa gaccccaacg agaagcgcga tcacatggtc  840
ctgctggagt tcgtgaccgc cgccgggatc actctcggca tggacgagct gtacaagtaa  900
taagaattcg ataatcaacc tctggattac aaaatttgtg aaagattgac tggtattctt  960
aactatgttg ctccttttac gctatgtgga tacgctgctt taatgccttt gtatcatgct  1020
attgcttccc gtatggcttt cattttctcc tccttgtata aatcctggtt agttcttgcc  1080
acggcggaac tcatcgccgc ctgccttgcc cgctgctgga caggggctcg gctgttgggc  1140
actgacaatt ccgtggtgct gtgccttcta gttgccagcc atctgttgtt tgcccctccc  1200
ccgtgccttc cttgaccctg gaaggtgcca ctcccactgt cctttcctaa taaaatgagg  1260
aaattgcatc gcattgtctg agtaggtgtc attctattct ggggggtggg gtggggcagg  1320
acagcaaggg ggaggattgg gaagacaata gcaggcatgc tggggatgcg gtgggctcta  1380
tggggatcca aaagggccc aaaaa                                         1405

SEQ ID NO: 2              moltype = DNA   length = 4634
FEATURE                   Location/Qualifiers
misc_feature              1..4634
                          note = pAAV-CELL-SELECT for targeted viral knock-in of
                           fluorescent reporter EYFP
misc_feature              1..141
                          note = L-ITR
misc_feature              172..412
                          note = U6 promoter
misc_feature              421..440
                          note = Tubb3 gRNA1 seq
misc_feature              441..516
                          note = gRNA scaffold
misc_feature              530..552
                          note = CRISPR gRNA1 target
misc_feature              559..586
                          note = Splice acceptor (HockM)
misc_feature              562..566
                          note = Branch point
misc_feature              593..649
                          note = P2A
misc_feature              650..1366
                          note = EGFP
misc_feature              1376..1624
                          note = WPRE3
misc_feature              1625..1849
                          note = bGH poly(A) signal
```

| misc_feature | 1897..2037 |
| | note = R-ITR |
| misc_feature | 2129..2435 |
| | note = f1 Origin |
| misc_feature | 2954..3811 |
| | note = AmpR |
| misc_feature | 3962..4629 |
| | note = pUC ori |
| source | 1..4634 |
| | mol_type = other DNA |
| | organism = synthetic construct |

SEQUENCE: 2

```
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca  120
actccatcac tagggnttcc tgcggccgca cgcgtcaagg tcgggcagga agagggccta  180
tttcccatga ttccttcata tttgcatata cgatacaagg ctgttagaga gataattaga  240
attaatttga ctgtaaacac aaagatatta gtacaaaata cgtgacgtag aaagtaataa  300
tttcttgggt agtttgcagt tttaaaatta tgttttaaaa tggactatca tatgcttacc  360
gtaacttgaa agtatttcga tttcttggct ttatatatct tgtggaaagg acgaaacacc  420
gagcataaga gacctcagct gttttagagc tagaaatagc aagttaaaat aaggctagtc  480
cgttatcaac ttgaaaaagt ggcaccgagt cggtgctttt tttctagatg agcataagag  540
acctcagctg ggaagcttct tctgacctct tctcttcctc ccacaggtcg acgccacgaa  600
cttctctctg ttaaagcaag caggagacgt ggaagaaaac cccggtcctg tgagcaaggg  660
cgaggagctg ttcaccgggg tggtgcccat cctggtcgag ctggacggcg acgtaaacgg  720
ccacaagttc agcgtgtccg gcgagggcga gggcgatgcc acctacggca agctgaccct  780
gaagttcatc tgcaccaccg gcaagctgcc cgtgccctgg cccaccctcg tgaccaccct  840
gacctacggc gtgcagtgct tcagccgcta ccccgaccac atgaagcagc acgacttctt  900
caagtccgcc atgcccgaag gctacgtcca ggagcgcacc atcttcttca aggacgacgg  960
caactacaag acccgcgccg aggtgaagtt cgagggcgac accctggtga accgcatcga 1020
gctgaagggc atcgacttca aggaggacgg caacatcctg gggcacaagc tggagtacaa 1080
ctacaacagc cacaacgtct atatcatggc cgacaagcag aagaacggca tcaaggtgaa 1140
cttcaagatc cgccacaaca tcgaggacgg cagcgtgcag ctcgccgacc actaccagca 1200
gaacaccccc atcggcgacg gccccgtgct gctgcccgac aaccactacc tgagcaccca 1260
gtccgccctg agcaaagacc ccaacgagaa gcgcgatcac atggtcctgc tggagttcgt 1320
gaccgccgcc gggatcactc tcggcatgga cgagctgtac aagtaataag aattcgataa 1380
tcaacctctg gattacaaaa tttgtgaaag attgactggt attcttaact atgttgctcc 1440
ttttacgcta tgtggatacg ctgctttaat gcctttgtat catgctattg cttcccgtat 1500
ggctttcatt ttctcctcct tgtataaatc tggttagtt cttgccacgg cggaactcat 1560
cgccgcctgc cttgcccgct gctggacagg ggctccgtg ttgggcactg acaattccgt 1620
ggtgctgtgc cttctagttg ccagccatct gttgtttgcc cctcccccgt gccttccttg 1680
accctggaag gtgccactcc cactgtcctt tcctaataaa atgaggaaat tgcatcgcat 1740
tgtctgagta ggtgtcattc tattctgggg ggtgggttgg gcaggacag caaggggag 1800
gattgggaag acaatagcag gcatgctggg gatgcggtgg gctctatggg gatccaaaaa 1860
gggcccatct cgagcacgtg cggaccgagc ggccgcagga accctagtg atggagttgg 1920
ccactccctc tctgcgcgct cgctcgctca ctgaggccgg gcgaccaaag gtcgcccgac 1980
gcccgggctt tgcccgggcg gcctcagtga gcgagcgagc gcgcagctgc ctgcaggggc 2040
gcctgatgcg gtattttctc cttacgcatc tgtgcggtat ttcacaccgc atacgtcaaa 2100
gcaaccatag tacgcgccct gtagcggcgc attaagcgcg gcgggtgtgg tggttacgcg 2160
cagcgtgacc gctacacttg ccagcgccct agcgcccgct cctttcgctt tcttcccttc 2220
ctttctcgcc acgttcgccg gctttccccg tcaagctcta aatcggggc tccctttagg 2280
gttccgattt agtgctttac ggcacctcga ccccaaaaaa cttgatttgg gtgatggttc 2340
acgtagtggg ccatcgccct gatagacggt ttttcgccct ttgacgttgg agtccacgtt 2400
ctttaatagt ggactcttgt tccaaactgg aacaacactc aacccatct cgggctattc 2460
ttttgattta agggatttt gccgatttc ggcctattgg ttaaaaatg agctgattta 2520
acaaaaattt aacgcgaatt ttaacaaaat attaacgttt acaatttat ggtgcactct 2580
cagtacaatc tgctctgatg ccgcatagtt aagccagccc cgacaccgc caacaccgt 2640
tgacgcgcc tgacgggctt gtctgctccc ggcatccgct tacagacaag ctgtgaccgt 2700
ctccgggagc tgcatgtgtc agaggttttc accgtcatca ccgaaacgcg cgagacgaaa 2760
gggcctcgtg atacgcctat ttttataggt taatgtcatg ataatagtg tttcttagac 2820
gtcaggtggc acttttcggg gaaatgtgcg cggaacccct atttgtttat ttttctaaat 2880
acattcaaat atgtatccgc tcatgagaca ataaccctga taaatgcttc aataatattg 2940
aaaaaggaag agtatgagta ttcaacattt ccgtgtcgcc cttattccct ttttgcggc 3000
atttgccttt cctgttttg ctcacccaga aacgctggtg aaagtaaaag atgctgaaga 3060
tcagttgggt gcacgagtgg gttacatcga actggatctc aacagcggta agatccttga 3120
gagttttcgc cccgaagaac gttttccaat gatgagcact tttaaagttc tgctatgtgg 3180
cgcggtatta tcccgtattg acgccgggca agagcaactc ggtcgccgca tacactattc 3240
tcagaatgac ttggttgagt actcaccagt cacagaaaag catcttacgg atggcatgac 3300
agtaagagaa ttatgcagtg ctgccataac catgagtgat aacactgcgg ccaacttact 3360
tctgacaacg atcggaggac cgaaggagct aaccgctttt ttgcacaaca tgggggatca 3420
tgtaactcgc cttgatcgtt gggaaccgga gctgaatgaa gccataccaa acgacgagcg 3480
tgacaccacg atgcctgtag caatggcaac aacgttgcgc aaactattaa ctggcgaact 3540
acttactcta gcttcccggc aacaattaat agactggatg gaggcggata agttgcagg 3600
accacttctg cgctcggccc ttccggctgg ctggtttatt gctgataaat ctggagccgg 3660
tgagcgtggg tctcgcggta tcattgcagc actggggcca gatggtaagc cctcccgtat 3720
cgtagttatc tacacgacgg ggagtcagge aactatggat gaacgaaata gacagatcgc 3780
tgagataggt gcctcactga ttaagcattg gtaactgtca gaccaagttt actcatatat 3840
actttagatt gatttaaaac ttcattttta atttaaaagg atctaggtga agatcctttt 3900
tgataatctc atgaccaaaa tcccttaacg tgagttttcg ttccactgag cgtcagaccc 3960
cgtagaaaag atcaaaggat cttcttgaga tcctttttt ctgcgcgtaa tctgctgctt 4020
```

```
gcaaacaaaa aaaccaccgc taccagcggt ggtttgtttg ccggatcaag agctaccaac   4080
tcttttccg aaggtaactg gcttcagcag agcgcagata ccaaatactg tccttctagt   4140
gtagccgtag ttaggccacc acttcaagaa ctctgtagca ccgcctacat acctcgctct   4200
gctaatcctg ttaccagtgg ctgctgccag tggcgataag tcgtgtctta ccgggttgga   4260
ctcaagacga tagttaccgg ataaggcgca gcggtcgggc tgaacggggg gttcgtgcac   4320
acagcccagc ttggagcgaa cgacctacac cgaactgaga tacctacagc gtgagctatg   4380
agaaagcgcc acgcttcccg aagggagaaa ggcggacagg tatccggtaa gcggcagggt   4440
cggaacagga gagcgcacga gggagcttcc agggggaaac gcctggtatc tttatagtcc   4500
tgtcgggttt cgccacctct gacttgagcg tcgatttttg tgatgctcgt caggggggcg   4560
gagcctatgg aaaaacgcca gcaacgcggc cttttttacgg ttcctggcct tttgctggcc   4620
ttttgctcac atgt                                                    4634

SEQ ID NO: 3            moltype = DNA  length = 4904
FEATURE                 Location/Qualifiers
misc_feature            1..4904
                        note = pAAV-CELL-SELECT for targeted viral knock-in of
                         optogenetic activatory Chr2
misc_feature            1..141
                        note = L-ITR
misc_feature            172..412
                        note = U6 promoter
misc_feature            421..440
                        note = Tubb3 gRNA1 seq
misc_feature            441..516
                        note = gRNA scaffold
misc_feature            530..552
                        note = CRISPR gRNA1 target
misc_feature            559..586
                        note = Splice acceptor (HockM)
misc_feature            562..566
                        note = Branch point
misc_feature            593..649
                        note = P2A
misc_feature            650..1573
                        note = ChR2(H134R)
misc_feature            1577..1603
                        note = HA
misc_feature            1604..1630
                        note = HA
misc_feature            1646..1894
                        note = WPRE3
misc_feature            1895..2119
                        note = bGH poly(A) signal
misc_feature            2167..2307
                        note = R-ITR
misc_feature            2399..2705
                        note = f1 Origin
misc_feature            3224..4081
                        note = AmpR
misc_feature            4232..4899
                        note = pUC ori
source                  1..4904
                        mol_type = other DNA
                        organism = synthetic construct
SEQUENCE: 3
cctgcaggca gctgcgcgct cgctcgctca ctgaggccgc ccgggcaaag cccgggcgtc   60
gggcgaccct tggtcgcccg gcctcagtga gcgagcgagc gcgcagagag ggagtggcca   120
actccatcac taggggttcc tgcggccgca cgcgtcaagg tcgggcagga agagggccta   180
tttcccatga ttccttcata tttgcatata cgatacaagg ctgttagaga gataattaga   240
attaatttga ctgtaaacac aaagatatta gtacaaaata cgtgacgtag aaagtaataa   300
tttcttgggt agtttgcagt tttaaaatta tgttttaaaa tggactatca tatgcttacc   360
gtaacttgaa agtatttcga tttcttggct ttatatatct tgtggaaagg acgaaacacc   420
gagcataaga gacctcagct gttttagagc tagaaatagc aagttaaaat aaggctagtc   480
cgttatcaac ttgaaaaagt ggcaccgagt cggtgcttt tctctagatg agcataagag   540
acctcagctg ggaagcttct tctgacctct tctcttcctc ccacaggtcg acgccacgaa   600
cttctctctg ttaaagcaag caggagacgt ggaagaaaac cccggtcctg actatggcgg   660
cgctttgtct gccgtcggac gcgaactttt gttcgttact aatcctgtgg tggtgaacgg   720
gtccgtcctg gtccctgagg atcaatgtta ctgtgccgga tggattgaat ctcgcggcac   780
gaacggcgct cagaccgcgt caaatgtcct gcagtgtctg cagcaggat tcagcatttt   840
gctgctgatg ttctatgcct accaaacctg gaaatctaca tgcggctggg aggagatcta   900
tgtgtgcgcc attgaaatgg ttaaggtgat tctcgagttc ttttttgagt ttaagaatcc   960
ctctatgctc taccttgcca caggacaccg ggtgcagtgg ctgcgctatg cagagtggct   1020
gctcacttgt cctgtcatcc ttatccgcct gagcaacctc accggcctga gcaacgacta   1080
cagcaggaga accatgggac tccttgtctc agacatcaagg actatcgtgt gggggctac   1140
cagcgccatg gcaaccggct atgttaaagt catcttcttt tgtctcggat tgtgctatgc   1200
cgcgaacaca tttttttcacg ccgccaaagc atatatcgag ggttatcata ctgtgccaaa   1260
gggtcggtgc cgccaggtcg tgaccggcat ggcatggctg tttttcgtga ctgggggtat   1320
gttcccaatt ctcttcattt tggggccga aggttttggc gtcctgagcg tctatggctc   1380
caccgtaggt cacacgatta ttgatctgat gagtaaaaat tgttggggt tgttgggaca   1440
```

-continued

```
ctacctgcgc gtcctgatcc acgagcacat attgattcac ggagatatcc gcaaaaccac 1500
caaactgaac atcggcggaa cggagatcga ggtcgagact ctcgtcgaag acgaagccga 1560
ggccggagcc gtggcatacc cctacgacgt gcccgactac gcctatccat atgatgtccc 1620
agactatgct gctagctaag aattcgataa tcaacctctg gattacaaaa tttgtgaaag 1680
attgactggt attcttaact atgttgctcc ttttacgcta tgtggatacg ctgctttaat 1740
gcctttgtat catgctattg cttcccgtat ggctttcatt ttctcctcct tgtataaatc 1800
ctggttagtt cttgccacgg cggaactcat cgccgcctgc cttgcccgct gctggacagg 1860
ggctcggctg ttgggcactg acaattccgt ggtgctgtgc cttctagttg ccagccatct 1920
gttgttttgcc cctccccgt gccttccttg accctggaag gtgccactcc cactgtcctt 1980
tcctaataaa atgaggaaat tgcatcgcat tgtctgagta ggtgtcattc tattctgggg 2040
ggtggggtgg ggcaggacag caaggggag gattgggaag acaatagcag gcatgctggg 2100
gatgcggtgg gctctatggg gatccaaaaa gggcccatct cgagcacgtg cggaccgagc 2160
ggccgcagga acccctagtg atggagttgg ccactccctc tctgcgcgct cgctcgctca 2220
ctgaggccgg gcgaccaaag gtcgcccgac gcccgggctt tgcccgggcg gcctcagtga 2280
gcgagcgagc gcgcagctgc ctgcaggggc gcctgatgcg gtattttctc cttacgcatc 2340
tgtgcggtat ttcacaccgc atacgtcaaa gcaaccatag tacgcgccct gtagcggcgc 2400
attaagcgcg gcgggtgtgg tggttacgcg cagcgtgacc gctacacttg ccagcgccct 2460
agcgccgct cctttcgctt tcttcccttc ctttctcgcc acgttcgccg gctttccccg 2520
tcaagctcta aatcggggc tccctttagg gttccgattt agtgctttac ggcacctcga 2580
ccccaaaaaa cttgatttgg gtgatggttc acgtagtggg ccatcgccct gatagacggt 2640
ttttcgccct ttgacgttgg agtccacgtt ctttaatagt ggactcttgt tccaaactgg 2700
aacaacactc aaccctatct cgggctattc ttttgattta taagggattt tgccgatttc 2760
ggcctattgg ttaaaaaatg agctgattta acaaaaattt aacgcgaatt ttaacaaaat 2820
attaacgttt acaatttat ggtgcactct cagtacaatc tgctctgatg ccgcatagtt 2880
aagccagccc cgacacccgc caacacccgc tgacgcgccc tgacgggctt gtctgctccc 2940
ggcatccgct tacagacaag ctgtgaccgt ctccgggagc tgcatgtgtc agaggttttc 3000
accgtcatca ccgaaacgcg cgagacgaaa gggcctcgtg atacgcctat ttttataggt 3060
taatgtcatg ataataatgg tttcttagac gtcaggtggc acttttcggg gaaatgtgcg 3120
cggaacccct atttgtttat ttttctaaat acattcaaat atgtatccgc tcatgagaca 3180
ataaccctga taaatgcttc aataatattg aaaaaggaag agtatgagta ttcaacattt 3240
ccgtgtcgcc cttattccct tttttgcggc attttgcctt cctgttttg ctcacccaga 3300
aacgctggtg aaagtaaaag atgctgaaga tcagttgggt gcacgagtgg gttacatcga 3360
actggatctc aacagcggta agatccttga gagttttcgc cccgaagaac gttttccaat 3420
gatgagcact tttaaagttc tgctatgtgg cgcggtatta tcccgtattg acgccgggca 3480
agagcaactc ggtcgccgca tacactattc tcagaatgac ttggttgagt actcaccagt 3540
cacagaaaag catcttacgg atggcatgac agtaagagaa ttatgcagtg ctgccataac 3600
catgagtgat aacactgcgg ccaacttact tctgacaacg atcggaggac cgaaggagct 3660
aaccgctttt ttgcacaaca tgggggatca tgtaactcgc cttgatcgtt gggaaccgga 3720
gctgaatgaa gccataccaa acgacgagcg tgacaccacg atgcctgtag caatggcaac 3780
aacgttgcgc aaactattaa ctggcgaact acttactcta gcttcccggc aacaattaat 3840
agactggatg gaggcggata aagttgcagg accacttctg cgctcggccc ttccggctgg 3900
ctggtttatt gctgataaat ctggagccgg tgagcgtggg tctcgcggta tcattgcagc 3960
actggggcca gatggtaagc cctcccgtat cgtagttatc tacacgacgg gggagtcaggc 4020
aactatggat gaacgaaata gacagatcgc tgagataggt gcctcactga ttaagcattg 4080
gtaactgtca gaccaagttt actcatatat actttagatt gatttaaaac ttcatttta 4140
atttaaaagg atctaggtga agatcctttt tgataatctc atgaccaaaa tcccttaacg 4200
tgagttttcg ttccactgag cgtcagaccc cgtagaaaag atcaaaggat cttcttgaga 4260
tccttttttt ctgcgcgtaa tctgctgctt gcaaacaaaa aaaccaccgc taccagcggt 4320
ggtttgtttg ccggatcaag agctaccaac tctttttccg aaggtaactg gcttcagcag 4380
agcgcagata ccaaatactg tccttctagt gtagccgtag ttaggccacc acttcaagaa 4440
ctctgtagca ccgcctacat acctcgctct gctaatcctg ttaccagtgg ctgctgccag 4500
tggcgataag tcgtgtctta ccgggttgga ctcaagacga tagttaccgg ataaggcgca 4560
gcggtcgggc tgaacggggg gttcgtgcac acagcccagc ttggagcgaa cgacctacac 4620
cgaactgaga tacctacagc gtgagctatg agaaagcgcc acgcttcccg aagggagaaa 4680
ggcggacagg tatccggtaa gcggcagggt cggaacagga gagcgcacga gggagcttcc 4740
agggggaaac gcctggtatc tttatagtcc tgtcgggttt cgccacctct gacttgagcg 4800
tcgatttttg tgatgctcgt caggggggcg gagccatgg aaaaacgcca gcaacgcggc 4860
cttttacgg ttcctggcct tttgctggcc ttttgctcac atgt 4904
```